(12) United States Patent
Stratman et al.

(10) Patent No.: US 8,992,853 B2
(45) Date of Patent: Mar. 31, 2015

(54) DEVICES, SYSTEMS AND METHODS FOR LOCALIZED STERILIZATION

(71) Applicants: Burkert Contromatic Corp., Charlotte, NC (US); Burkert Werke GMBH, Ingelfingen (DE)

(72) Inventors: Harm Stratman, Davidson, NC (US); Heinz Duemmler, Indian Trail, NC (US); Ray M. Frey, Fort Mill, SC (US)

(73) Assignee: Bürkert Contromatic Corp., Charlotte, NC (US)

( * ) Notice: Subject to any disclaimer, the term of this patent is extended or adjusted under 35 U.S.C. 154(b) by 89 days.

(21) Appl. No.: 13/623,331

(22) Filed: Sep. 20, 2012

(65) Prior Publication Data

US 2013/0078140 A1    Mar. 28, 2013

Related U.S. Application Data

(60) Provisional application No. 61/538,124, filed on Sep. 22, 2011, provisional application No. 61/564,898, filed on Nov. 30, 2011, provisional application No. 61/650,625, filed on May 23, 2012.

(51) Int. Cl.
*A61L 9/00* (2006.01)
*B01D 45/00* (2006.01)
*A61L 2/26* (2006.01)

(52) U.S. Cl.
CPC .............. *A61L 2/26* (2013.01); *A61L 2202/123* (2013.01); *A61L 2202/14* (2013.01); *A61L 2202/16* (2013.01)
USPC .............................. 422/305; 422/306; 55/342

(58) Field of Classification Search
CPC .............. A61L 2/00; A61L 2/26; A61L 9/015; A61L 9/03; A61L 12/00
USPC ....... 134/582; 55/309, 342; 43/125; 422/1, 3, 422/28, 305–306
See application file for complete search history.

(56) References Cited

U.S. PATENT DOCUMENTS

2011/0027125 A1* 2/2011 Golkowski ...................... 422/29

* cited by examiner

*Primary Examiner* — Monzer R Chorbaji
(74) *Attorney, Agent, or Firm* — Williams Mullen, PC; Richard T. Matthews

(57) ABSTRACT

A portable gas transfer device for point-of-use sterilization at a sterilization site includes: a housing; a pressurized gas canister held by the housing; a first passageway in fluid communication with the pressurized gas canister and configured to supply pressurized pre-sterilization gas from the pressurized gas canister to the site; a gas discharge canister held by the housing; and a second passageway in fluid communication with the gas discharge canister and configured to supply post-sterilization gas from the site to the gas discharge canister. Additional related devices, systems and methods are provided.

33 Claims, 45 Drawing Sheets

DEVICES, SYSTEMS AND METHODS FOR LOCALIZED STERILIZATION

RELATED APPLICATIONS

This application claims priority to U.S. Provisional Patent Application No. 61/538,124, filed Sep. 22, 2011, to U.S. Provisional Patent Application No. 61/564,898, filed Nov. 30, 2011, and to U.S. Provisional Patent Application No. 61/650,625, filed May 23, 2012, the disclosures of which are incorporated by reference herein in their entireties.

FIELD OF THE INVENTION

This invention relates to devices, systems and methods for sterilization of components at and near point-of-use connection points, particularly in bioprocessing and biomanufacturing applications.

BACKGROUND

Today's market demand for new drugs, combined with the difficult economic climate, is challenging bioprocessors to review their manufacturing systems and seek ways to make them more flexible, reliable and cost effective. Increasingly, biomanufacturers are turning to single-use aseptic processing systems to meet or beat aggressive product introduction timeframes while controlling cost.

In the pharmaceutical fluid drug processing and manufacturing industry, there is a need for aseptic sterile conditions in the direct fluid product transfer path to minimize bacteria contamination, which results in contamination of the product batches at various stages of production. With the costs to manufacture a single drug approaching $1 billion and time-to-market ranging from 8 to 12 years, bioprocess manufacturers need to minimize all bio-burden contamination risk points in their process. By introducing a localized non-encumbering sterilization process at each process connection with optional sterilant level verification, the contamination risk concerns of bioprocess manufacturers would be addressed.

It is known to use localized steam sterilization, and steam sterilization is approved by the FDA. However, the use of steam suffers from several drawbacks. First, steam production has recurring costs. Also, there are thermal safety issues regarding the handling of steam by floor personnel. Moreover, concerns arise over the collection, recycling, or reprocessing of steam condensate after sterilization.

Ozone sterilization of medical and pharmaceutical devices has also been approved by the FDA. It is currently used on large scale batch sterilization of components used in sterile processing. However, small localized connector or small device "point-of-use" (POU) ozone sterilization is not known to be in use.

SUMMARY

Some embodiments of the invention are directed to a portable gas transfer device for point-of-use sterilization at a sterilization site. The device includes: a housing; a pressurized gas canister held by the housing; a first passageway in fluid communication with the pressurized gas canister and configured to supply pressurized pre-sterilization gas from the pressurized gas canister to the site; a gas discharge canister held by the housing; and a second passageway in fluid communication with the gas discharge canister and configured to supply post-sterilization gas from the site to the gas discharge canister.

In some embodiments, the device includes a sensor disposed in the second passageway upstream of the gas discharge canister, the sensor configured to detect a characteristic of the post-sterilization gas. The device may include at least one controller configured to receive a detection signal from the sensor and determine whether the site has been adequately sterilized based on the received detection signal. The controller may be configured to determine whether the site has been sterilized to a Sterility Assurance Level (SAL) of $10^{-6}$. The device may include at least one indicator on the housing to provide visual feedback that the site has been adequately sterilized based on a determination that the site has been adequately sterilized. The device may include a memory for storing data related to the received detection signal and/or the determination of whether the site has been adequately sterilized.

The pressurized pre-sterilization gas may be ozone. The detected characteristic may be an ozone level in the post-sterilization gas and the controller may be configured to determine whether the site has been adequately sterilized based on the ozone level over a period of time. The gas discharge canister may be a gas discharge catalyst canister including a catalyst material held therein, with the catalyst material configured to convert waste ozone in the post-sterilization gas to oxygen. The catalyst material may comprise manganese dioxide/copper oxide, activated charcoal or a molecular sieve. The device may include a vent on the housing for the expulsion of oxygen from the gas discharge catalyst canister.

In some embodiments, the device includes a gas fill port valve on the housing, with the gas fill port valve configured to receive pressurized gas from a recharging station to refill the pressurized gas canister. In some embodiments, the device includes an electrical interface on the housing, with the electrical interface configured to connect with an electrical connection to: recharge a battery pack of the portable gas transfer device; and/or transfer data to a database, including sterilization validation data.

Other embodiments of the invention are directed to a gas dispersion device. The device includes a housing and a gas flow member held in the housing. The housing defines a fluid flow path along an axis. The fluid flow path has first and second opposite ends. Each of the first and second ends is configured to operatively connect with at least one flow component. The gas flow member has an upper portion and a lower portion. The gas flow member includes a supply gas passageway extending from a gas supply port at the upper portion to first and second gas dispersion openings at the bottom portion. The gas flow member further includes first and second return gas passageways, with each return gas passageway extending from a return gas opening at the bottom portion to a return discharge port at the upper portion. The gas flow member is positionable in a sterilization position with the gas flow member lower portion disposed in the fluid flow path. In the sterilization position, the gas dispersion openings are configured to disperse pressurized pre-sterilization gas received from the gas supply port to sterilize flow components operatively connected with the first and second ends of the fluid flow path. In the sterilization position, the return gas discharge ports are configured to discharge post-sterilization gas received from the return gas openings. The gas dispersion device may be single-use disposable.

In some embodiments, the fluid flow path comprises a chamber and a pair of conduits extending away from the chamber, with each conduit including a flange at a distal end thereof, with the flanges defining the first and second ends of the fluid flow path. In some embodiments, at least one flow component is operatively connected with each of the first and second ends of the fluid flow path. The at least one flow component is at least one of a connector, a fitting, a flow passageway, a sensor and a transmitter. In some embodiments, in the sterilization position, the dispersion openings are configured to disperse gas received from the gas supply port around and/or past the flow components to achieve a Sterile Assurance Level (SAL) of $10^{-6}$ for the flow components. In some embodiments, in the sterilization position, the first and second gas dispersion openings are generally aligned with the axis.

The gas flow member may be movable between the sterilization position and a product flow position. In the product flow position, the lower portion of the gas flow member may be withdrawn out of the fluid flow path. In the product flow position, the fluid flow path may be configured to receive bioprocessing fluid flow therethrough. The lower portion of the gas flow member may include a seal configured to seal the fluid flow path. The device may include a locking mechanism to lock the device in product flow position.

In some embodiments, the device includes a shear key held in the housing and at least one shear cutter access port on the housing. The at least one shear cutter access port is configured to receive a shear cutter therethrough to cut the shear key. When the shear key is cut, the gas flow member moves from the sterilization position to the product flow position.

Other embodiments of the invention are directed to a system for sterilizing a process connection or joint. The system includes a gas dispersion device positioned in the process connection or joint and a portable gas transfer device. The gas dispersion device includes a housing defining a fluid flow path and a gas flow member held in the housing. The gas flow member has an upper portion and a lower portion disposed in the fluid flow path. The gas flow member includes a supply gas passageway extending from a gas supply port at the upper portion to at least one gas dispersion opening at the lower portion, and the gas flow member further includes at least one return gas passageway extending from a gas return opening at the lower portion to a gas discharge port at the upper portion. The portable gas transfer device includes: a supply gas canister containing pressurized gas; a gas discharge canister; and a gas transport member in fluid communication with the supply gas canister and the gas discharge canister, with the gas transport member held in a guided opening configured to receive the upper portion of the gas dispersion device. When the upper portion of the gas flow member is received in the guided opening, the portable gas transfer device is configured to: supply pre-sterilization pressurized gas from the supply gas canister to the at least one gas dispersion opening such that gas is dispersed in the fluid flow path to sterilize the process connection or joint; and receive post-sterilization gas in the gas discharge canister from the at least one gas return opening.

In some embodiments, when the upper portion of the gas flow member is received in the guided opening, the gas flow member and the gas transport member mate such that the supply gas passageway of the gas flow member is aligned with a supply passageway of the gas transport member and the at least one return gas passageway of the gas flow member is aligned with at least one discharge gas passageway of the gas transport member.

The portable gas transfer device may include: a gas sensor disposed in a passageway between the gas transport member and the gas discharge canister, with the sensor configured to detect a characteristic of the post-sterilization gas; and a controller configured to monitor the detected characteristic and validate that the process connection or joint has been sterilized based on detected characteristic. The portable gas transfer device may be configured to halt the supply of pre-sterilization gas to the gas dispersion device after validation that the process connection or joint has been sterilized. The portable gas transfer device may include an indicator to provide visual feedback after validation that the process connection or joint has been sterilized.

Other embodiments of the invention are directed to a sterilization gas supply and refilling system for portable gas transfer devices. The system includes a portable gas transfer device, a portable gas transfer device docking station and a gas supply manifold. The portable gas transfer device includes: a housing; a pressurized gas canister held by the housing, with the pressurized gas canister configured to supply pressurized pre-sterilization gas to a sterilization site; a gas discharge canister held by the housing, with the gas discharge canister configured to receive post-sterilization gas from the sterilization site; and a gas fill valve on the housing. The docking station includes a docking area configured to receive the portable gas transfer device, with the docking area including a gas supply connection for attachment with the portable gas transfer device fill valve. The gas supply manifold is configured to supply pressurized gas through the gas supply connection to the portable gas transfer device pressurized gas canister, thereby refilling the pressurized gas canister. The system may include a plurality of portable gas transfer devices and a plurality of docking areas, with each docking area configured to receive one of the gas transfer devices.

In some embodiments, the portable gas transfer device includes an electrical interface on the housing, and the docking area includes an electrical connection configured to: charge a battery pack of the portable gas transfer device; and receive data from memory of the portable gas transfer device, wherein the data includes sterilization validation data from at least one past sterilization event.

In some embodiments, the system includes a gas supply unit configured to supply pressurized gas to the gas supply manifold. The gas supply unit may include an ozone generation unit configured to generate ozone from an oxygen supply and/or a secondary gas supply. The system may include a gas catalytic converter in fluid communication with the gas supply manifold and the docking area, with the gas catalytic converter configured to: receive ozone gas that has been held in the portable gas transfer device and/or the gas supply manifold past a time limit; convert the received ozone gas to oxygen; and discharge the oxygen to atmosphere.

Other embodiments of the invention are directed to a method for sterilizing a bioprocessing connection or joint. The method includes: supplying pressurized ozone gas from a portable gas transfer device to the connection or joint; dispersing the pressurized ozone gas at the connection or joint; receiving at the portable gas transfer device post-sterilization gas supplied from the connection or joint; detecting the level of ozone in the received post-sterilization gas; and determining whether the connection or joint has been adequately sterilized based on the detected level of ozone.

In some embodiments, the method includes: positioning a gas dispersion device at the connection or joint; dispersing the pressurized ozone gas at the connection or joint using the gas dispersion device; and receiving at the portable gas transfer device post-sterilization gas supplied from the gas dispersion device. The gas dispersion device may include: a housing defining a fluid flow path; and a gas flow member held in the housing, the gas flow member having an upper portion and a lower portion, the gas flow member comprising a supply gas passageway extending from the top portion to first and second gas dispersion openings at the lower portion, the gas flow member further comprising first and second return gas passageways extending from the bottom portion to the top portion. The gas flow member may be movable between a sterilization position wherein the gas flow member lower portion is disposed in the fluid flow path and a product flow position wherein the lower portion is withdrawn from the fluid flow path. The method may include positioning the gas dispersion device at the connection or joint with the gas flow member in the sterilization position. The method may include: determining that the connection or joint has been adequately sterilized based on the detected level of ozone in the received post-sterilization gas; then moving the gas flow member to the product flow position; locking the gas flow member in the product flow position; and flowing bioprocessing fluid and/or material through the fluid flow path.

In some embodiments, the method includes: determining that the connection or joint has been adequately sterilized based on the detected level of ozone in the received post-sterilization gas; and halting the supply of pressurized ozone gas from a portable gas transfer device to the connection or joint. In some embodiments, the method includes determining whether a Sterility Assurance Level (SAL) of $10^{-6}$ has been achieved. In some embodiments, the method includes converting the received post-sterilization gas to oxygen at the portable gas transfer device.

Other embodiments of the invention are directed to a system including a sealable local environment and an ozone source operably coupled to the sealable local environment. The sealable local environment is configured to receive two or more fluid path members and to sealingly contain the two or more fluid path members. The sealable local environment is further configured to be manipulated to interconnect the two or more fluid path members within the sealable local environment while the sealable local environment remains sealed. The two or more fluid path members sealingly contained within the sealable local environment may be exposed to ozone to sterilize the two or more fluid path members prior to interconnecting the two or more fluid path members. In some embodiments, the sealable local environment includes a membrane configured to receive the ozone source, and the ozone source includes a syringe configured to inject ozone past the membrane. The sealable local environment may include a rigid structure configured to contain the two or more fluid path members, and the rigid structure may include an assembly chamber including one or more manipulators enabling the two or more fluid path members to be interconnected from outside the assembly chamber.

Other embodiments of the invention are directed to a system for point-of-use sterilization, including: a pressurized gas source; and a gas dispersion device. The gas dispersion device includes a housing defining a chamber; first and second flow conduits in fluid communication with the chamber, with each conduit extending away from the chamber, and with each conduit including a distal end portion configured to operatively connect with at least one fluid flow component; and a gas flow member held at least partially in the housing, with the gas flow member having a gas inlet port configured to operatively connect with the pressurized gas source and first and second dispersion openings in fluid communication with the gas inlet port. When the pressurized gas source is operatively connected with the gas inlet port, the dispersion openings are configured to disperse gas received from the pressurized gas source throughout the chamber and through the conduits to sterilize fluid flow components connected thereto.

In some embodiments, the pressurized gas source is a portable gas transfer device. In some embodiments, the pressurized gas source is or includes a syringe.

In some embodiments, the gas flow member includes a butterfly valve element. The butterfly valve element includes main faces and is adapted for rotational movement in the chamber between a closed position and an open position. The butterfly valve includes an inlet for introduction of gas, with the inlet communicating with a central gas dispersion opening extending transversely through a medial portion of the valve element for outward dispersion of gas at both main faces of the valve element. The butterfly valve element includes gas return ports at opposite marginal portions on opposite main faces of the butterfly valve element communicating with gas discharge ports at an end portion of the valve element.

In some embodiments, the gas flow member is movable between a sterilization position wherein the gas dispersion openings are disposed in the chamber and a product flow position, wherein the gas flow member is retracted from the chamber and/or rotated within the chamber to reach the product flow position.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

DETAILED DESCRIPTION

Figure 1:
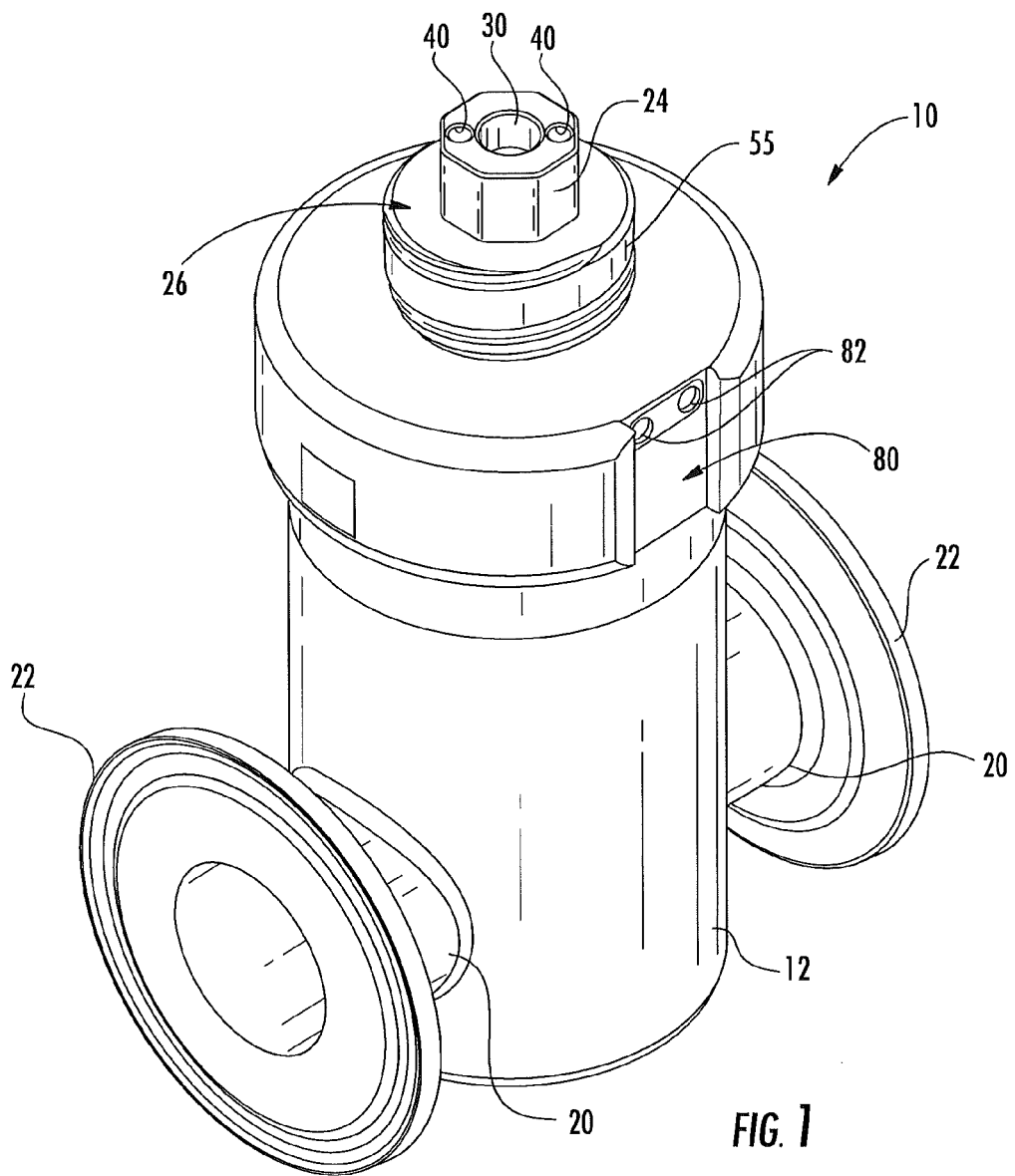
FIG. 1 is a top perspective view of a gas dispersion device according to some embodiments.

The present invention now will be described more fully with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. In the drawings, like numbers refer to like elements throughout. Thicknesses and dimensions of some components may be exaggerated for clarity.

As used herein, the term "comprising" or "comprises" is open-ended, and includes one or more stated features, integers, elements, steps, components or functions but does not preclude the presence or addition of one or more other features, integers, elements, steps, components, functions or groups thereof. As used herein, the term "and/or" includes any and all combinations of one or more of the associated listed items.

As used herein, the common abbreviation "e.g.," which derives from the Latin phrase "exempli gratia," may be used to introduce or specify a general example or examples of a previously mentioned item, and is not intended to be limiting of such item. If used herein, the common abbreviation "i.e.," which derives from the Latin phrase "id est," may be used to specify a particular item from a more general recitation.

The terminology used herein is for the purpose of describing particular embodiments only and is not intended to be limiting of the invention. As used herein, the singular forms "a," "an" and "the" are intended to include the plural forms as well, unless the context clearly indicates otherwise.

Well-known functions or constructions may not be described in detail for brevity and/or clarity.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In addition, spatially relative terms, such as "under," "below," "lower," "over," "upper," "downward," "upward," "inward, "outward" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

It will be understood that when an element is referred to as being "attached," "coupled" or "connected" to another element, it can be directly attached, coupled or connected to the other element or intervening elements may also be present. In contrast, when an element is referred to as being "directly attached," directly coupled" or "directly connected" to another element, there are no intervening elements present.

It is noted that any one or more aspects or features described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

As used herein, the terms "flow component" and "fluid flow component" mean a component that is attachable or operatively attachable to a gas dispersion device and/or to another fluid flow component that is in fluid communication with the gas dispersion device. Alternatively, the fluid flow component may be integrated with the gas dispersion device. The flow component has one or more interior surfaces that are to be exposed to product fluid, such as bioprocessing fluid. The interior surface(s) may include hidden and/or occluded areas. The gas dispersion device is configured to disperse gas around, into and/or through the fluid flow component such that the interior surfaces including the hidden/occluded areas are sterilized to a predetermined level (e.g., a Sterility Assurance Level of $10^{-6}$). Exemplary fluid flow components include, but are not limited to: connectors, fittings, fluid flow members such as tubes, sensors, transmitters and valves. The sterilization gas dispersed from the gas dispersion device may flow past or through the flow component (e.g., in the case of certain fittings and fluid flow members) or may flow adjacent or around the flow component (e.g., in the case of certain sensors and transmitters).

The gas dispersion devices of the present invention effectively sterilize the fluid flow members, which may be located at or near process connections or joints. The gas dispersion devices may be disposed at these connections or joints to effectively sterilize the connection/joint and/or any nearby or attached fluid flow component. It will be understood that any of the fluid flow components described above (e.g., connectors, fittings, sensors, transmitters, etc.) may be disposed at or near (or integrated with) a "process connection or joint" as the term is used herein.

Figure 4:
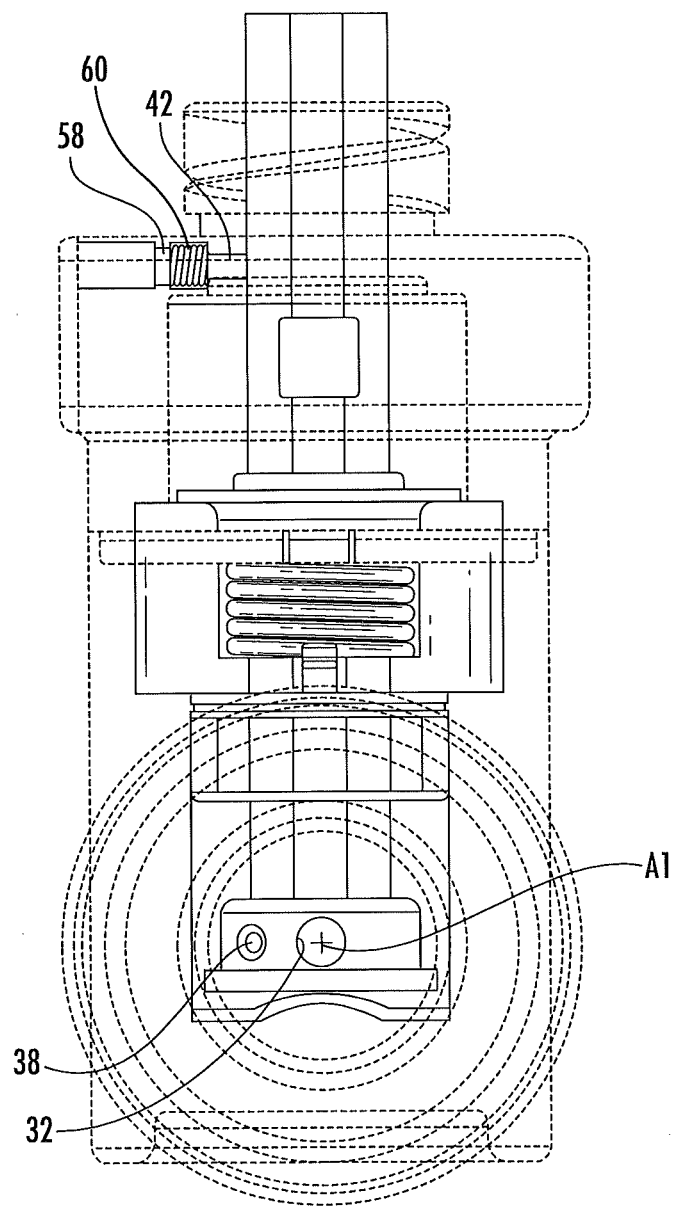
FIG. 4 a partially transparent end view of the device of FIG. 1.
Figure 5:
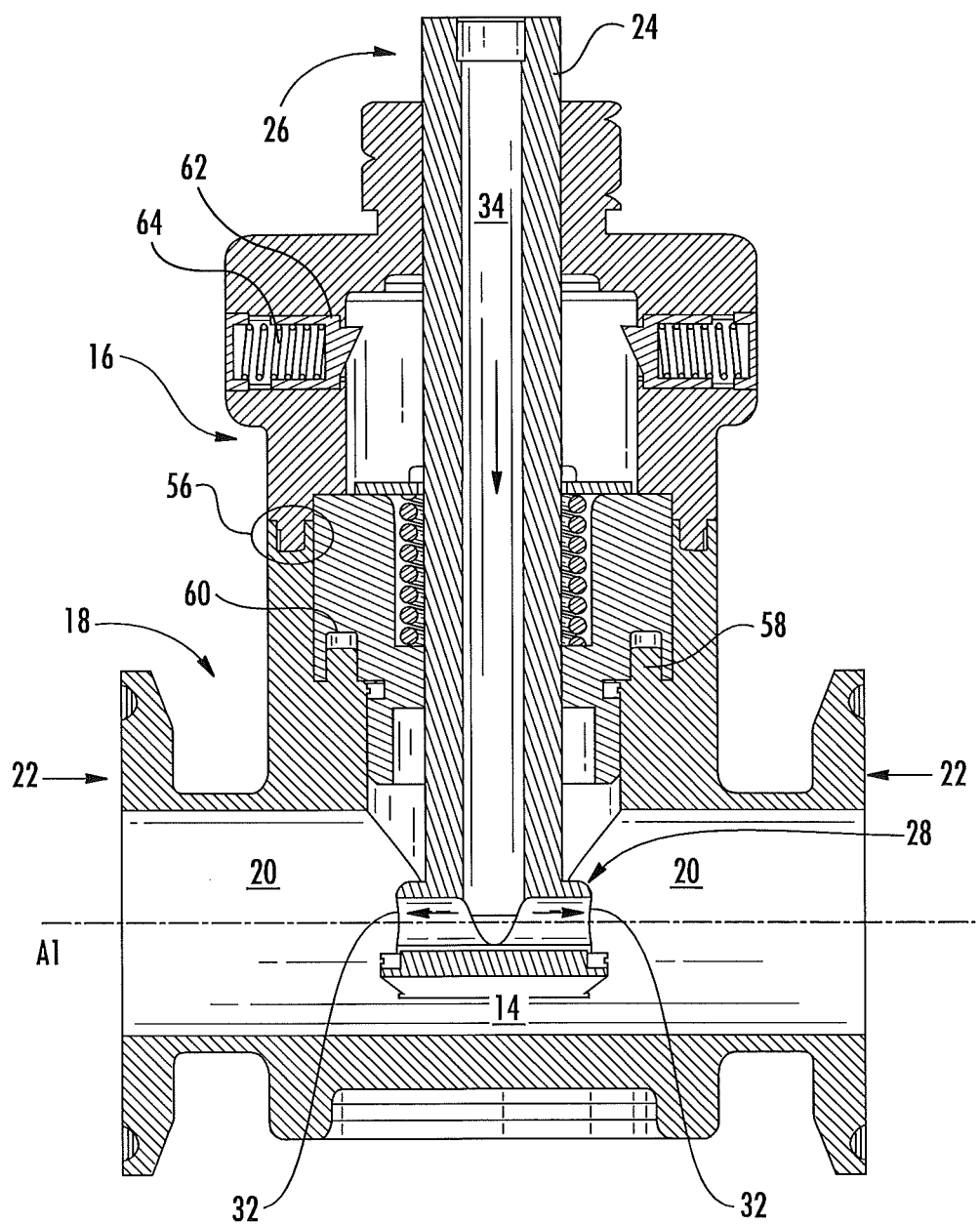
FIG. 5 is a cross-sectional side view of the device of FIG. 1.

A gas dispersion interconnect device 10 according to some embodiments is illustrated in FIGS. 1-8. The gas dispersion device 10 includes a housing 12. At least a portion of the housing 12 defines an internal cavity or chamber 14. The housing 12 includes an upper portion 16 and a lower portion 18. As illustrated, the chamber 14 is defined in the lower portion 18 of the housing 12 (FIG. 5).

Figure 7:
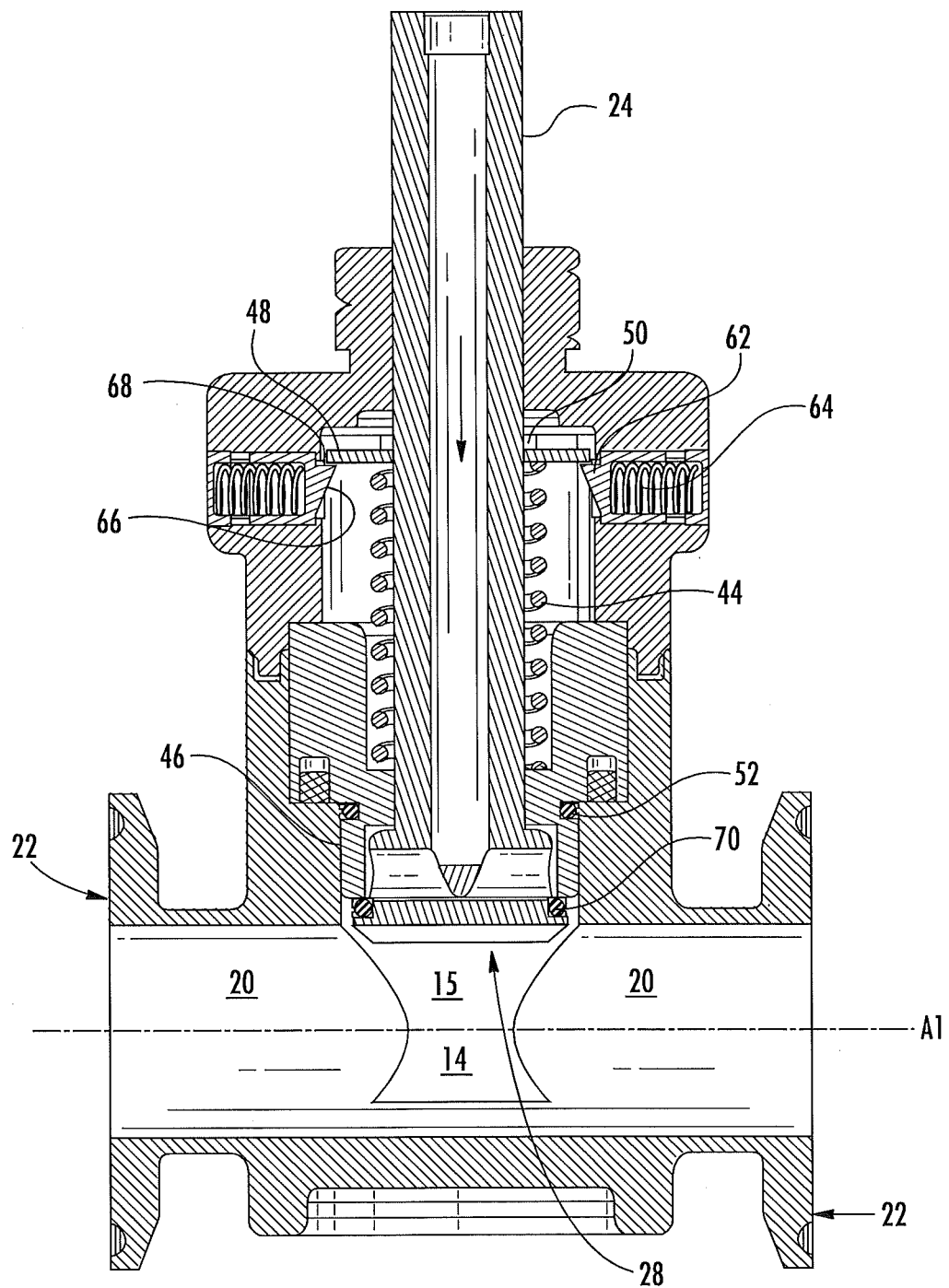
FIG. 7 is a cross-sectional side view of the device of FIG. 1 in a post-sterilization or product flow position.
Figure 8:
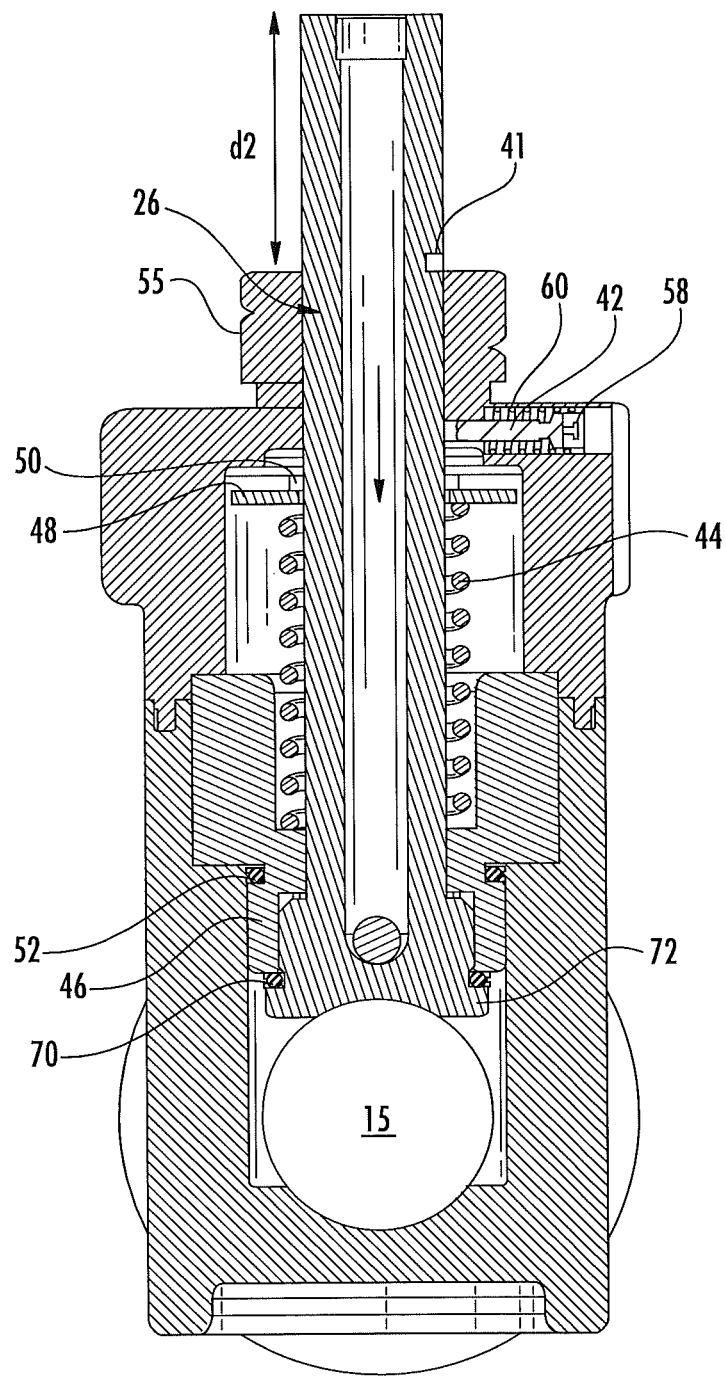
FIG. 8 is a cross-sectional end view of the device of FIG. 1 in a post-sterilization or product flow position.

First and second flow conduits 20 are in fluid communication with and extend outwardly away from the chamber 14. As illustrated in FIG. 5, the first and second conduits 20 are diametrically opposed and extend away from the chamber along an axis A1. The chamber 14 and the conduits 20 may be collectively referred to as a fluid flow path 15 (FIGS. 7 and 8). A distal end portion of each conduit 20 includes a flange 22 configured to connect or operatively connect to a fluid flow component (for example, via a sanitary clamp). As will be described in detail below, the gas dispersion device 10 is configured to disperse pressurized gas to sterilize the fluid flow components connected thereto.

The gas dispersion device 10 includes an elongated gas flow member 24. The gas flow member 24 has an upper portion 26 and a lower portion 28. The gas flow member upper portion 26 includes a gas supply/inlet port or opening 30 and the gas flow member lower portion 28 includes first and second gas dispersion openings 32. A gas inflow or supply passageway 34 extends between the inlet port 30 and the gas dispersion openings 32.

Figure 2:
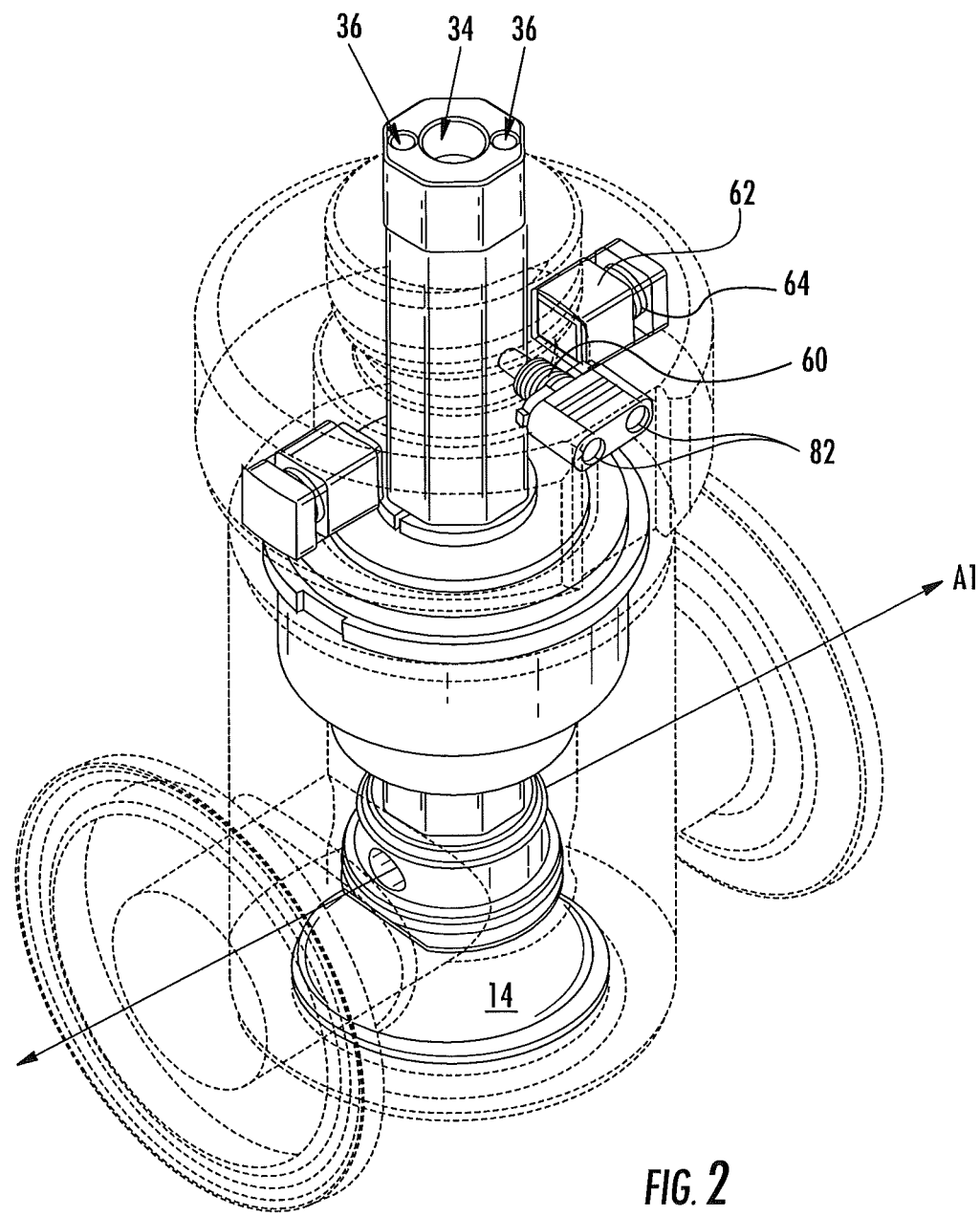
FIG. 2 is a partially transparent top perspective view of the device of FIG. 1.
Figure 3:
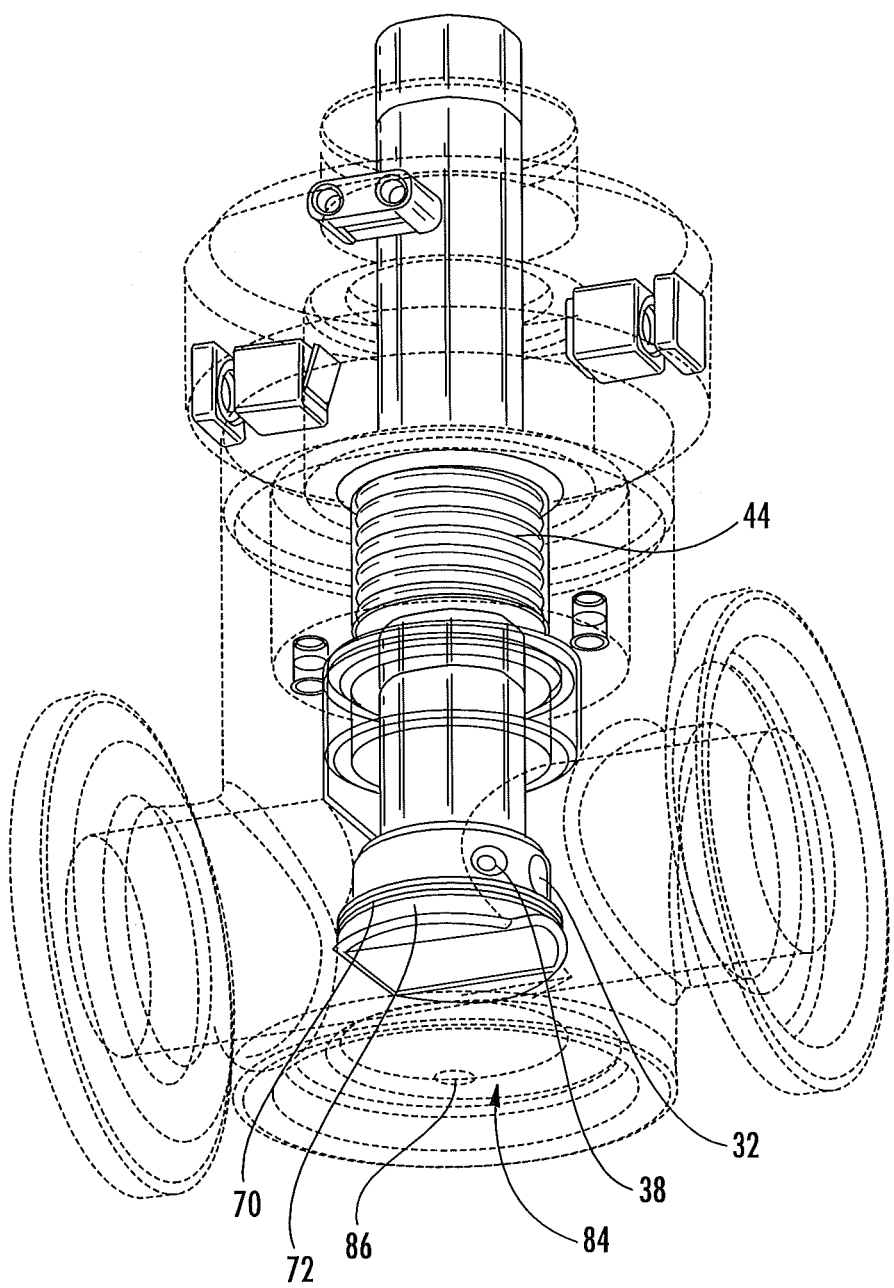
FIG. 3 is a partially transparent bottom perspective view of the device of FIG. 1.

The gas flow member 24 includes first and second gas return passageways 36 (FIG. 2). Each gas return passageway 36 extends between a gas return opening or port 38 at the gas flow member lower portion 28 (FIGS. 3 and 4) and a gas discharge opening or port 40 at the gas flow member upper portion 26 (FIG. 1).

The gas flow member 24 is positionable in a sterilization position, as illustrated in FIGS. 1-6. In the sterilization position, the gas flow member lower portion 28 is disposed in the chamber 14 or the fluid flow path 15. In this regard, the gas dispersion openings 32 are positioned and configured to effectively and rapidly disperse pressurized gas received from the gas inlet port 30 through the conduits 20 and adjacent and/or past fluid flow components attached to the flanges 22. In some embodiments, the gas dispersion openings 32 are generally or substantially aligned with the axis A1 in the sterilization position (FIGS. 2 and 4). It will be understood that, in use, the device 10 may be positioned such that the axis A1 is defined as a longitudinal (horizontal) axis, a latitudinal (vertical) axis or any angle or axis therebetween.

In the sterilization position, the gas return openings or ports 38 are also disposed in the chamber 14 or the fluid flow path 15. As illustrated, the gas return openings 38 may be offset from the axis A1 (FIG. 4).

Figure 6:
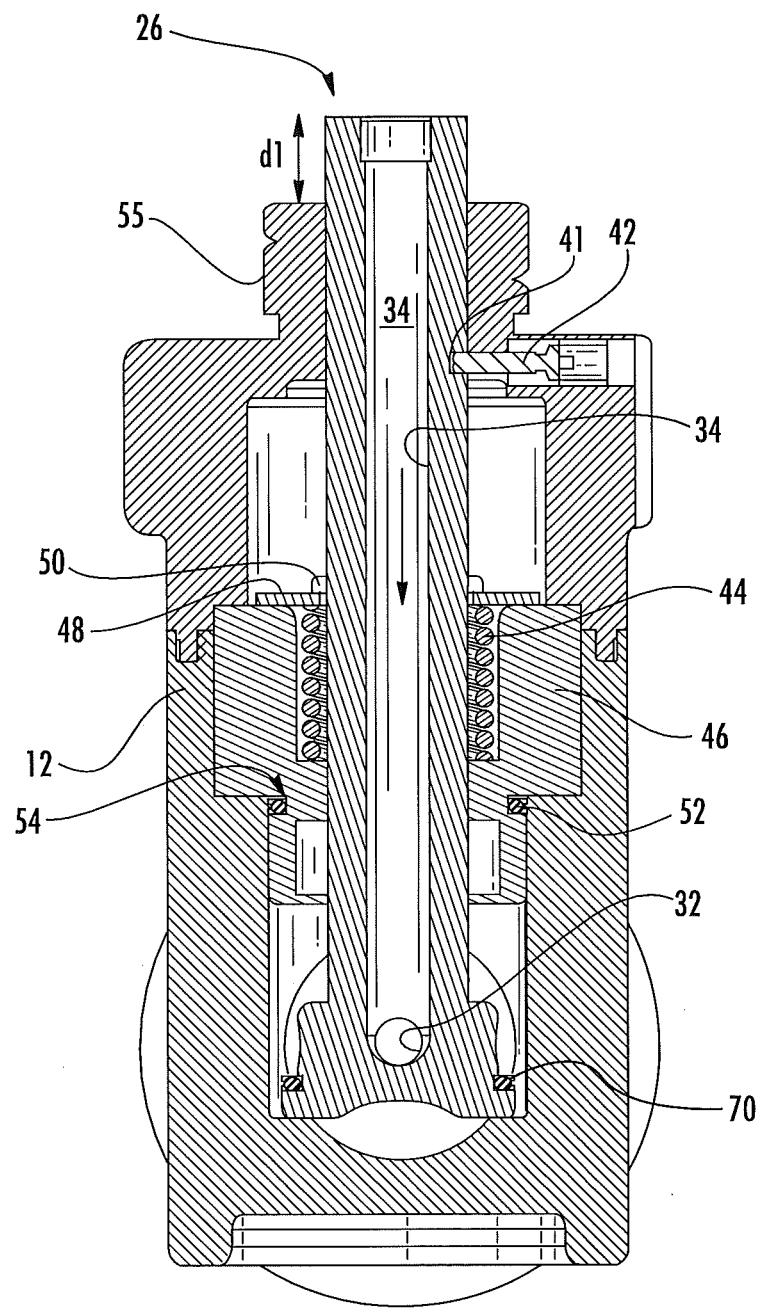
FIG. 6 is a cross-sectional end view of the device of FIG. 1.

The gas dispersion device 10 may be temporarily locked in the sterilization position via a locking mechanism. As shown in FIG. 6, an opening 41 extends inwardly from an outer surface of the gas flow member 24, and a pin 42 is received in the opening 41 to retain the gas flow member 24 in the sterilization position. The pin 42 is part of a "shear key assembly" described in more detail below.

Also as shown in FIG. 6, the gas dispersion device 10 includes a main actuator spring 44. In the sterilization position, the spring 44 is held within a main actuator spring containment body 46; the spring containment body 46 is disposed within the housing 12. A flat washer 48 is positioned above the spring 44 and a retaining ring 50 is positioned above the washer 48. At least one of the washer 48 and the retaining ring 50 is attached to the outer surface of the gas flow member 24. In the sterilization position, the spring 44 is compressed and held in place by the washer 48 and the retaining ring 50.

Still referring to FIG. 6, a first annular seal 52 is provided in a groove 54 of the spring containment body 46. The seal 52 inhibits the passage of pre- and post-sterilization gas as well as bioprocessing fluid/material that flows through the fluid flow path after sterilization has taken place.

Again, in the sterilization position, the gas dispersion device 10 is configured to rapidly disperse gas from the gas dispersion openings 32. The gas is dispersed throughout the chamber 14, through the conduits 20, and adjacent and/or past flow components attached to the flanges 22, thereby efficiently sterilizing these components. The gas is received from a pressurized gas source through the gas supply port 30 and flows through the gas inflow passageway 34 before being dispersed from the gas dispersion openings 32. As will be described in more detail below, the pressurized gas source may be received on a collar 55 (FIG. 1) at the top portion of the housing 12.

In some embodiments, the housing 12 is a one-piece housing. In some embodiments, the housing upper portion 16 and the housing lower portion 18 are discrete components. This may accommodate the placement of the spring containment body 46 within the housing 12. As illustrated in FIG. 5, the housing lower portion 18 may include at least one locating guide pin 58 and the spring containment body 46 may include at least one opening 60 sized and configured to receive the at least one guide pin 58. There may be a plurality of guide pins 58 and openings 60 or the guide pin 58 may be an annular or semi-annular protrusion and the opening 60 may be a corresponding annular or semi-annular groove. The housing upper and lower portions 16, 18 may be welded (e.g., ultrasonically welded) at joint 56. In some embodiments, most or all of the components of the gas dispersion device 10 are formed of an inert polymer. In some embodiments, the spring 44, the washer 48 and/or the retaining ring 50 are formed of a metallic material such as stainless steel.

The gas dispersion device 10 is movable between the sterilization position, described above, and a post-sterilization or product flow position, as illustrated in FIGS. 7 and 8. In the product flow position, the gas flow member lower portion 28 is withdrawn from the chamber 14 after flow components attached to the flanges 22 have been adequately sterilized. With the gas flow member 24 withdrawn from the chamber 14, the chamber 14 and the conduits 20 define an open flow path 15 (e.g., along the axis A1). The open flow path provides a low resistance path for product, such as bioprocessing fluid/material, to flow, including along or past flow components attached to the flanges 22 that were sterilized when the gas dispersion device 10 was in the sterilization position.

As illustrated in FIG. 8, the movement from the sterilization position to the product flow position is initiated by cutting a shear key 58; the process for cutting the shear key 58 will be described in more detail below. According to some embodiments, the shear key 58 comprises a brittle ceramic or polymeric material that crumbles, shatters or otherwise fractures when cut. In some embodiments, the shear key is made of brittle polystyrene. After the shear key 58 is cut, previously compressed spring 60 expands and retaining pin 42 retracts away from the gas flow member 24 and clear of the opening 41 therein. At this point, previously compressed spring 44 expands and forces the washer 48 and the retaining ring 50 upward, and in turn forces the gas flow member 24 upward.

The gas dispersion device 10 may include a locking mechanism to lock the gas dispersion device 10 or the gas flow member 24 in the product flow position. In the illustrated embodiment, first and second post-sterilization locking cams 62 are disposed in the housing upper portion 16. A spring 64 biases each cam 62 inwardly toward the gas flow member 24. Each cam 62 has a side surface 66 that tapers inwardly from bottom to top. Each cam 62 also has a flat or substantially flat top surface 68. As noted above, the spring 44 forces the washer 48 and/or the retaining ring 50 upwardly after the pin 42 becomes disengaged with the opening 41 in the gas flow member 24. As the washer 48 travels upwardly, the washer 48 engages the cam side surface 66 and compresses the spring 64 such that the washer 48 can extend upwardly past the top portion of the cam side surface 66. After the washer 48 has cleared the top portion of the cam side surface 66, the spring 64 urges the cam 62 inwardly such that the washer 48 may rest on the cam top surface 68. The gas dispersion device 10 or the gas flow member 24 is now locked in place in the post-sterilization or product flow position.

The gas flow member lower portion 28 includes a second seal 70. The second seal 70 may take the form of an annular seal or o-ring positioned below the gas dispersion openings 32. For example, as shown in FIG. 8, the gas flow member lower portion 28 may include a seat 72 on which the second seal 70 may be positioned, with the seal positioned below the gas dispersion openings 32 and the return gas flow ports 38.

As illustrated in FIGS. 7 and 8, in the product flow position, the second seal 70 is brought into contact with a lower portion of the spring containment body 46. In this regard, a "double seal" is provided with the first and second seals 52, 70 to inhibit upward flow of bioprocessing or product fluid/material that flows through the fluid flow pathway 15.

Referring back to FIG. 6, in the sterilization position, the gas flow member 24 (or the upper portion 26 thereof) extends a first distance d1 from a top portion of the threaded collar 55. As shown in FIG. 8, in the post-sterilization or product flow position, the gas flow member 24 (or the upper portion 26 thereof) extends a second distance d2 from a top portion of the threaded collar 55, with the second distance d2 being greater than the first distance d1. In some embodiments, the second distance d2 is less than about 1 inch greater than the first distance d1. In some embodiments, the second distance d2 is between about 0.5 and about 0.75 inches greater than the first distance d1. The difference between the distances d2 and d1 represents the amount of upward travel of the gas flow member 24 between the sterilization position and the product flow position.

Referring again to FIG. 3, a bottom portion of the gas dispersion device 10 may include a well 84 (i.e., below the chamber 14). The well 84 may be used to accommodate a sensor/transmitter to be attached or integrated to the gas dispersion device 10. The well 84 may be of varying size depending on the size or type of sensor/transmitter to be accommodated. Where used, a through-hole 86 provides fluid communication for a probe or the like of the sensor/transmitter. The through-hole 86 may also be of varying size depending on the application.

The gas interconnect dispersion device 10 may be employed to efficiently disperse low-temperature gases/vapors for localized sterilization of fluid flow components at point-of-use connection sites. As described above, the fluid flow components (including connectors, fittings, fluid flow paths such as tubing and the like, sensors and/or transmitters) may be connected or operatively connected to the conduits 20 or the flanges 22 of the gas dispersion device 10.

Current technology employs "pre-sterilized" flow components such as connectors, fittings, fluid flow paths, sensors/transmitters and the like. However, during the process of connecting such flow components to a drug manufacturing or processing system, the sterile connectors, fittings and sensors/transmitters are often exposed to an ambient non-sterile atmosphere that has the potential to cause microbial contamination. The gas dispersion interconnect device 10 helps ensure that after a "pre-sterilized" aseptic flow component is exposed to an ambient non-sterile atmosphere, any residual microbial contamination can be reduced to the necessary level.

Low-temperature gas/vapor sterilants include: ozone gas, ethylene oxide (EO or EtO), vaporized hydrogen peroxide (VHP or HPV), hydrogen peroxide gas plasma, vaporized formaldehyde, gaseous chlorine dioxide and vaporized peracetic acid.

Pressurized ozone gas may be advantageously used because it is an efficient FDA-approved sterilant, because it leaves no residual surface coatings, because it is safe and inexpensive to produce, because of its low pressure handling characteristics and/or because it is easily reverted back to oxygen using a chemical catalyst. While the discussion herein largely focuses on the use of ozone gas as the sterilant, it will be appreciated that other low-temperature gases/vapors, such as those listed above, may be employed.

As pressurized ozone gas dispersed by the gas dispersion device 10 migrates through joints or process connections joined by the dispersion device 10 and/or flow components operatively connected to the gas dispersion device 10, it sterilizes all internal surfaces, including occluded or hidden areas of the flow components where bacteria or microbial populations can grow, to achieve a Sterility Assurance Level (SAL) of $10^{-6}$ as mandated by the FDA. That is, the gas dispersion device 10 can effectively sterilize connected or operatively connected connectors, fittings, fluid flow paths, sensors and/or transmitters including occluded portions thereof to a SAL of $10^{-6}$. The gas dispersion device 10 may effectively disperse the gas to sterilize further downstream areas, including downstream occluded areas, as well.

The gas dispersion interconnect device 10 is typically "single-use" and can be used to sterilize connection points in the fluid product transfer path in drug processing and manufacturing systems, for example. In addition, the gas interconnect device 10 can be used to sterilize single-use and reusable aseptic disposable sensors/transmitters, as described below.

Sensors/transmitters can be integrated with and mounted to the gas dispersion device 10. Thus, the present invention contemplates the integration and mounting of various types of single-use or reusable sensors and transmitters into a drug manufacturing system, and their subsequent sterilization using ozone gas at the point-of-use (POU) connection point. The types of sensors and transmitters that may be sterilized include, but are not limited to: pressure sensors and transmitters, flow rate sensors and transmitters, temperature sensors and transmitters, $CO_2$ sensors and transmitters, $O_2$ sensors and transmitters, pH sensors and transmitters, conductivity sensors and transmitters and redox and O.R.P. sensors and transmitters. By exposing the sensor mounting at aseptic connection points to a calculated concentration of ozone gas, the majority of the microbial population is killed to achieve a SAL of $10^{-6}$.

According to some embodiments, a sensor/transmitter mounting and fitting assembly includes a single-use or reusable sensor/transmitter, a single-use mounting fitting and an ozone gas dispersion sterilization device, such as the device 10 described above. Two or more of the sensor/transmitter mounting and fitting assemblies may be integrated to form an integrated, single-use assembly.

Figure 9:
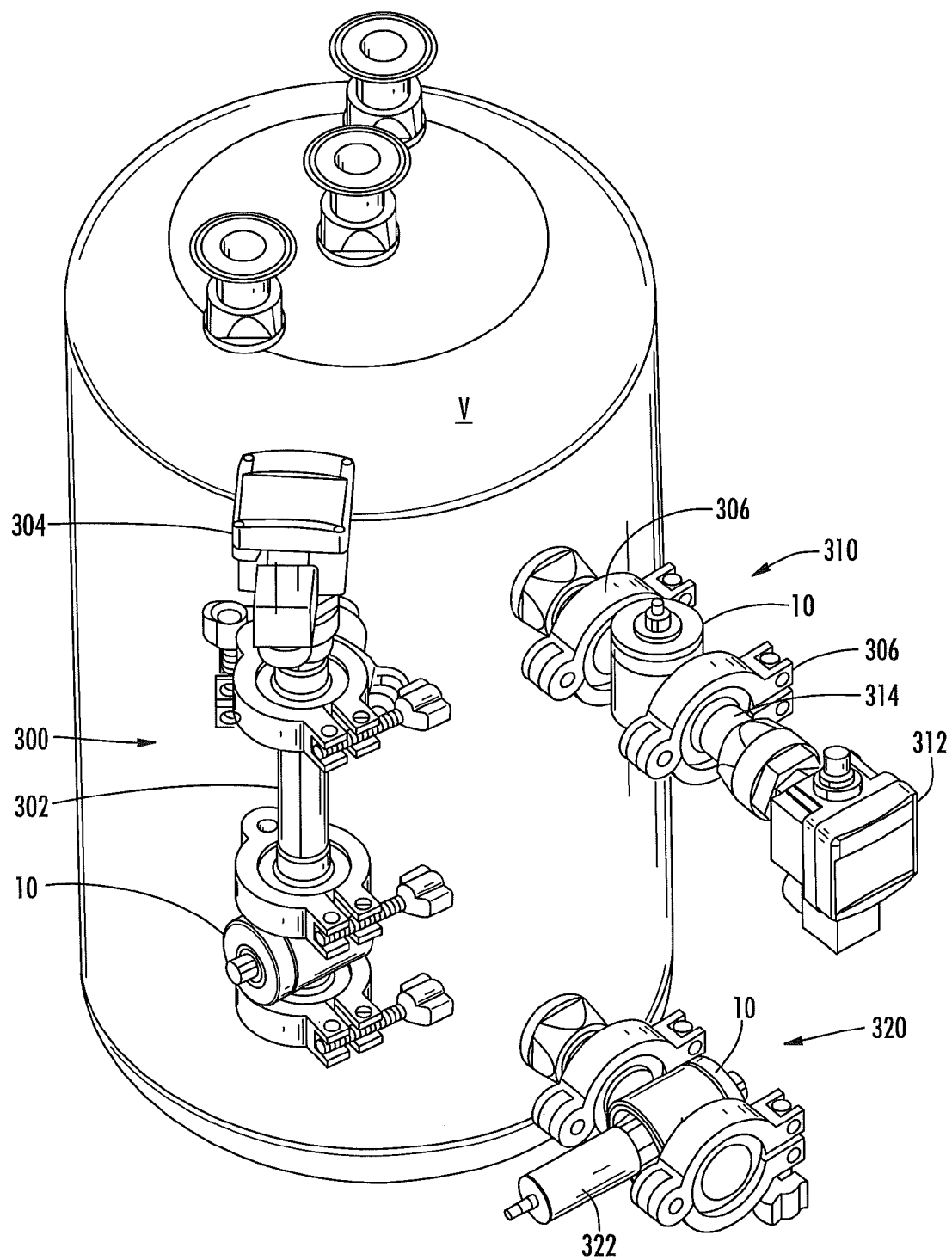
FIG. 9 is a schematic view illustrating various exemplary sensor/transmitter mounting configurations to point-of-use connection points and employing the device of FIG. 1.
Figure 10:
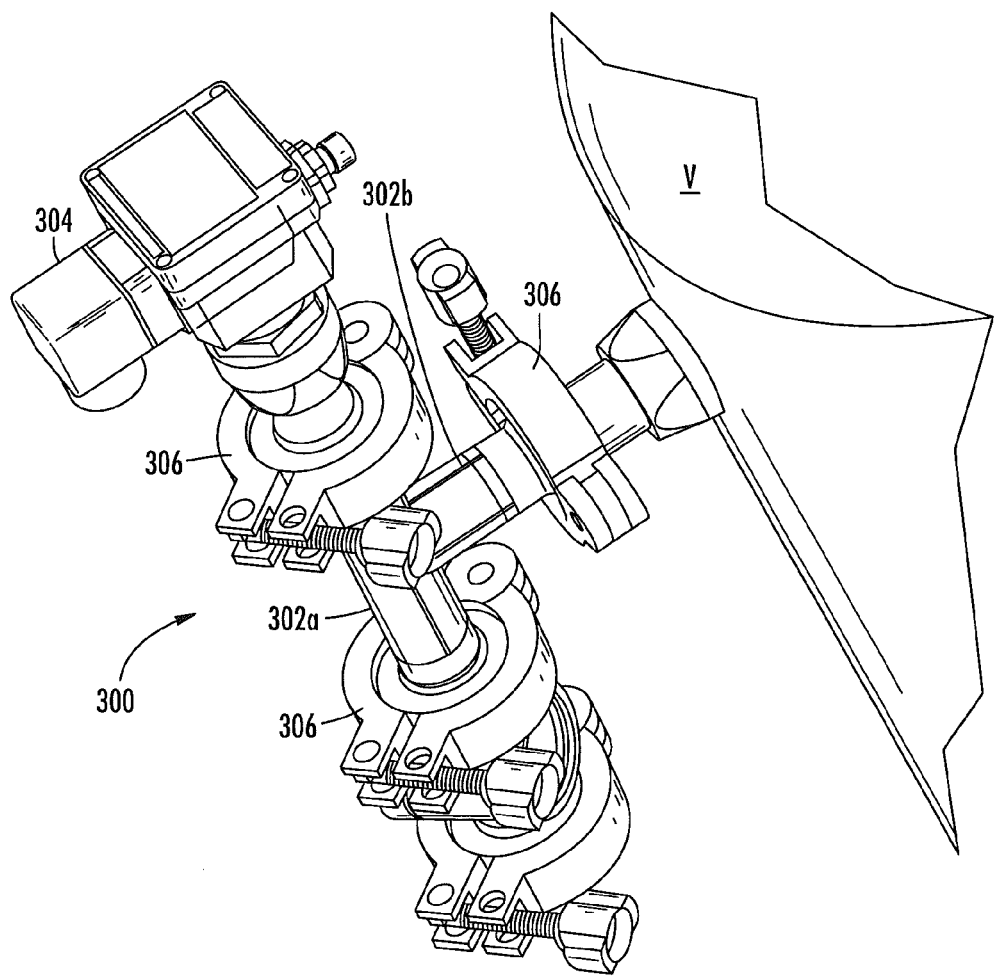
FIG. 10 is an enlarged schematic view illustrating one of the exemplary sensor/transmitter mounting configurations of FIG. 9.
Figure 11:
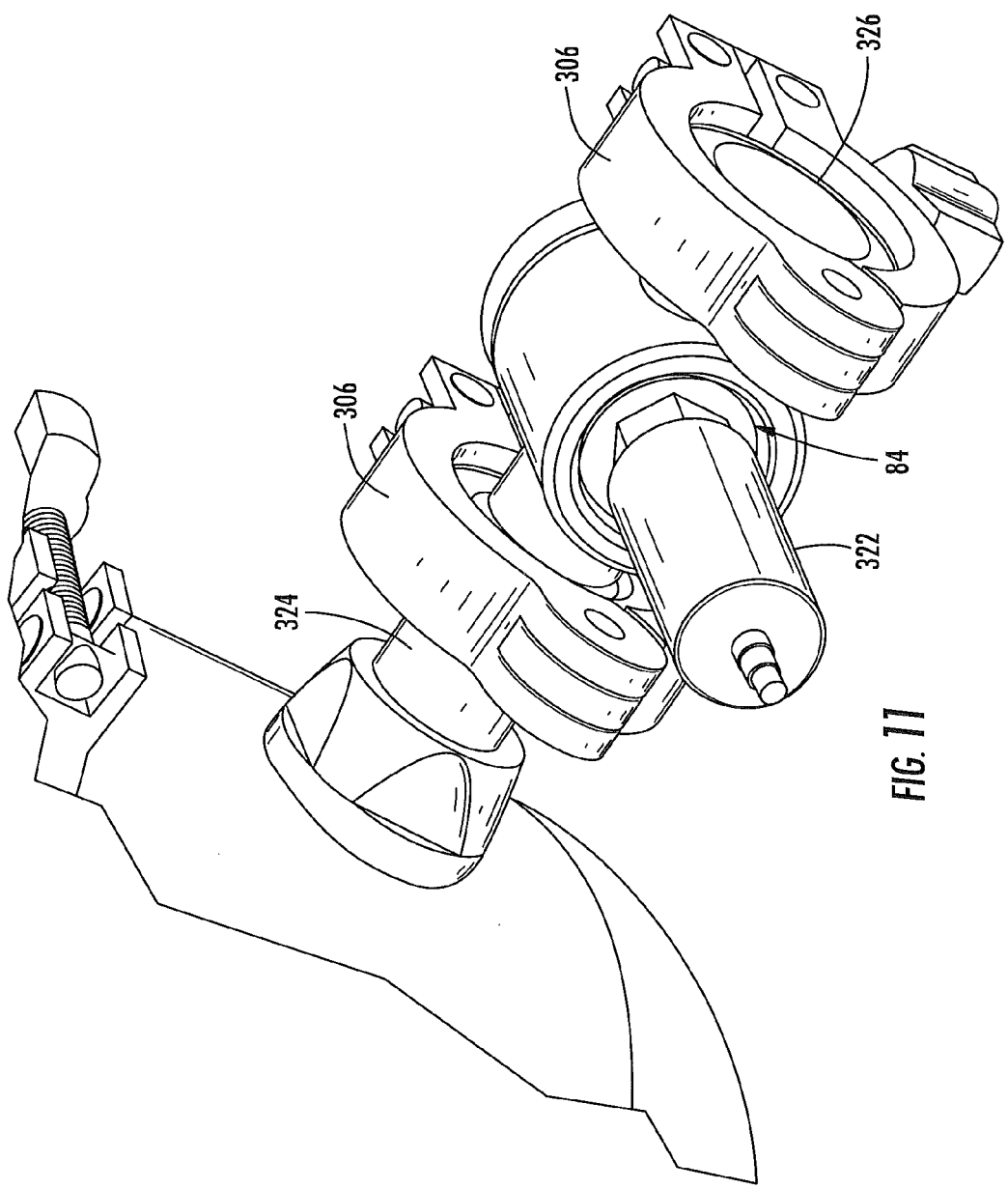
FIG. 11 is an enlarged schematic view illustrating one of the exemplary sensor/transmitter mounting configurations of FIG. 9.

Exemplary embodiments of such assemblies are shown in FIGS. 9-11. Three exemplary configurations are illustrated together in FIG. 9. As best shown in FIGS. 9 and 10, a first configuration 300 includes the gas dispersion sterilization device 10, a mounting fitting 302 and a long probe sensor/transmitter 304. The fitting 302 is T-shaped and includes a first run portion 302a extending between first and second ends and a second run portion 302b extending outwardly from the first run portion 302a.

The first end of the first run 302a is operatively connected to one of the conduits 20 (or one of flanges 22) the gas dispersion device 10 via a sanitary clamp 306. The opposite end of the first run 302a is operatively connected to the sensor/transmitter 304 via another sanitary clamp 306. The length of the first run 302a can be selected to accommodate the length of the long probe sensor 304. In some embodiments, the length of the first run 302a is selected to accommodate sensor probes having lengths of 9-10 inches or greater.

The second run 302b of the fitting 302 is operatively connected to a vessel V (such as a bioreactor) via another sanitary clamp 306. This connection point is adjacent an isolation valve associated with the bioreactor or product vessel V. The isolation valve is movable between open and closed positions.

With the isolation valve in the closed position, a pressurized ozone gas source, such as a syringe or a hand-held or portable ozone gas supply canister (described in detail below), is provided. The portable ozone gas supply canister is configured to connect with the gas flow member top portion 26 of the gas dispersion device 10 and supply pressurized ozone through the gas inlet port 30 (FIG. 1), thereby effectively and rapidly dispersing the ozone gas through the dispersion openings, as described above. All internal cavities and components including the sensor/transmitter 304, mounting fitting 302 and other attached components are exposed to the ozone gas and sterilized to the requisite SAL of $10^{-6}$. As will be described below, excessive amounts of "post-sterilization" ozone gas will be passed through the gas outlet ports 40 of the gas dispersion device 10 and through a catalytic filter associated with the portable ozone canister to convert the waste ozone gas to oxygen before it reenters the atmosphere. Also as described below, the "post-sterilization" gas may be monitored and analyzed before or during the conversion process to ensure that the required log 6 reduction of microbial species has occurred; the portable ozone gas supply canister includes the catalytic device and a measuring and/or monitoring device to measure and/or indicate that an SAL of $10^{-6}$ has been achieved with respect to components connected or operatively connected to the gas dispersion device 10.

Referring to FIG. 9, a second exemplary configuration 310 is shown. An in-line sensor/transmitter 312 and a mounting fitting 314 are operatively connected to one of the conduits or flanges 20, 22 of the gas dispersion device 10 via a sanitary clamp 306. The other one of the conduits or flanges 20, 22 of the gas dispersion device 10 is operatively connected to the vessel V. Thus, an in-line sensor/transmitter mounting assembly is formed. In the manner described above, an isolation valve associated with the vessel V is closed, and a portable ozone gas supply canister is attached to the gas dispersion device 10. All internal cavities including the sensor/transmitter 312, mounting fitting 314 and other attached components are exposed to the ozone gas and sterilized to the requisite SAL of $10^{-6}$.

A third exemplary configuration 320 is shown in FIGS. 9 and 11. Here, the gas dispersion device 10 is configured to receive the sensor/transmitter 322 via the well 84, thereby forming a direct sensor/transmitter mounting configuration. One of the flanges 22 of the gas dispersion device 10 is operatively connected to the vessel V via a fitting 324 and a sanitary clamp 306. Again, an isolation valve associated with the vessel V is closed, and a portable ozone gas supply canister is attached to the gas dispersion device. All internal cavities including the sensor/transmitter 322 and the fitting 324 and other attached or nearby components are exposed to the ozone gas and sterilized to the requisite SAL of $10^{-6}$.

In the third configuration 320, a sanitary clamp 306 connects the other one of the flanges 22 of the gas dispersion device 10 with a flow blocking member 326. It is contemplated that the gas dispersion device 10 may alternatively be formed or manufactured with a closed conduit, or with no conduit at this location (e.g., the gas dispersion device 10 includes only one conduit 20). Further, it is noted that, in place of the flow blocking member 326, a fluid flow path such as a fitting or a tube could be connected to the flange 22 via the sanitary clamp 306. The fluid flow path may be connected to another container or vessel, for example. In this configuration, the gas dispersion device 10 would be configured to further sterilize this additional fluid flow path running to the other container or vessel.

For all of the above-described configurations, all or some of the gas dispersion device, the sensor/transmitter and any associated mounting fittings or flow components may be integrated so as to form a single-use disposable assembly that may be integrated to the bioprocessing system. The above described sterilization/product flow processes may take place, after which point the entire integrated assembly is removed and the vessel is cleaned around the isolation valve area. It is noted that the vessel may also be single-use disposable and, in some embodiments, may also be integrated with the assembly.

As discussed above, the gas dispersion device 10 is configured to receive pressurized gas through the gas supply port 30 from a pressurized gas supply source. Various pressurized gas sources, such as a syringe or the like, are contemplated as described below. One such source is included in the portable gas canister assembly or portable gas transfer device 100 shown in FIGS. 12-27. The device 100 includes a housing 101 having an upper portion 102 and a lower portion 104. A carry handle 106 may be provided between the housing upper and lower portions 102, 104. The device 100 includes a gas supply canister 108 and a gas discharge canister or gas discharge catalyst canister 110. As illustrated, the gas supply canister 108 and the gas discharge catalyst canister 110 may each extend between the housing upper and lower portions 102, 104. One or more support columns 112 may also extend between the housing upper and lower portions 102, 104 to provide strength. According to some embodiments, the canisters 108, 110 are metallic. According to some embodiments, the gas supply canister 108 is nickel plated aluminum. According to some embodiments, the gas discharge catalyst canister 110 is stainless steel. According to some embodiments, the gas supply canister 108 has an internal volume of about 0.5 liters. According to some embodiments, the gas supply canister is configured to hold ozone at a pressure of about 100 psig.

Disposed on the housing upper portion 102 are a plurality of status indicator lights 114, a display 116 and an operator interface 118. Also disposed on the housing upper portion 102 is a gas discharge vent 120. The vent 120 is in fluid communication with the gas discharge catalyst canister 110. The functionality of these components will be described below.

Figure 13:
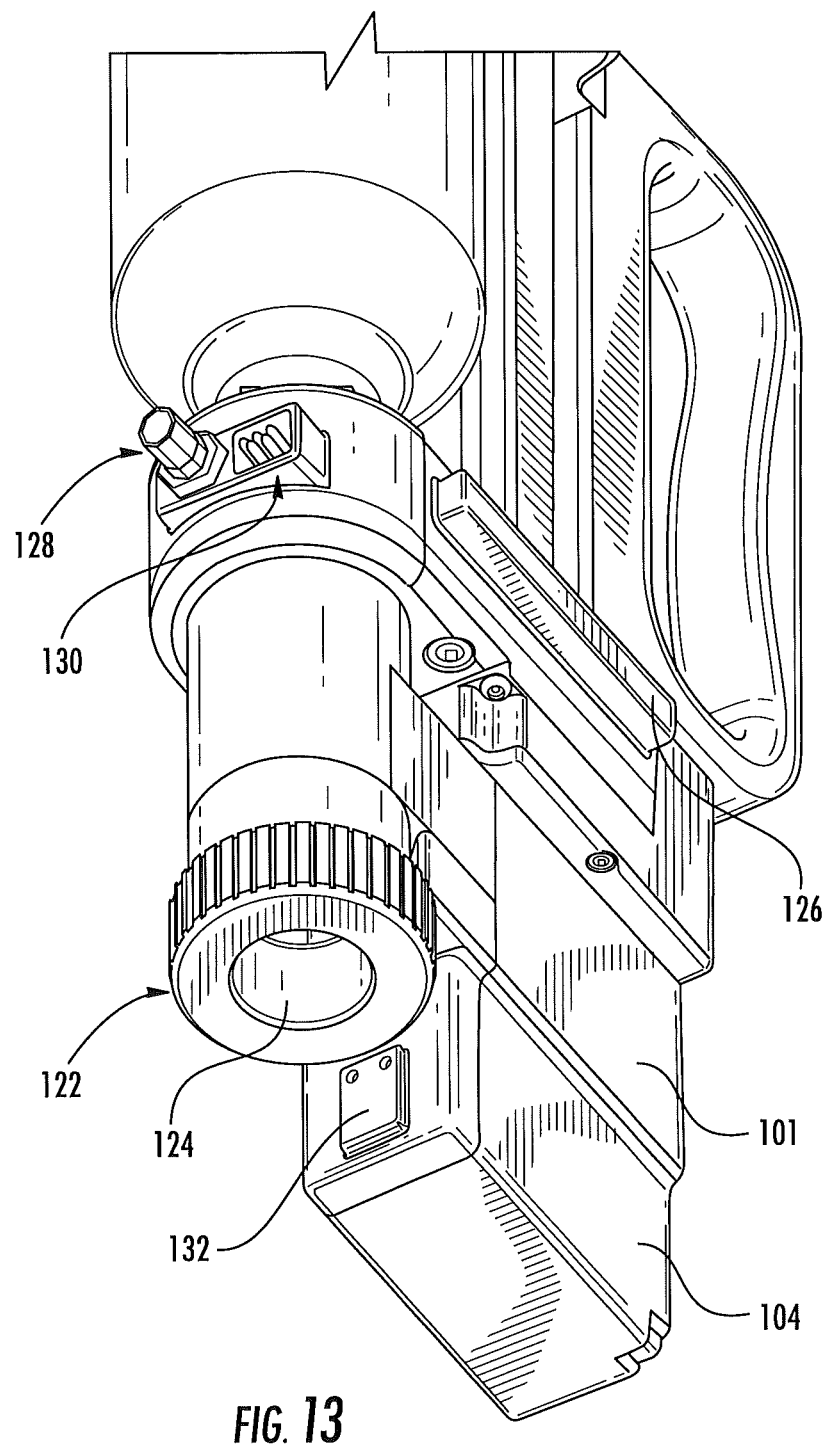
FIG. 13 is an enlarged bottom perspective view of the portable gas transfer device of FIG. 12.

Attached to the housing lower portion 104 is a mounting nut 122. Referring to FIG. 13, the mounting nut 122 includes an opening 124 sized and configured to receive therethrough the gas flow member 24 of the gas dispersion device 10. The mounting nut opening 124 is also sized and configured to receive and engage the collar 55 of the gas dispersion device 10. The interior of the mounting nut opening 124 may be threaded such that the mounting nut 122 threadingly engages the collar 55.

A guide bar 126 is provided on each side surface of the housing 101 (only one guide bar 126 is visible in FIG. 13). The guide bars 126 may be received in guide tracks of a recharging station, which is described in greater detail below. Gas refill supply valve 128 (e.g., a check valve) and electrical interface 130 are also disposed on the housing 101. These components are connected to the recharging station.

An alignment key 132 is located on the housing lower portion 104. The alignment key 132 is aligned with and received within a locating guide 80 of the gas dispersion device 10 (FIG. 1). The alignment key 132 is shown in greater detail in FIG. 14. The alignment key 132 includes first and second shear cutter ports 134. First and second shear cutters 136 are located within the alignment key 132 with each shear cutter 136 aligned with a respective shear cutter port 134. When the alignment key 132 is matingly received in the locating guide 80, the shear cutter ports 134 are in alignment with shear cutter access ports 82 of the gas dispersion device 10 (FIG. 1).

Figure 15:
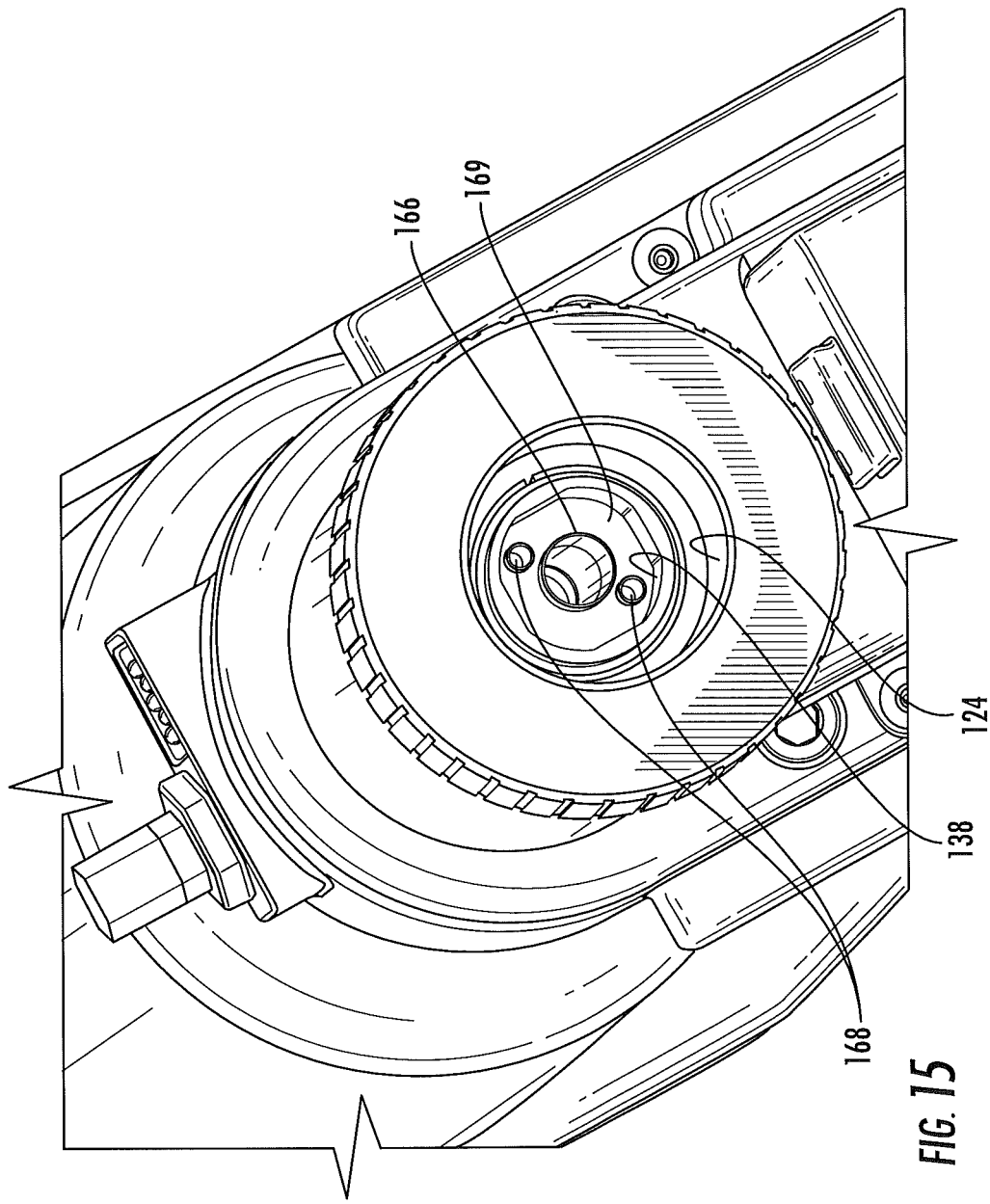
FIG. 15 is an enlarged bottom perspective view of the portable gas transfer device of FIG. 12.
Figure 16:
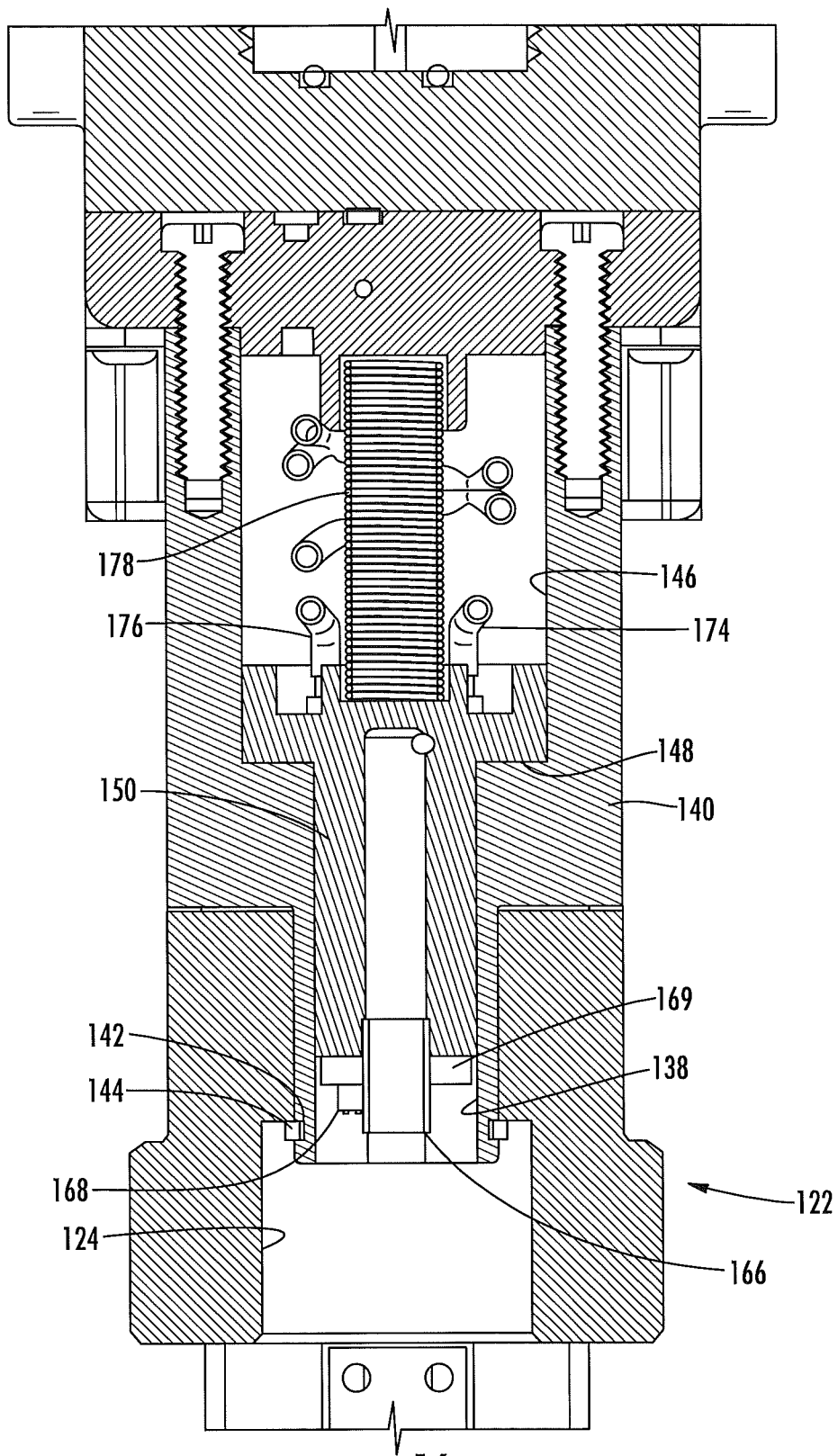
FIG. 16 is a cross-sectional front view of a portion of the portable gas transfer device of FIG. 12.

As illustrated in FIGS. 15 and 16, above the mounting nut opening 124 is a guided opening 138. The guided opening 138 is sized and configured to receive the gas flow member 24 of the gas dispersion device 10. The guided opening 138 has a similar shape or profile to that of the gas flow member 24 such that the gas flow member 24 can be matingly received in the guided opening 138. The guided opening 138 may have a polygonal and/or an oblong shape or profile to inhibit rotation of components therein, including the gas flow member 24 of the gas dispersion device 10.

A fixed housing portion 140 is illustrated in FIG. 16. The fixed housing portion 140 may be part of the housing 101 or attached thereto. At or near the bottom of the fixed housing portion 140 is an annular groove 142 that is configured to receive a retaining ring 144 therein. A top portion of the mounting nut 122 rests on the retaining ring 144.

Figure 17:
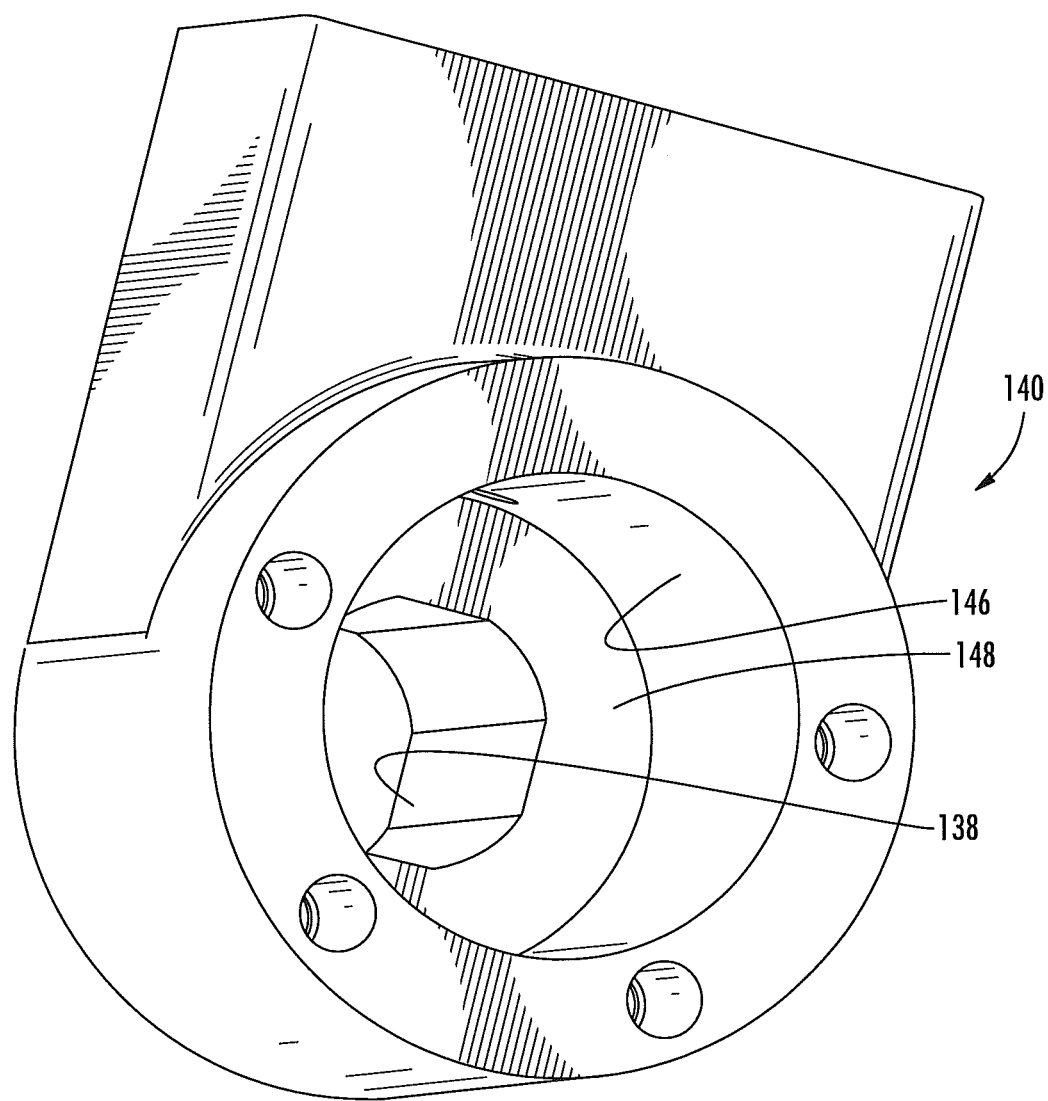
FIG. 17 is top perspective view of a fixed housing member of the portable gas transfer device of FIG. 12.
Figure 18:
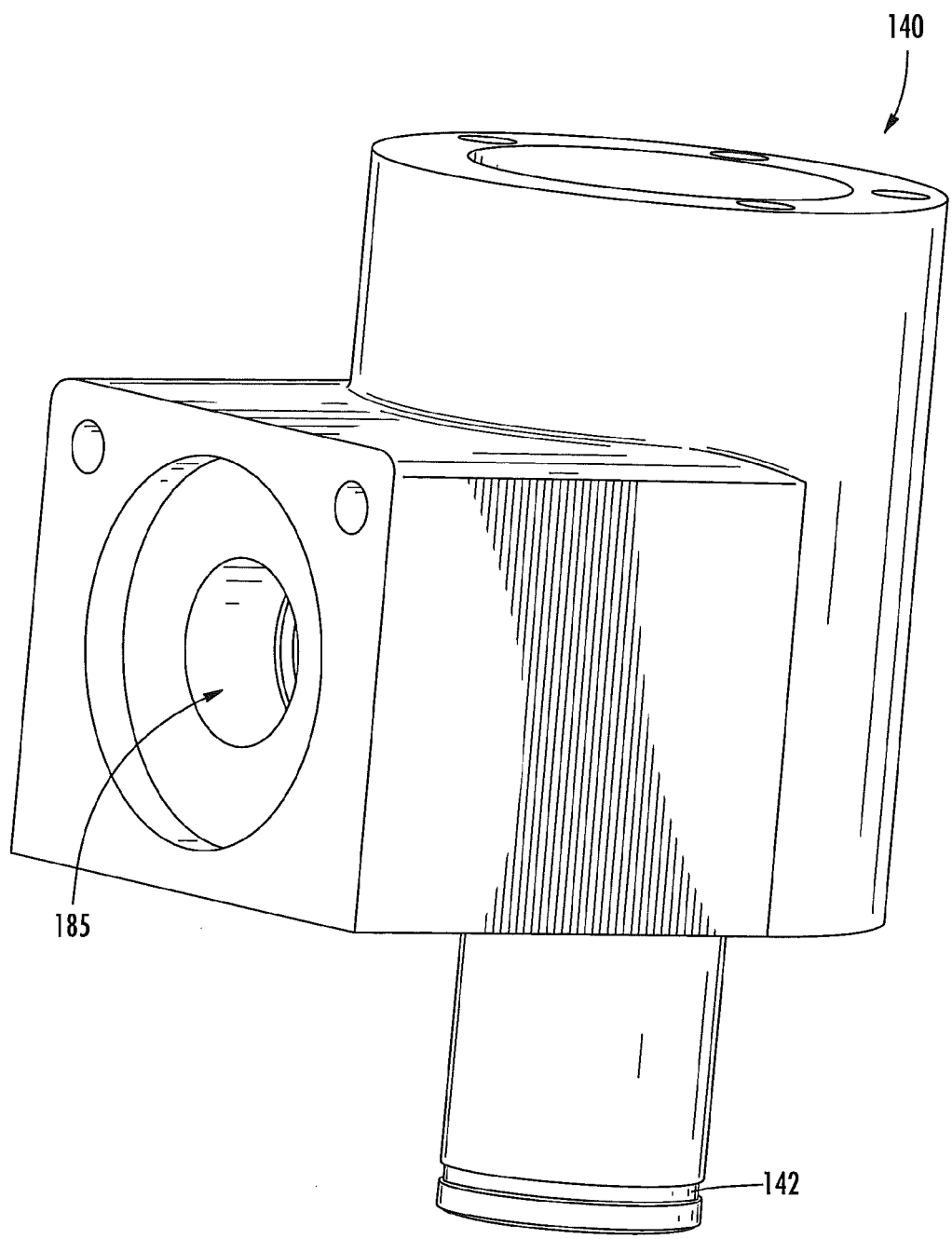
FIG. 18 is a side perspective view of the member of FIG. 17.

The fixed housing portion 140 defines the guided opening 138. Referring to FIGS. 17 and 18, the fixed housing portion 140 includes a relatively larger upper bore 146 with a sill 148 defined at the top of the guided opening 138.

Figure 19:
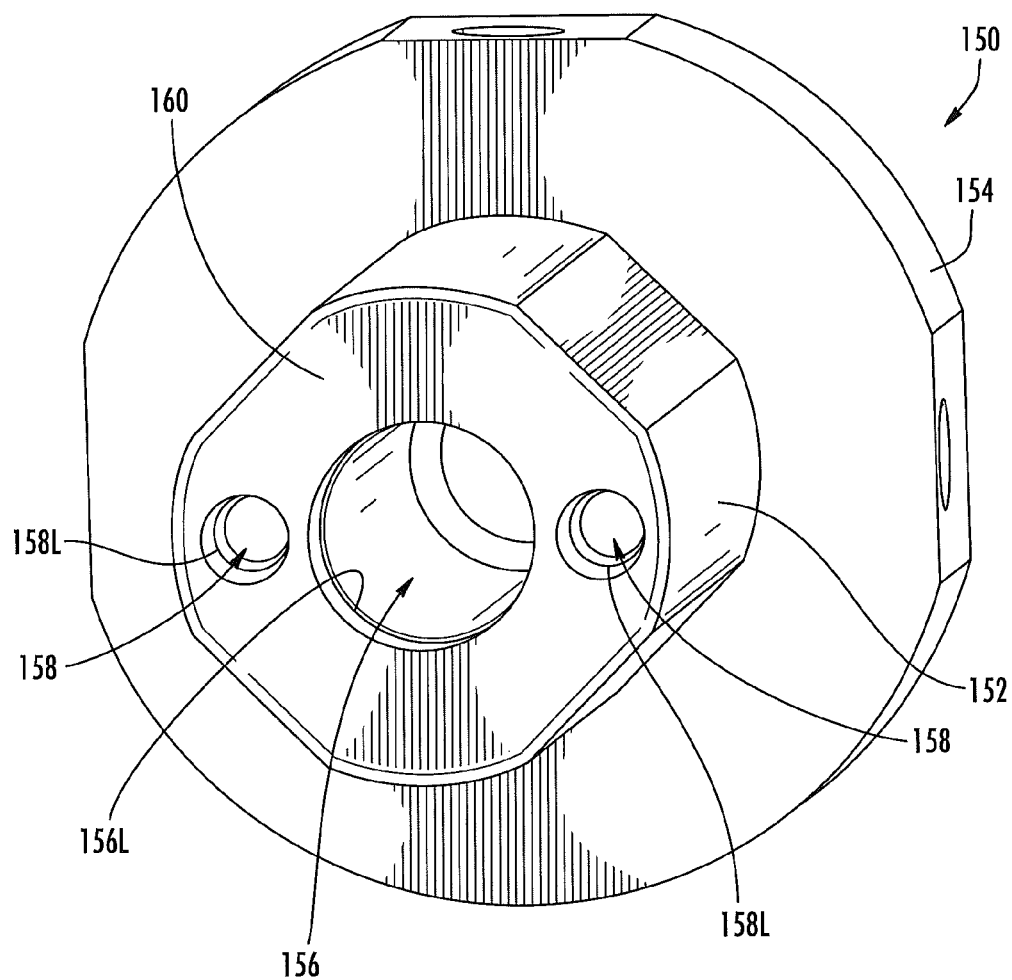
FIG. 19 is bottom perspective view of a movable gas transfer member of the portable gas transfer device of FIG. 12.
Figure 20:
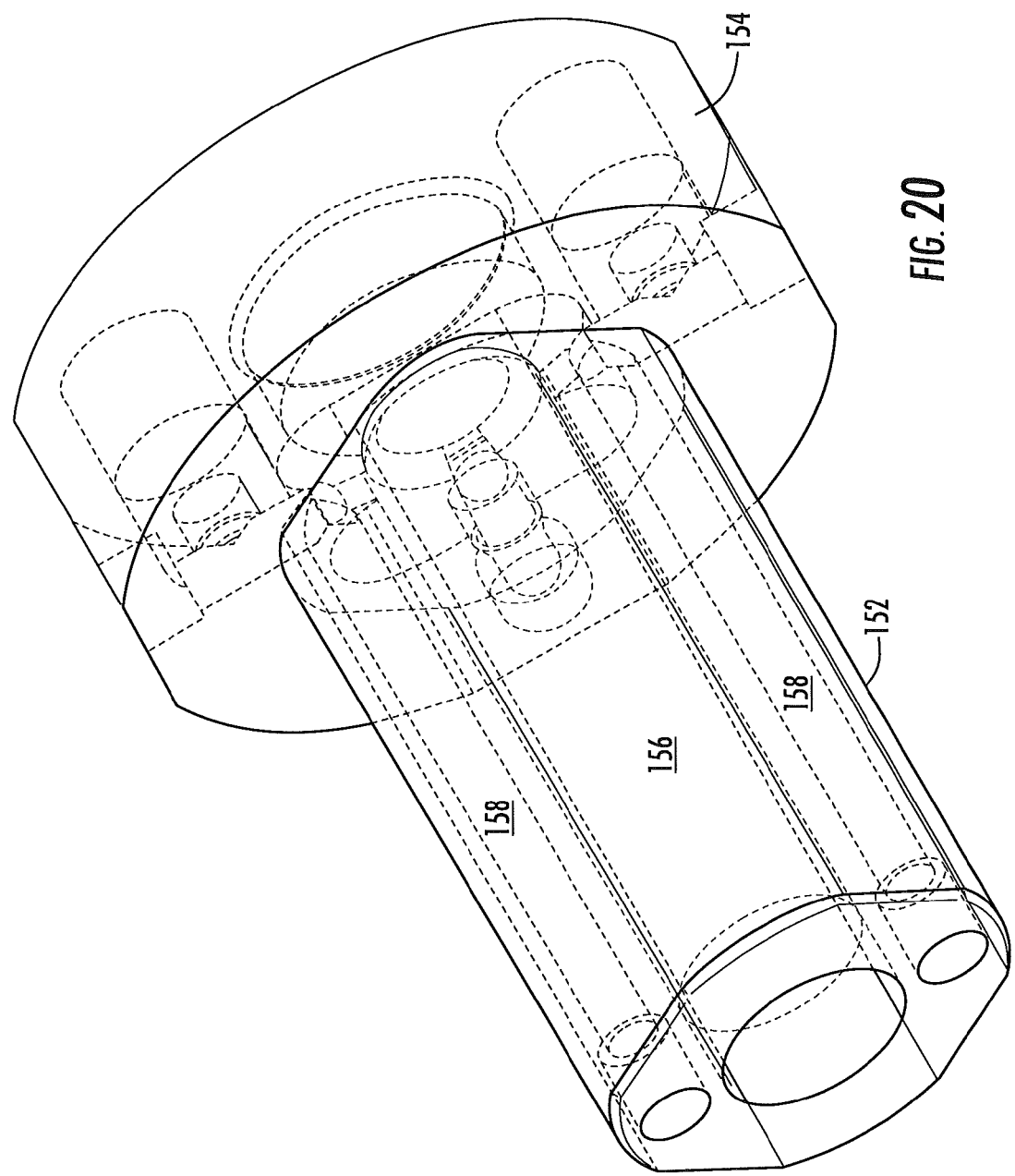
FIG. 20 is a transparent perspective view of the member of FIG. 19.
Figure 21:
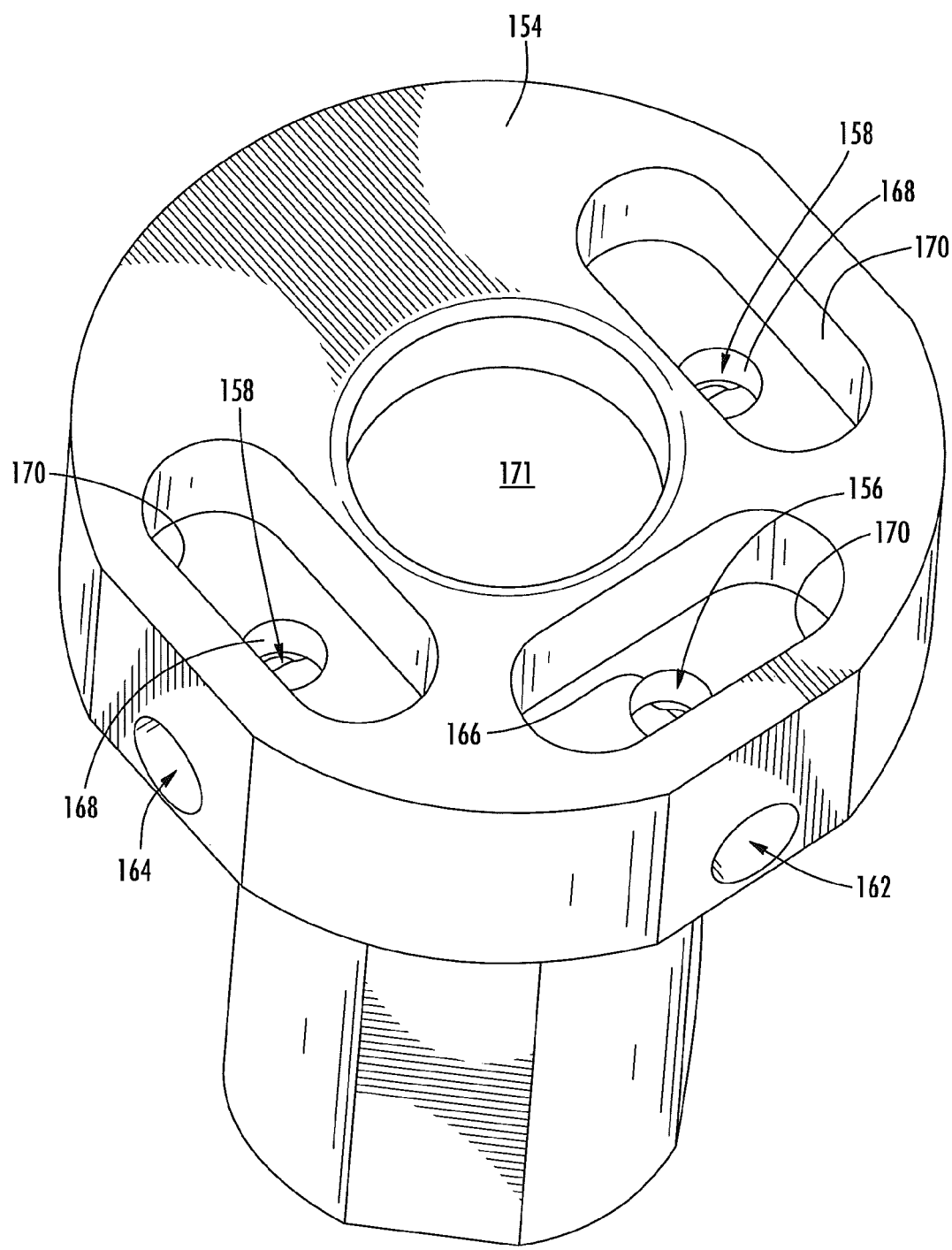
FIG. 21 is a top perspective view of the member of FIG. 19.

A gas flow or transfer member 150 is movable within the fixed housing member 140. As shown in FIGS. 19-21, the movable gas flow member 150 includes a lower stem portion 152 and an upper head portion 154. The lower stem portion 152 is shaped and configured to fit within the guided opening 138 of the fixed housing portion 140. The upper head portion 154 is shaped and configured to fit within the upper bore 146 of the fixed housing portion 140. The head portion 154 sits on the sill 148 with the gas flow member 150 in a "seated" position. As will be explained in more detail below, when the gas dispersion device 10 and the gas transfer device 100 are initially coupled, the gas flow member 150 is in the seated position when the gas dispersion device 10 is in the sterilization position. Also, the gas flow member 150 moves upward into a "raised" position when the gas dispersion device 10 moves to the post-sterilization or product flow position.

One gas supply passageway 156 and first and second gas return or discharge passageways 158 extend through the gas flow or transfer member 150. A counterbore forms a ledge or sill 156L, 158L in each passageway 156, 158 near a bottom surface 160 of the stem portion 152 (FIG. 19). As illustrated in FIGS. 15 and 16, a stainless steel tube or fitting 166 is inserted into the passageway 156 such that one end of the tube 166 abuts the ledge 156L and the other end of the tube 166 extends outwardly from the lower surface 160 of the stem portion 152. Similarly, a stainless steel tube or fitting 168 is inserted into each passageway 158 such that one end of the tube 168 abuts the ledge 158L and the other end of the tube 168 extends outwardly from the lower surface 160.

A face seal 169 is adhered or otherwise attached to the lower surface 160 of the gas flow member 150. The face seal 169 has generally the same shape or profile as the guided opening 138 and the gas flow member stem portion 152. The face seal 169 includes apertures that are aligned with the gas flow member passageways 156, 158. When attached, the stainless steel tubes 166, 168 extend downwardly past the face seal 169.

As shown in FIGS. 20 and 21, each of the passageways 156, 158 extends upwardly through the stem portion 152, then makes a pair of 90 degree turns in the head portion 154. This configuration allows for the passageways to be spaced apart a greater radial distance such that tubes connected thereto may wrap around a compression spring, as described below. An opening 162 may be formed from one of the 90 degree runs of the passageway 156 and openings 164 may be formed from one of the 90 degree runs of the passageways 158. The openings 162, 164 may be filled with plugs 167 (FIG. 22).

An opening 166 is formed from the other of the 90 degree runs of the passageway 156 and openings 168 are formed from the other of the 90 degree runs of the passageways 158. The openings 166, 168 are located in alcoves 170. The alcoves 170 provide tooling space for the attachment of fittings 172, such as barbed fittings, to the openings 166, 168 (FIG. 22).

Figure 22:
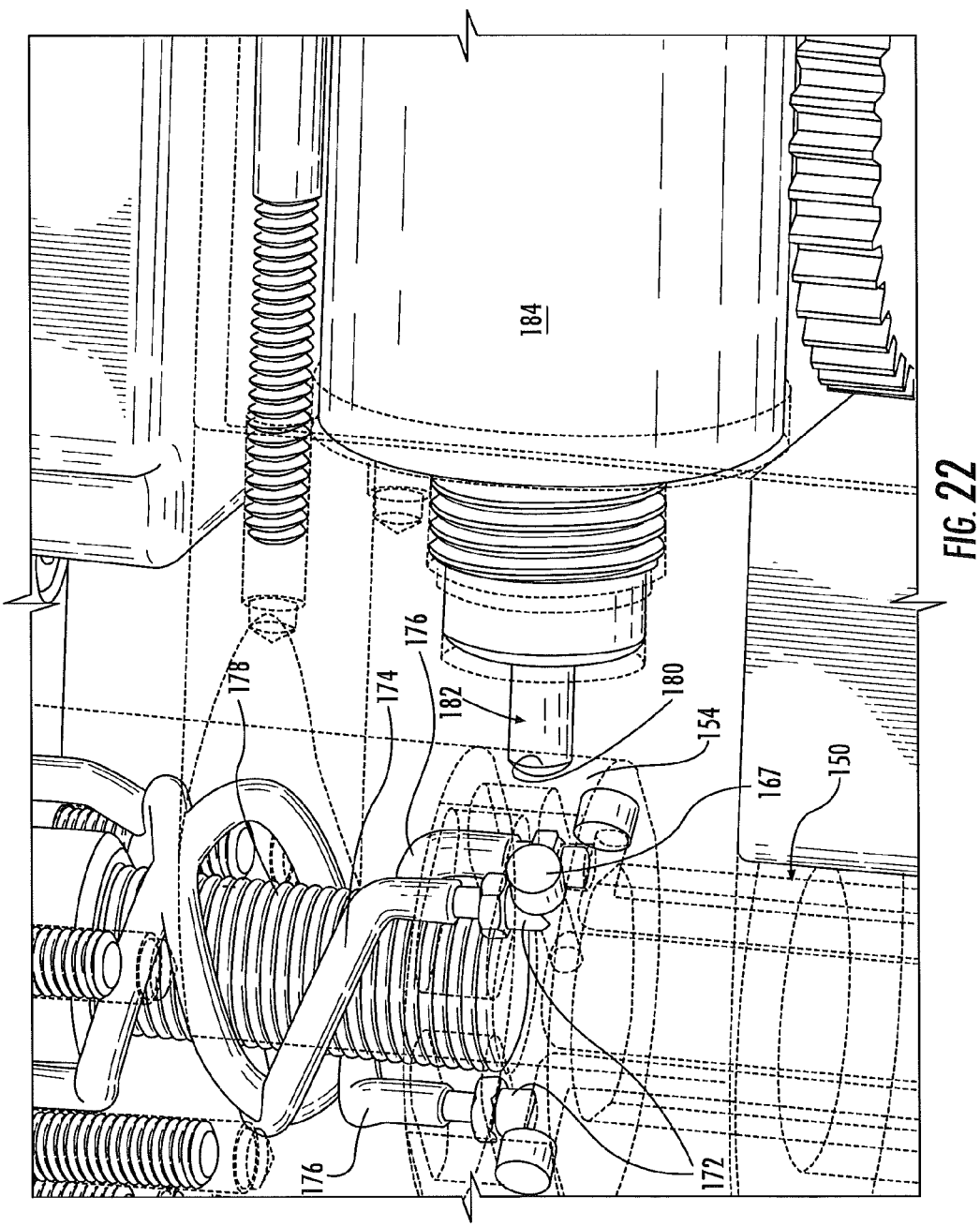
FIG. 22 is an enlarged partially transparent view illustrating interior components of the portable gas transfer device of FIG. 12.

Turning to FIG. 22, a flexible tube 174 is attached to the fitting 172 attached to the opening 166. A flexible tube 176 is attached to the fitting 172 attached to each opening 168. The flexible tubes 176 receive return or discharge gas that flows upwardly through the passageways 158 of the gas transfer member 150. The flexible tube 174 ultimately supplies pressurized gas to the passageway 156 of the gas transfer member 150 such that the pressurized gas may flow downwardly therethrough.

The tubes 174, 176 extend upwardly and wrap around a compression spring 178. The tubes 174, 176 may be wrapped around the spring 178 in a helical configuration, for example. Again, the gas transfer member 150 is configured to move upward from its seated position; for example, the gas transfer member 150 may move upward after a "successful sterilization event" has been performed by the gas dispersion device 10 and detected or validated by the gas transfer device 100. In FIG. 22, the gas transfer member 150 is shown in its "seated" or down position. The compression spring 178 is received in a central valley 171 of the gas flow member head 154 (FIG. 21) and helps urge the gas transfer member 150 in the seated position. Further, the gas flow member head 154 includes an opening 180 sized and configured to receive a pin 182. The pin 182 is extendable and retractable, for example by a solenoid valve 184. The solenoid valve 184 may be received in an opening 185 of the fixed housing member 140 (FIG. 18). In FIG. 22, the pin 182 is shown in its extended position, engaging the opening 180, thereby further urging the gas flow member to remain the down or seated position.

Figure 23:
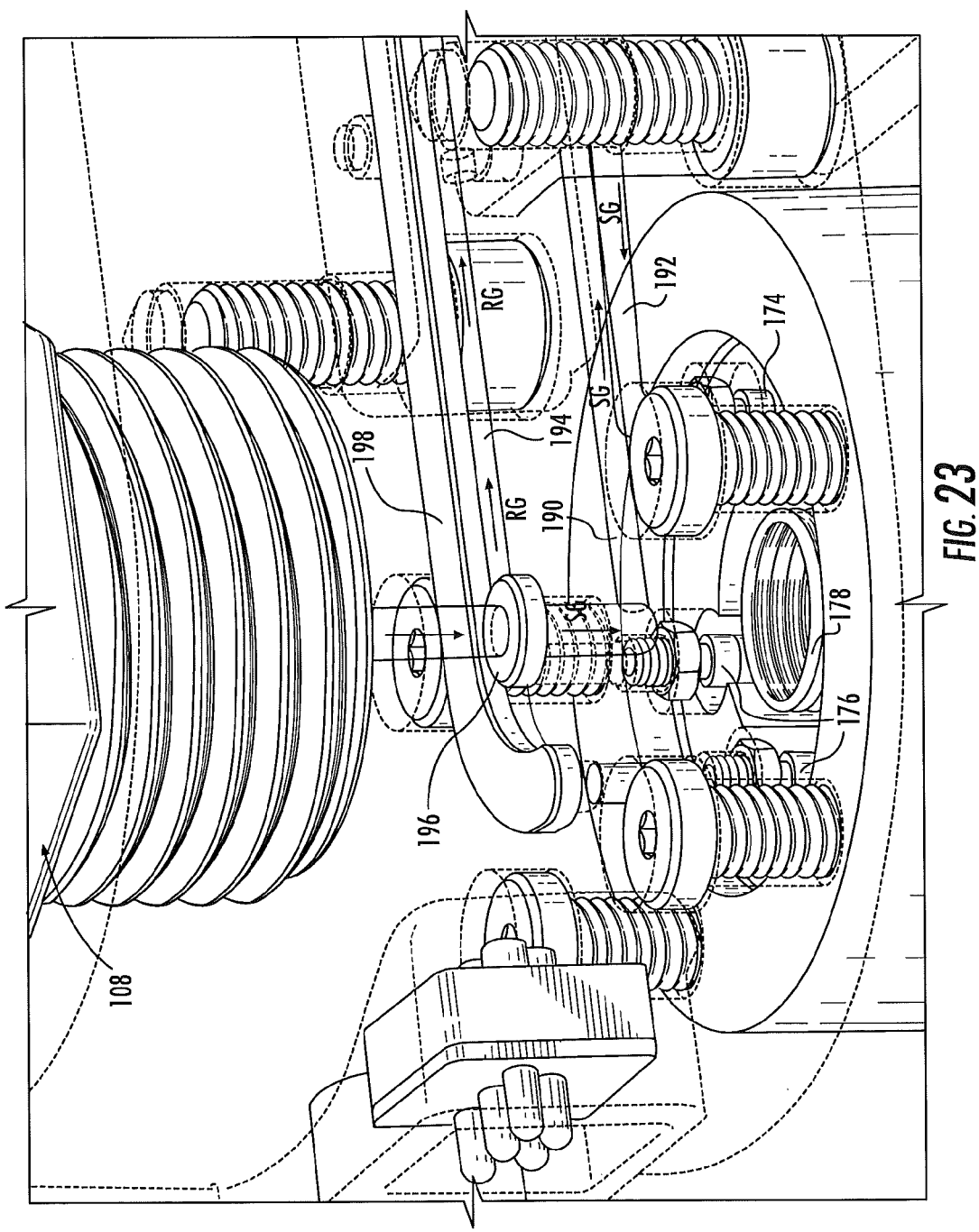
FIG. 23 is an enlarged partially transparent view illustrating portions of gas flow passageways of the portable gas transfer device of FIG. 12.

FIG. 23 illustrates a portion of the gas transfer device 100 above the compression spring 178. As illustrated, the tubes 174, 176 terminate near a top portion of the spring 178, at which point they connect with gas flow passageways (via barbed connectors, for example). Pressurized gas is supplied from the gas supply canister 108, as shown by the arrows indicated SG. The pressurized supply gas travels along passageway 190 to a first port of a solenoid valve and then travels along a different passageway 192 from a second port of the solenoid valve. The solenoid valve is described in further detail below. The gas that travels through passageway 192 enters the supply tube 174 and travels downwardly to the gas transfer member 150, where the supply gas enters the supply gas passageway 156.

The return or discharge gas flowing upwardly through the tubes 176 is routed to a common return gas passageway 194 and travels in a path shown by the arrows RG. Face seals 196, 198 may be provided to seal the supply gas and return gas passageways, respectively.

Figure 24:
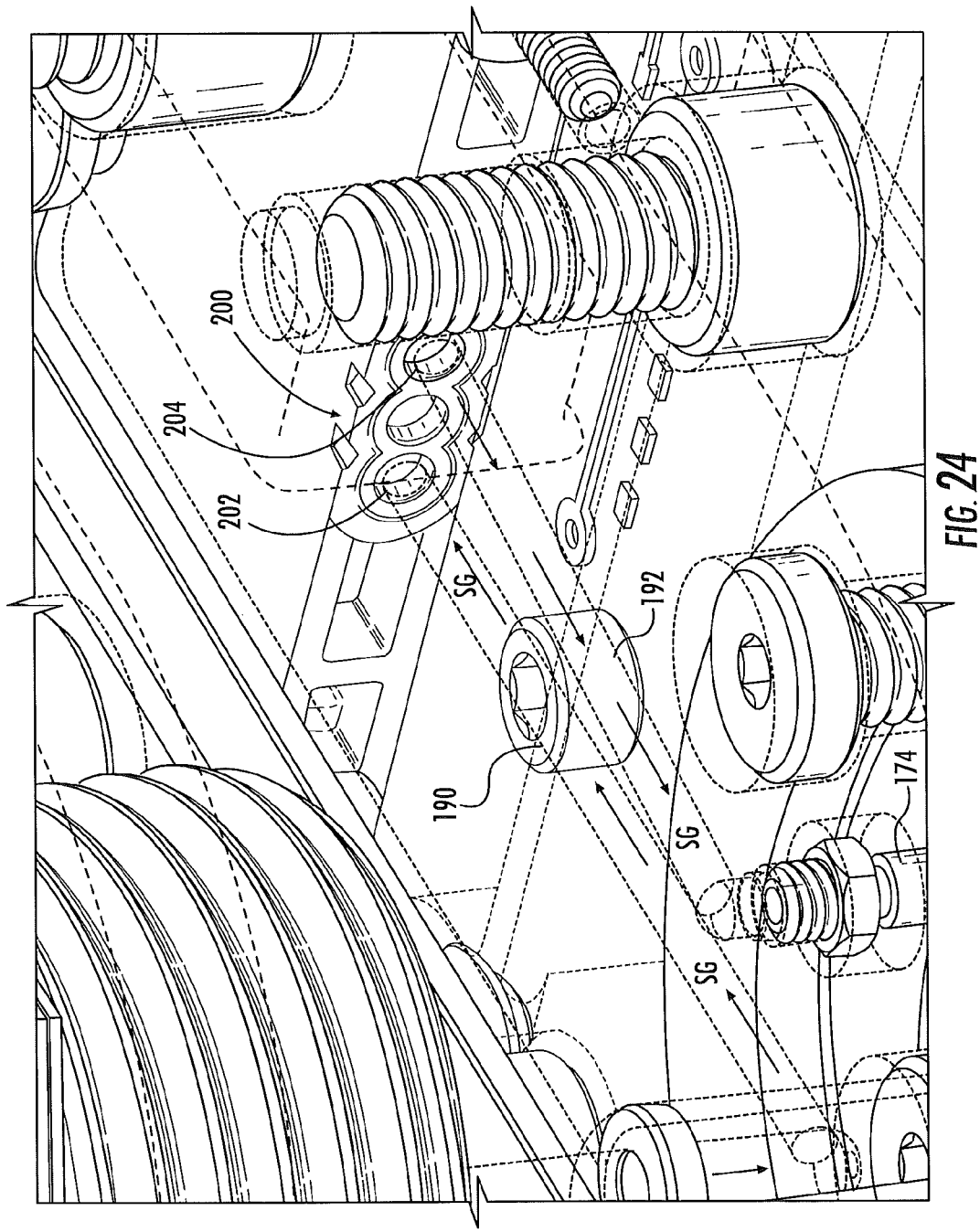
FIG. 24 is an enlarged partially transparent view illustrating portions of gas flow passageways of the portable gas transfer device of FIG. 12.

FIG. 24 shows the path of the pressurized supply gas SG in greater detail. A solenoid valve 200 is provided. Supply gas passageway 190 is attached to a first port 202 of the solenoid valve 200 and supply gas passageway 192 is attached to a second port 204 of the solenoid valve. The solenoid valve 202 is "normally off" or "normally closed" such that supply gas typically will not flow into or through the passageway 192. The valve 202 may be energized or otherwise receive a signal to open when supply gas is needed (i.e., when sterilization is to begin at the gas dispersion device 10). At this point, the supply gas will flow into and through the passageway 192, through the tube 174 and downwardly through the passageway 156 of the gas flow or transfer member 150.

Figure 25:
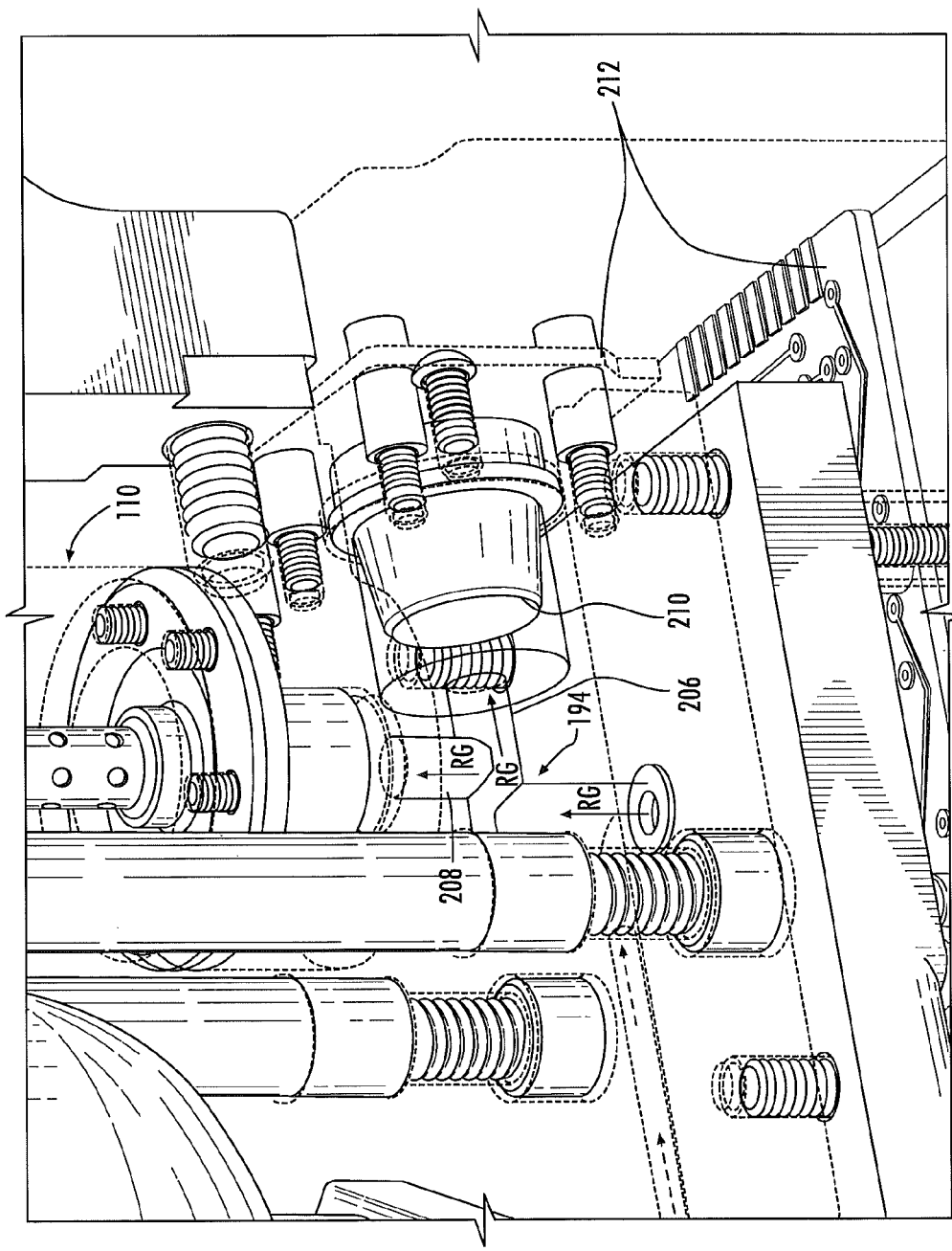
FIG. 25 is an enlarged partially transparent view illustrating portions of gas flow passageways of the portable gas transfer device of FIG. 12.

FIG. 25 shows the path of the discharge or return gas RG in greater detail. The return gas passageway 194 ultimately branches into two segments. A first segment 206 directs a portion of the discharge or return gas RG to a gas level monitor sensor 210. The gas level monitor sensor 210 is configured to monitor characteristics of the return gas such that a determination can be made as to whether a successful sterilization has taken place. For example, if ozone is used as the pressurized gas, the sensor 210 may monitor the amount of oxygen or ozone in the return gas such that a concentration over time (e.g., ppm ozone/time) can be used to determine or validate whether sterilization is complete. Also shown in FIG. 25 are printed circuit boards 212. A lesser or greater number of circuit boards may be provided in various embodiments. The printed circuit board(s) 212 may include or be associated with at least one controller. The printed circuit board(s) and/or the controller may control certain operations such as supplying power to the solenoid valves, monitoring the sensors, validating sterilization events and other operations that are described herein.

Figure 12:
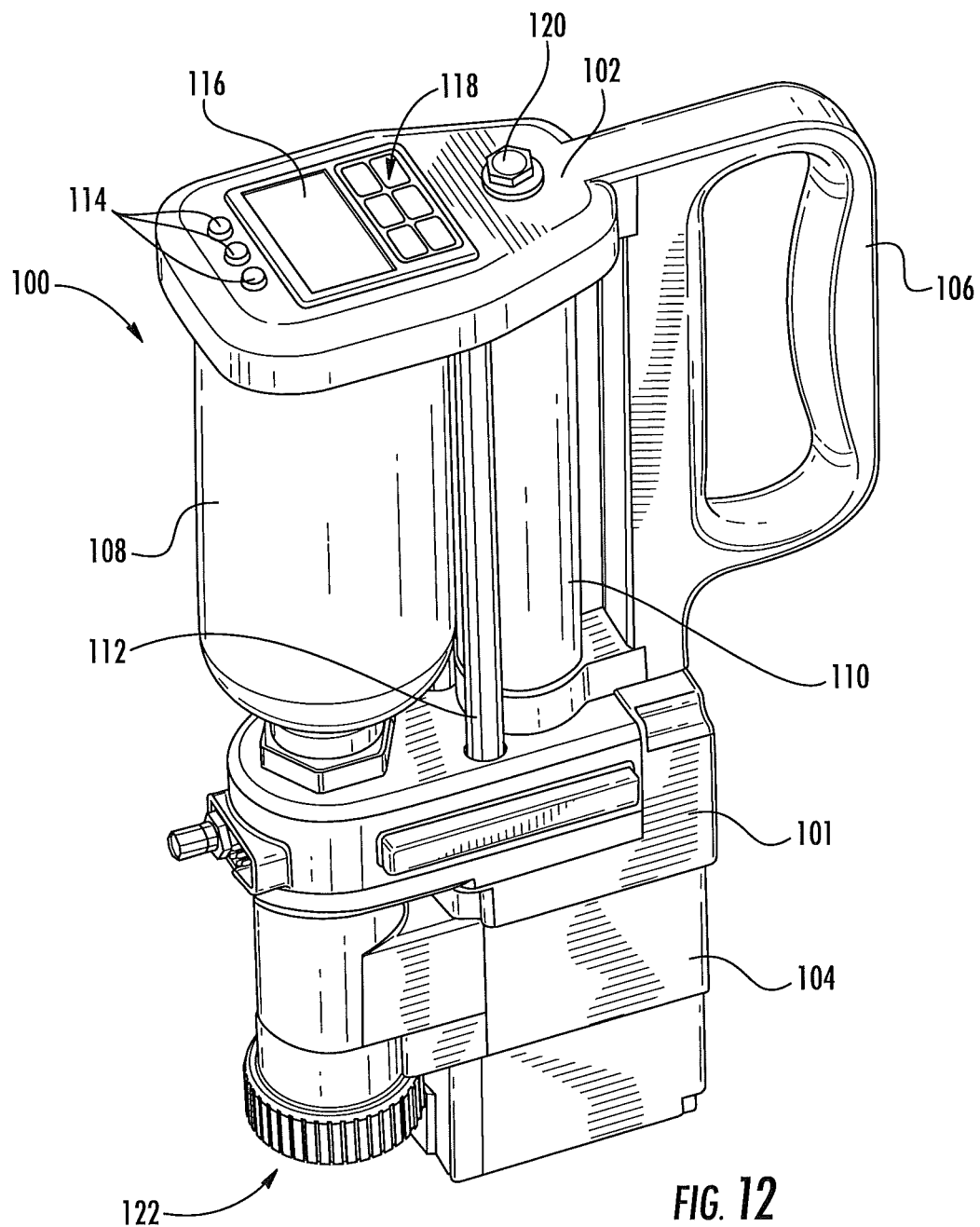
FIG. 12 is a top perspective view of a portable gas transfer device according to some embodiments.
Figure 26:
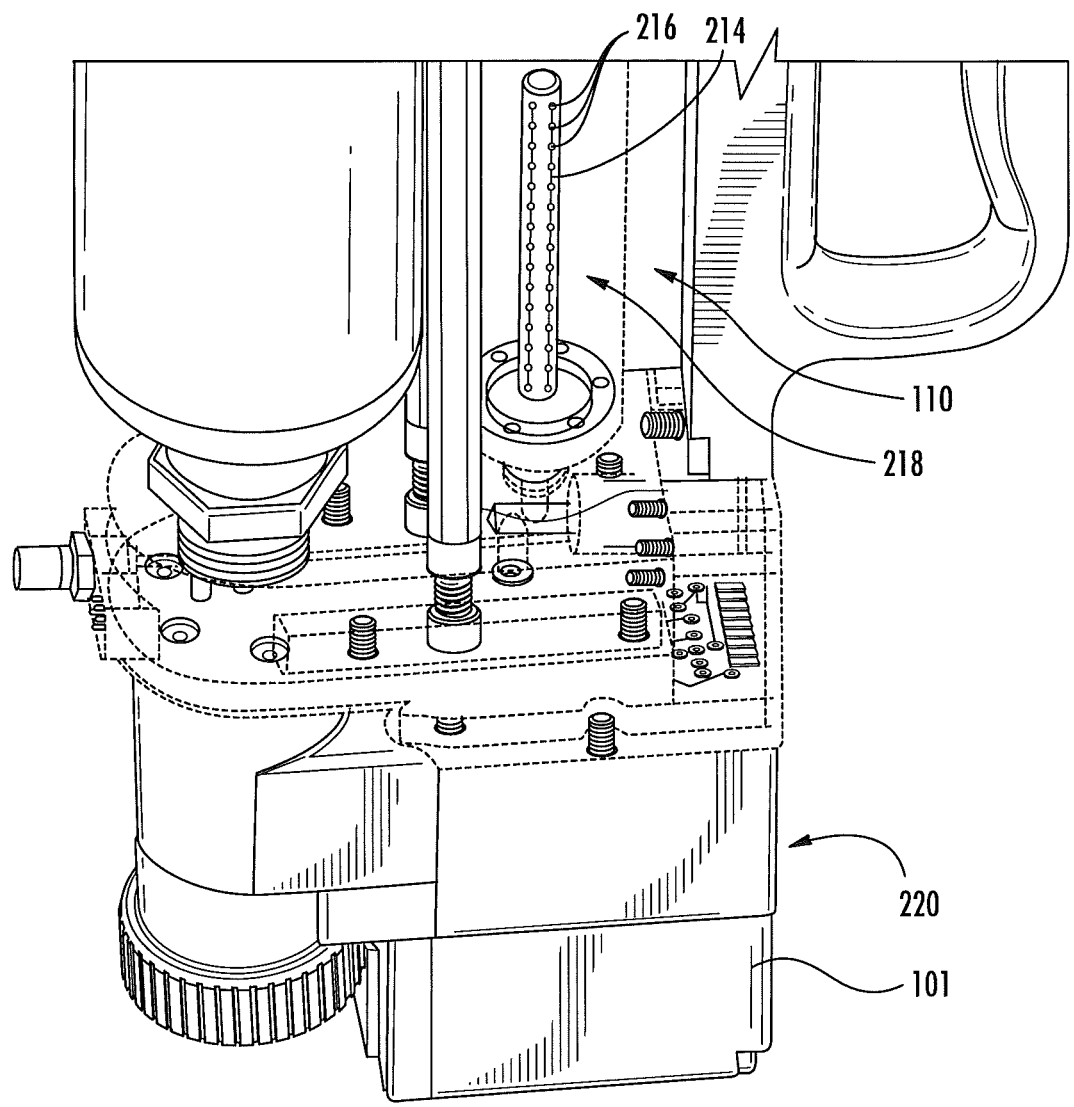
FIG. 26 is a partial perspective view of the portable gas transfer device of FIG. 12.

A second segment 208 directs a portion of the return gas RG to the gas discharge catalyst canister 110. Referring to FIG. 26, return gas is supplied to a gas diffuser tube 214 located in the gas discharge catalyst canister 110. The gas diffuser tube 214 includes a plurality of apertures 216 on an outer surface thereof such that return gas is diffused in the area surrounding the diffuser tube 214. A suitable catalyst material 218 is positioned around the gas diffuser tube 214 to convert the return gas to oxygen, which is then released through the gas vent 120 (FIG. 12). For example, if ozone is used as the sterilization gas, manganese dioxide/copper oxide, activated charcoal or a molecular sieve may be supplied around the gas diffuser tube 214 such that waste ozone is converted to oxygen.

Figure 27:
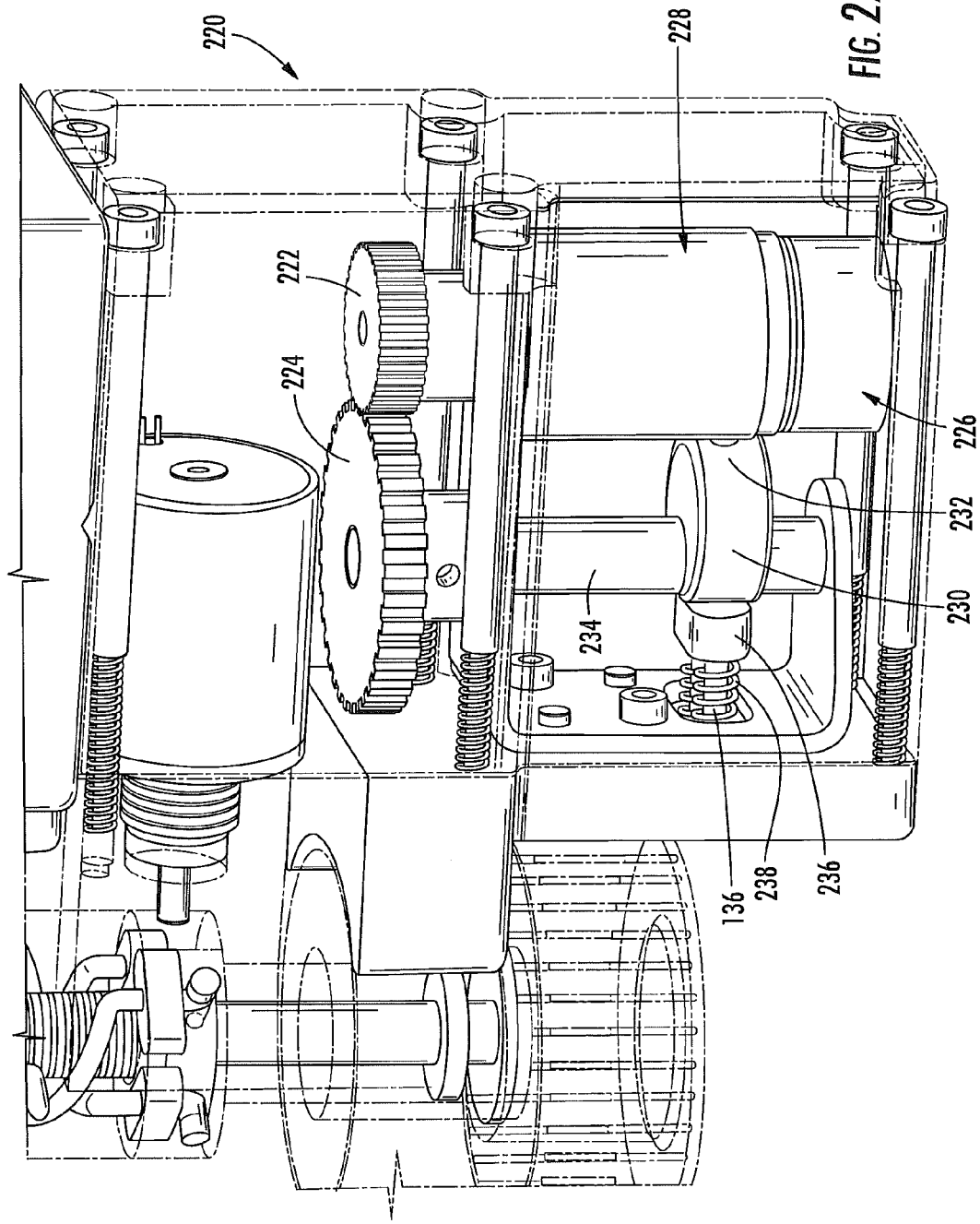
FIG. 27 is an enlarged partially transparent view illustrating interior components of the portable gas transfer device of FIG. 12.

A shear cutter assembly 220 is illustrated in FIG. 27. The shear cutter assembly 220 is positioned inside the housing 101. The assembly includes first and second spur gears 222, 224 having a 2:1 gear reduction. The first gear 222 is driven by a DC motor 226 and a planetary gear reducer 228 (these components are hidden from view by respective casings or housings). An eccentric cam 230 having an extended portion 232 is driven by gear 224 via a cam shaft 234. A cam follower 236 engages the cam 230. Attached to the cam follower 236 are the shear cutters 136 (see FIG. 14). A spring 238 surrounds at least a portion of each shear cutter 136; the springs 238 are also attached to the cam follower 236. The springs 238 are biased such that the cam follower 236 is urged toward the cam 230.

Figure 14:
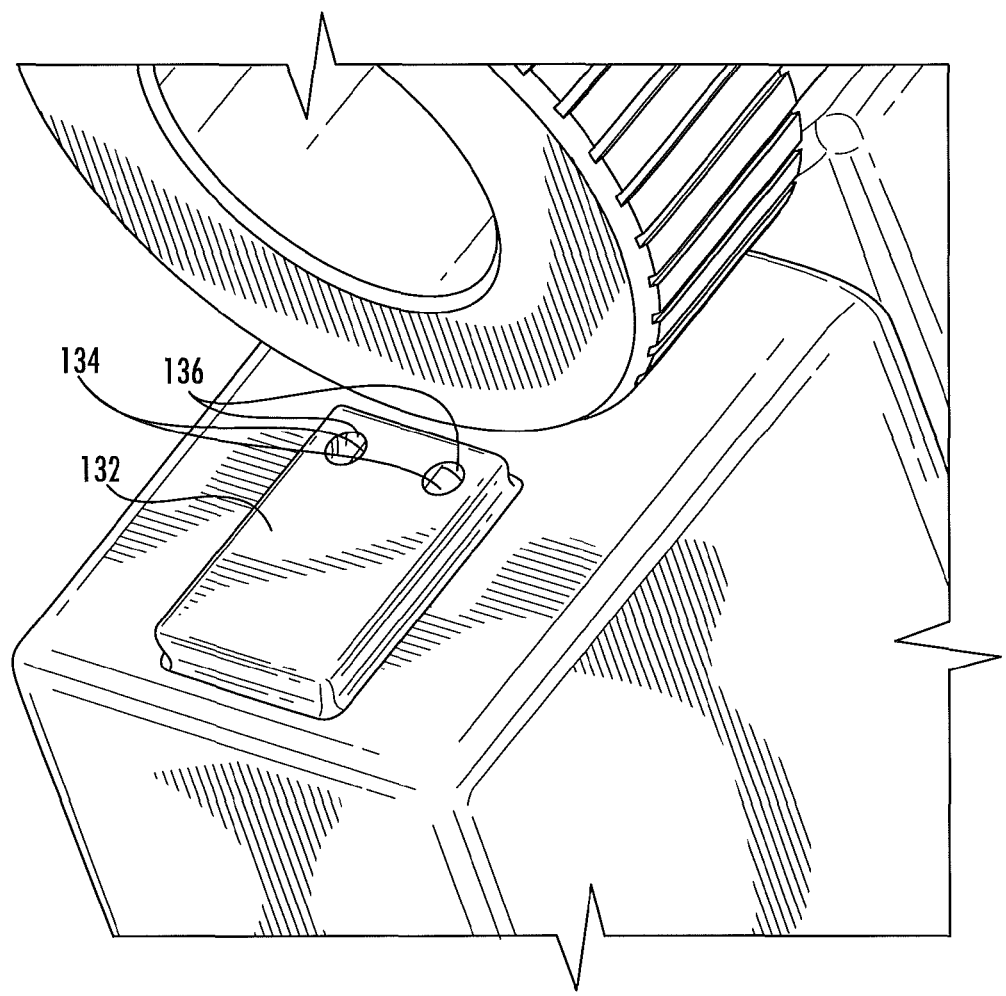
FIG. 14 is an enlarged bottom perspective view of the portable gas transfer device of FIG. 12.

The motor 226 drives the gear 222, which in turn drives the gear 224, which in turn rotates the cam shaft 234 and the eccentric cam 230. As the eccentric cam 230 rotates, the springs 238 compress and the cam follower 236 and the shear cutters 136 are pushed away from the cam shaft 234. Eventually, when the cam extended portion 232 engages the cam follower 236, the shear cutters 136 fully extend from the shear cutter ports 134 (FIG. 14). As noted above, the alignment key 132 of the canister assembly 100 may be matingly received in the locating guide 80 of the gas dispersion device 10 such that the shear cutter ports 134 are aligned with shear cutter access ports 82 of the gas dispersion device 10 (FIG. 1). As such, with the shear cutters 136 extended, the shear key 58 of the gas dispersion device 10 is cut, allowing the gas dispersion device 10 (or the gas flow member 24 thereof) to move from the sterilization position to the product flow position, as discussed further below.

Figure 28:
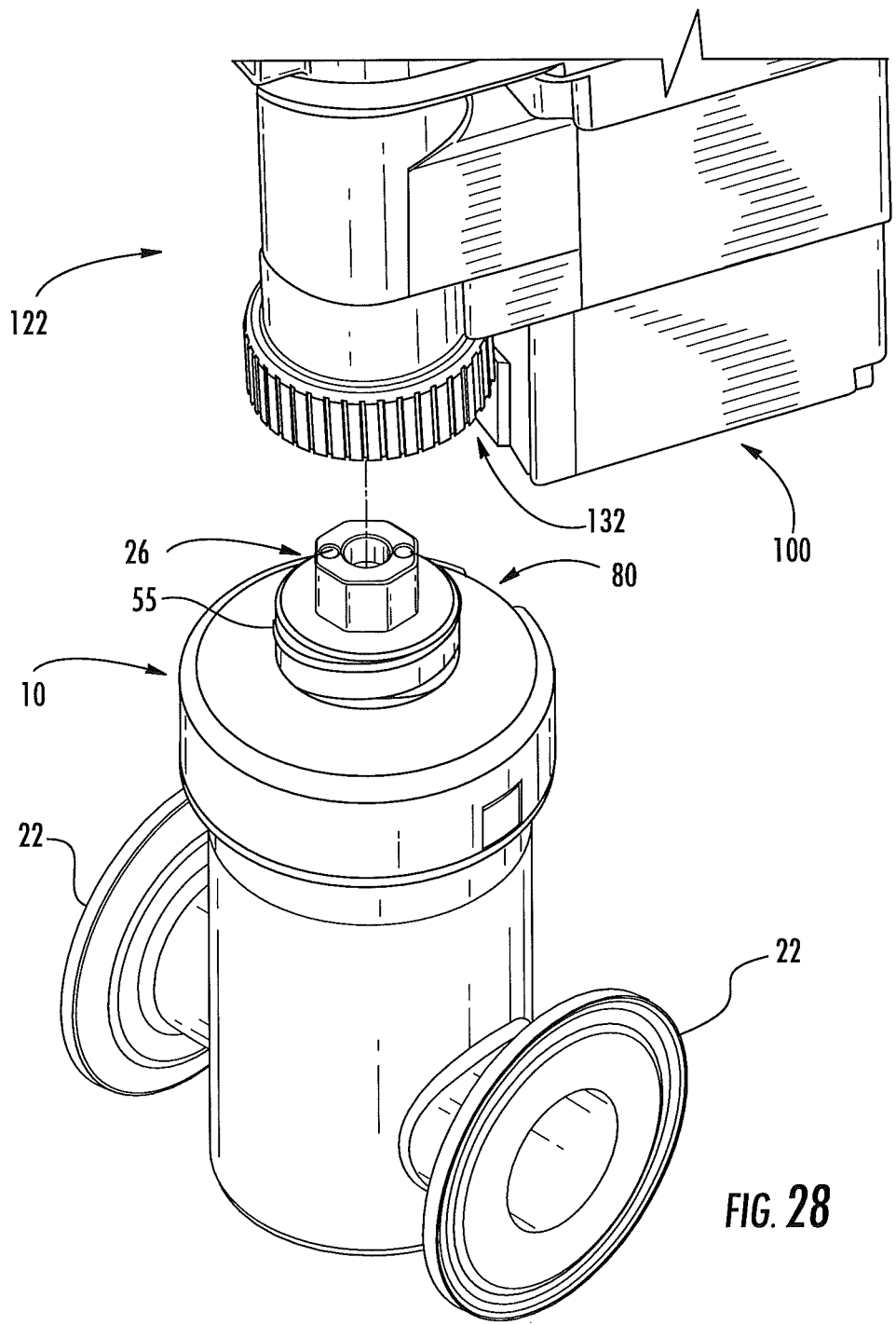
FIG. 28 is a partial perspective view of the portable gas transfer device of FIG. 12 positioned over the gas dispersion device of FIG. 1.
Figure 29:
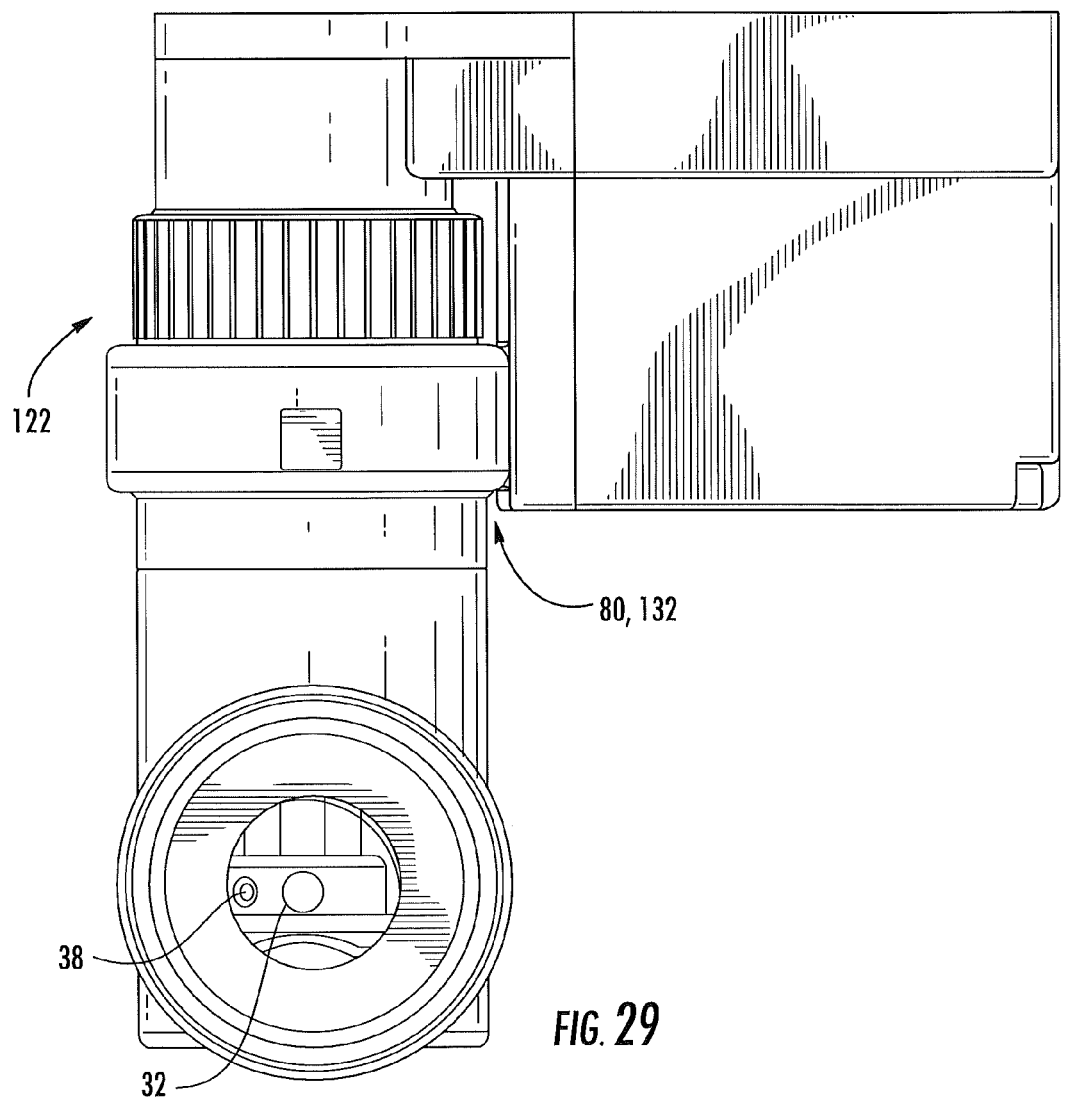
FIG. 29 is an end view of the portable gas transfer device of FIG. 12 coupled to the gas dispersion device of FIG. 1.

Connection of the gas dispersion device 10 and the gas transfer device 100 and the ensuing operation of the combined system will now be described in greater detail. As shown in FIG. 28, the gas transfer device 100 is positioned over the gas dispersion device 10; specifically, the mounting nut 122 is centered over the collar 55 and the gas flow member upper portion 26. As shown in FIG. 29, the alignment key 132 of the transfer device 100 is matingly received in the locating guide 80 of the gas dispersion device 10. The mounting nut 122 is then rotated to threadingly engage the collar 55 of the gas dispersion device. Although not illustrated in FIGS. 28 and 29, flow components (e.g., connectors, fittings, sensors, tubes, etc.) will typically be operatively connected to the flanges 22 of the gas dispersion device 10 for subsequent sterilization before the gas transfer device 100 is introduced.

The gas transfer device 100 is connected with the gas dispersion device 10 in the sterilization position. This is apparent from FIG. 29, wherein the gas dispersion and gas return ports 32, 38 are visible through the conduit 20. As such, the gas flow member 24 is in its lowered position when the gas canister assembly 100 is coupled to the gas dispersion device 10.

Referring to FIGS. 1, 2, 15 and 16, the gas flow member upper portion 26 of the gas dispersion device 10 is received in the guided opening 138 of the gas transfer device 100. The top surface of the gas flow member upper portion 26 contacts the face seal 169. The tube 166 is received in the gas supply passageway 34 through the gas supply port 30 and the tubes 168 are received in the gas return passageways 36 through the return discharge gas ports 40. The ends of the tubes 166, 168 may be seated on a ledge in respective passageways 34, 36 similar to the opposite ends of the tubes 166, 168 seated on the ledges 156L, 158L in the passageways 156, 158 (FIG. 19). The insertion of the tubes 166, 168 into the passageways along with the face seal 169 help to ensure a sealed connection between the gas dispersion device 10 and the gas transfer device 100.

In this position, the gas supply passageway 34 of the gas dispersion device 10 is in fluid communication with the gas supply canister 108 and the gas return passageways 36 of the gas dispersion device 10 are in fluid communication with the gas discharge catalyst canister 110, with the exception of any flow blocking mechanisms disposed therebetween (e.g., the solenoid valve 200 shown in FIG. 24).

Figure 30:
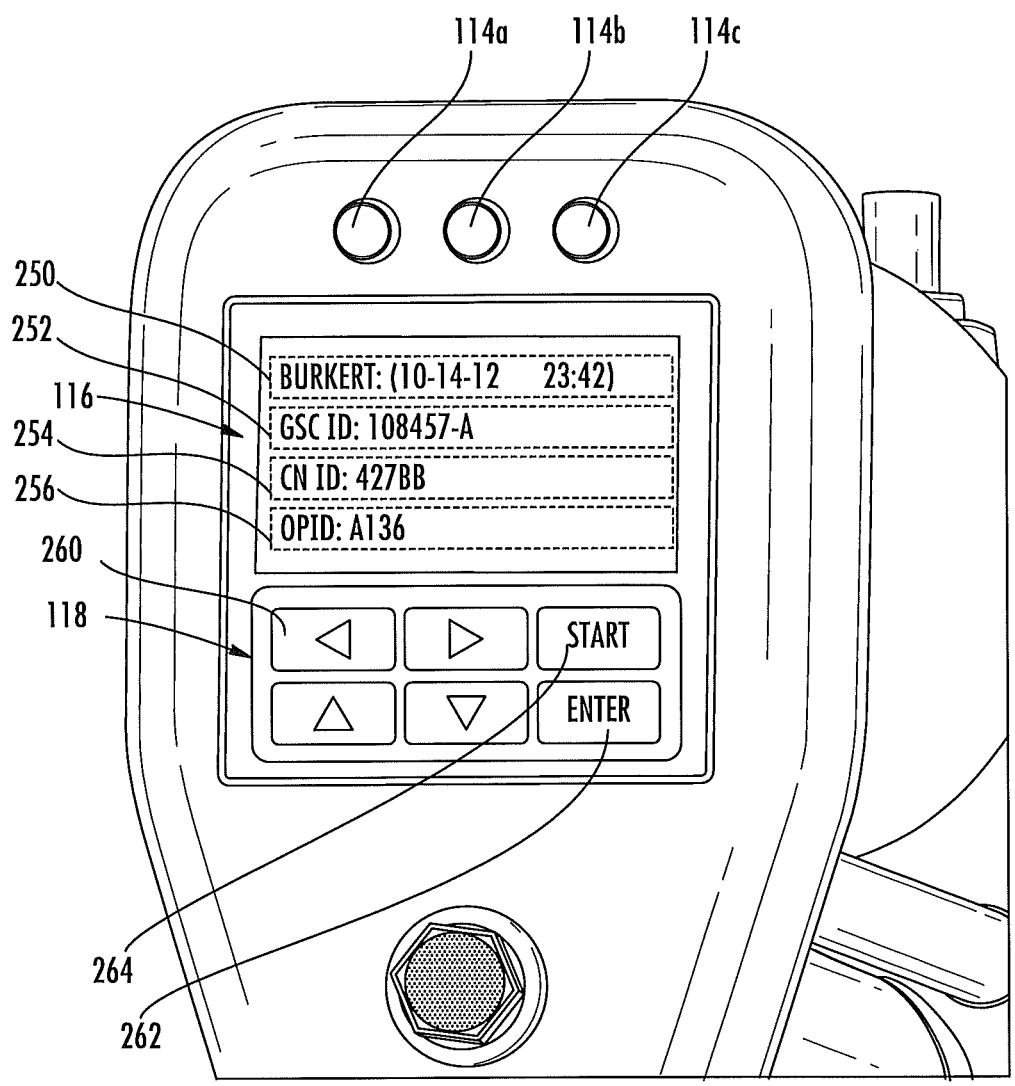
FIG. 30 is a partial top perspective view of the portable gas transfer device of FIG. 12.

With the portable gas transfer device 100 coupled to the gas dispersion device 10 as described above, an operator may use the display 116, the operator interface 118 and/or the indicator lights 114 to initiate and monitor a sterilization process. As shown in FIG. 30, the display 116 may display data including, but not limited to, a date and time stamp 250, an identification of the gas supply canister assembly 252, a connection or joint identification 254 and an operator identification 256.

The date and time 250 may be dynamically updated by at least one onboard controller of the gas transfer device 100. The gas canister assembly identification 252 may also be provided by the onboard controller. These data may be automatically displayed on the display 116 without any user input. In some embodiments, these data are displayed before the gas transfer device 100 is connected to the gas dispersion device 10 as well as after the gas transfer device 100 is connected to the gas dispersion device 10.

The connection or joint identification 254 identifies the connection or joint in the bioprocessing system that is to be sterilized. Specifically; this is the connection or joint at which a particular gas dispersion device 10 is attached (e.g., a specific connection or joint in a bioprocessing system). The connection or joint identification 254 may be displayed on the display 116 without any user input and/or before the gas canister assembly 100 is connected with the gas dispersion device 10. In this regard, the connection or joint identification 254 may direct the operator to the proper connection or joint to be sterilized. In some other embodiments, the operator may use the operator interface 118 to input the connection or joint identification, which may be marked on or near the connection or joint or on a map, for example. The operator may depress the arrow keys 260 to scroll between various displays or lists, one of which may include a list of possible connections or joints. The operator may depress the "enter" key 262 when the correct connection or joint identification is found or highlighted. Other configurations for the operator interface 118 are contemplated. As just one example, the display 116 may be a touch-sensitive display to supplement or replace the operator interface 118.

The operator identification 256 generally must be input by the operator. The operator may use the operator interface 118 to enter a password or other identifying information. Once the operator has been identified, the gas transfer device 100 may "unlock" to allow the sterilization process to begin.

The operator may press the "start" button 264 to begin the sterilization process. The indicators 114 provide visual feedback to the operator throughout the process. The indicators 114 may be differently colored LEDs or the like to provide the visual feedback. For example, the indicator 114a may be an amber LED that indicates that sterilization is in progress, the indicator 114b may be a green LED that indicates that a successful sterilization has taken place and the indicator 114c may be a red LED that indicates an unsuccessful sterilization or that a sterilization "fault" has occurred.

At the beginning of the sterilization process, power or a signal is supplied to the solenoid valve 200 (FIG. 24). The solenoid valve 200 turns on or opens, allowing the pressurized supply gas SG to exit the port 204 and flow along the passageway 192. The supply gas SG flows in the tube 174 downwardly and around the spring 178 (FIG. 22). The supply gas SG enters the movable gas transfer member 150 at port 166 (FIG. 21) and flows downwardly through the passageway 156 of the gas transfer member 150 (FIGS. 19 and 20). The supply gas SG enters the gas dispersion device 10 through the gas supply port 30 of the gas flow member 24 (FIG. 1). The supply gas flows downwardly, then outwardly through the gas flow member supply gas passageway 34, at which point the supply gas is rapidly dispersed via the gas dispersion openings 32 (FIG. 5). The dispersed supply gas flows through the conduits 20 and past or adjacent flow components operatively attached to the flanges 22, as described in detail above.

"Post-sterilization" or return gas is received in the gas return openings 38 (FIGS. 3 and 4) and flows upwardly through the gas flow member return gas passageways 36 (FIG. 2). The return gas flows upwardly through the movable gas flow member passageways 158 (FIGS. 19-21). The return gas then enters the tubes 176 and flows therethrough upwardly and around the spring 178 (FIG. 22). As shown in FIG. 23, the return gas RG flows through a pair of short passageways which converge into the single return gas passageway 194. As shown in FIG. 25, the return gas RG flows through the passageway 194 toward the gas discharge catalyst canister 110 and the gas level monitor sensor 210. Segments 206 and 208 branch from the passageway 194. A portion of the return gas RG is directed through the segment 208 into the gas discharge catalyst canister 110, where it is converted into a safe and/or stable discharge gas, which is then discharged through the vent 120, as described above.

A portion of the return gas RG is direction through the segment 208 to contact the gas level monitor sensor 210. The sensor 210 continuously detects a characteristic, such as a level of a substance, of the return gas RG. The signal detected by the sensor 210 is provided to a controller, which continuously monitors the detected characteristic. For example, if the pressurized sterilization gas is ozone, the sensor 210 detects the level of ozone present in the return gas. The controller determines the level of ozone over time (e.g., ppm of ozone over time). A threshold value of level of ozone over time is known to correlate to a predetermined required sterilization level, such as a SAL of $10^{-6}$. When this threshold value is reached, the controller determines that a "good sterilization" has taken place. A good sterilization indicates that all components in fluid communication with the gas dispersion device 10 have been adequately sterilized.

After it has been determined or validated that a "good sterilization" has taken place, the sterilization process ends. The controller sends a signal to the solenoid 184 and the pin 182 is retracted from the opening 180 in the head portion 154 of the movable gas flow member 150 (FIG. 22). At this point, the movable gas flow member 150 remains in position; the weight of the spring 178 continues to urge the movable gas flow member 150 downward such that the head portion 154 remains seated on the sill 148 of the fixed housing member 140 (FIG. 17).

Referring to FIG. 27, the controller then sends a signal to turn on the motor 226. The motor 226 drives the gear 222, which in turn drives the gear 224. The motor turns the gear 222 one full revolution, which corresponds to one half revolution of the gear 224 due to the 2:1 reduction. The rotation of the gear 224 results in a corresponding rotation of the cam shaft 234 and eccentric cam 230. The extended portion 232 of the cam 230 fully engages the cam follower 236 after 180 degrees of rotation. As a result, the cam follower 236 and the shear cutters 136 attached thereto are pushed against the force of the spring 238 such that the shear cutters 136 extend out of the shear cutter ports 134 of the alignment key 132 (FIG. 14) and into the shear cutter access ports 82 of the gas dispersion device 10 (FIG. 1).

The shear cutters 136 cut the shear key 58 of the gas dispersion device 10 such that the pin 42 retracts from the opening 41 in the gas flow member 24 and the gas flow member 24 moves to the product flow position due to the force of the spring 44 (FIGS. 6 and 8). As illustrated in FIG. 7, the gas dispersion device 10 or the gas flow member 24 is locked in the product flow position by the locking cams 62. The gas dispersion device 10 is typically single-use disposable; accordingly, this locking action will advantageously hinder or prevent the gas dispersion device 10 from being reused for sterilization purposes.

Although not illustrated in FIG. 16, as discussed above, the gas dispersion device gas flow member 24 engages the gas canister assembly movable gas flow member 150 at the face seal 169. The tube 166 extends into the gas dispersion device gas supply port 30 and the tubes 168 extend into the gas return openings 40 (FIG. 1). When the gas dispersion device gas flow member 24 moves upward into the product flow position, the movable gas flow member 150 moves upward a corresponding distance. In some embodiments, the upward travel is less than about 1 inch. In some embodiments, the upward travel is between about 0.5 and about 0.75 inches.

As described above, at least one of the indicators 114 (FIG. 30) may provide visual feedback to the operator that the sterilization process is complete and/or that a successful or "good" sterilization event has been validated. After the sterilization process, the operator may loosen the mounting nut 122 and disconnect the gas transfer device 100 from the gas dispersion device 10.

Figure 31:
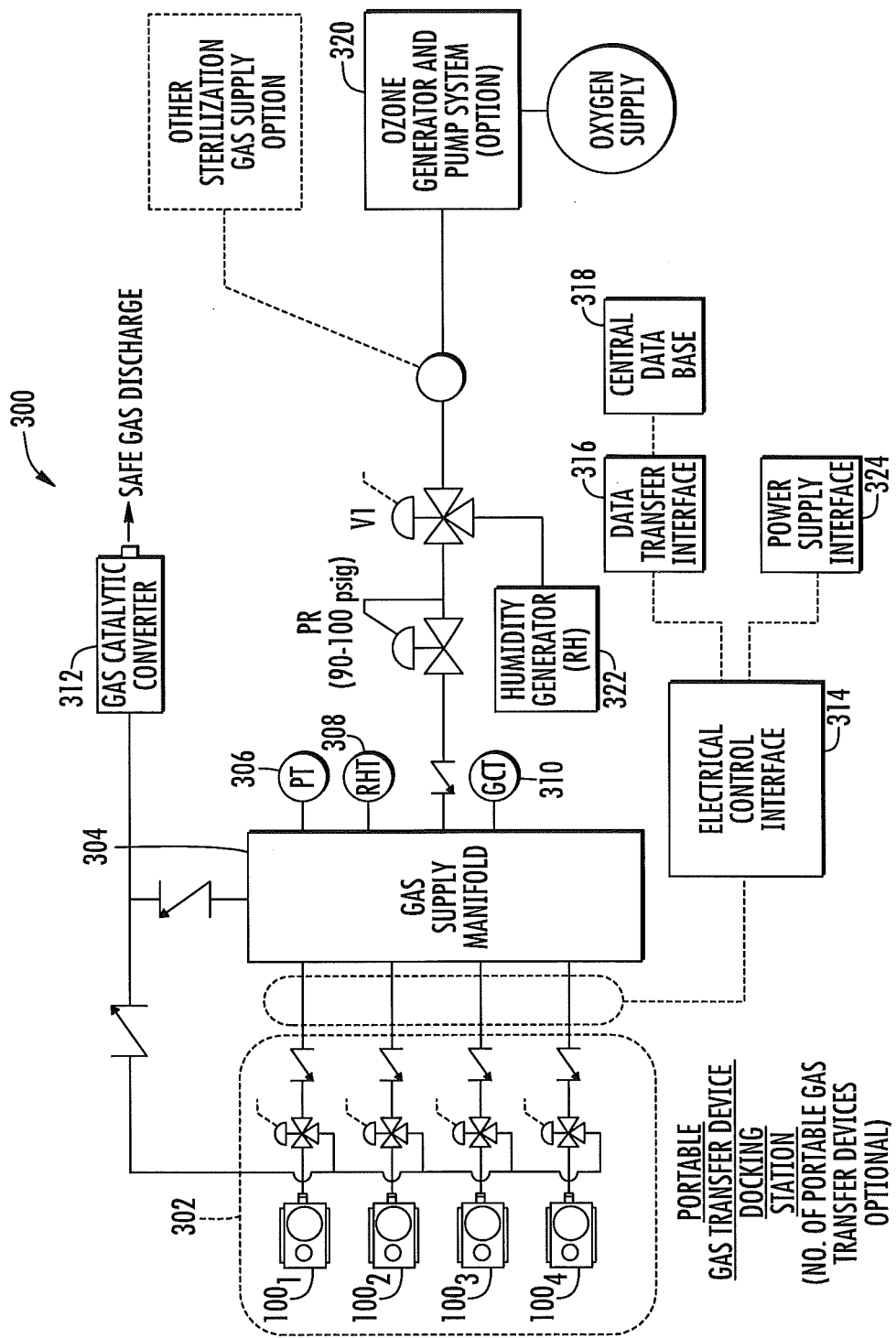
FIG. 31 is schematic illustrating a sterilization gas supply/refilling system for use with the portable gas transfer device of FIG. 12.

A sterilization gas supply/refilling system 300 according to some embodiments is illustrated in FIG. 31. The system 300 includes a portable gas transfer device docking station 302. The docking station has a plurality of docking areas, with each area configured to receive one of a plurality of portable gas transfer devices $100_1$, $100_2$, $100_3$, $100_4$. Although not illustrated, each docking area may include guide tracks to receive the portable gas transfer device guide bars 126 shown in FIG. 13. This configuration provides audible and/or tactile feedback that the portable gas transfer device has been properly seated in the docking area. Each docking area includes a gas supply connection for the gas refill supply valve 128 and an electrical connection for the electrical interface 130.

The portable gas transfer devices $100_1$, $100_2$, $100_3$, $100_4$ are refilled through the valve 128 with pressurized sterilization gas supplied from the gas supply manifold 304. Various transmitters may be integrated into the gas supply manifold 304, including a pressure transmitter (PT) 306, a relative humidity transmitter (RHT) 308, and/or a gas concentration monitor transmitter (GCMT) 310. Other sensors or transmitters may be incorporated as needed. Signals from the transmitters are fed to an electrical control interface system 314.

In some embodiments, the gas supply manifold 304 is supplied with an existing sterilization gas supply. Alternatively, a sterilization gas generation and/or supply system 320 may be provided to supply gas to the gas supply manifold 304. In the illustrated embodiment, the system 320 generates ozone gas from a separate oxygen supply. The system 320 pressurizes and supplies the gas to the manifold 304. Pressure levels (e.g., 90-100 psig) are controlled by a pressure regulator (PR).

In some embodiments, a relative humidity (RH) generating system 322 is provided. The effectiveness of certain sterilization gases in achieving a (log 6) pathogen kill rate is enhanced by increased RH levels. The RH system 322 may supply clean moisture (at a controlled RH) to sterilization gas steam, for example.

Certain sterilization gases (such as ozone) have relatively short "half-life" gas concentration reduction due to pressurization. As such, a gas catalytic converter system 312 may be provided; any portable gas transfer devices 100 that have been docked past the allowable "half-life" time limit may be discharged to the gas catalytic converter system 312. The gas catalytic converter system 312 converts harmful or toxic sterilization gases to a safe discharge gas. In the case of ozone ($O_3$), it is converted to ($O_2$) by the catalytic converter. The discharged portable gas transfer devices may then be refilled from the gas supply manifold system 304. Furthermore, unused sterilization gas from the gas supply manifold 304 may be directed to the gas catalytic converter system 312. These actions may all be controlled automatically from the electrical control interface system 314.

As noted above, the docking station 302 also includes an electrical connection for the electrical interface 130 of each portable gas transfer device 100. Each portable gas transfer device 100 includes at least one battery pack to provide power to various components (e.g., the display, the controller, etc.). The electrical connection at the docking station recharges the battery pack. In addition, the electrical connection transfers electronic validation data from the portable gas transfer devices to a central data base 318 via a data transfer interface 316.

Specifically, the data transfer interface 316 controls the transfer of electronic sterilization validation protocol data from the portable gas transfer devices to the main central data base 318. Each time a portable gas transfer device 100 sterilizes a single-use aseptic connection or joint in a bioprocess system, an electronic signature of the portable gas transfer device ID, the single-use connection ID, the operator ID (all described above in connection with the display 116), as well as the gas concentration per time (e.g., ppm of ozone/time) is stored on an EPROM in the portable gas transfer device controller. Other data such as relative humidity may also be included as each bio-process system warrants.

As indicated above, the electrical control interface 314 is the overall system control hub. It controls each subsystem function, sensor/transmitter monitoring, and data transfer to the central database computer. It is noted that, when the gas transfer devices are docked in the docking areas, they are effectively "reset" for future use. This includes not only refilling the pressurized gas canister, but also sending a signal to the solenoid 184 such that the pin 182 engages the opening 180 of the gas transfer member 150 (FIG. 22), for example.

A power supply/distribution system 324 system supplies the AC/DC power requirements of the overall system.

Pressurized gas, such as ozone, may be injected in a single-use connection site or joint in a number of ways. Examples include, but are not limited to: a gas syringe injection; a single-use valve system (e.g., the gas dispersion interconnect device 10 described above); a rotating gas dispersing tube; and a gas dispersing spray ball.

Figure 32:
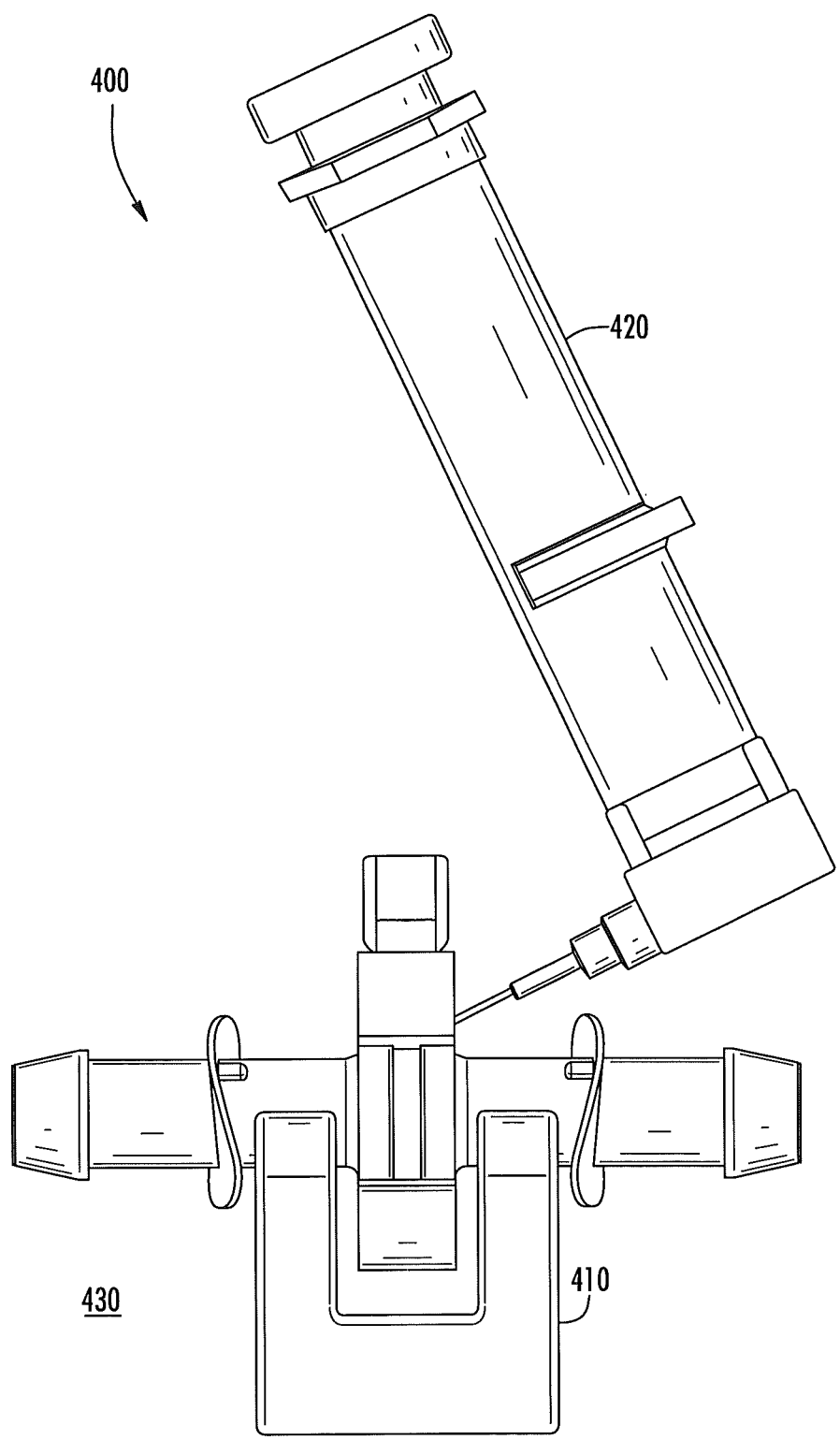
FIG. 32 is a front view of a sterilization apparatus according to some embodiments.

A sterilization apparatus 400 according to some embodiments is illustrated in FIG. 32. Generally, the sterilization apparatus 400 includes two portions: a sealable local environment 410 and a pressurized gas (e.g., ozone) source 420, the form and function of each of which are described in detail with reference to FIGS. 32-40. An aseptic connection point (not shown in FIG. 32), such as an open portion of a fluid path or two or more fluid flow components or connectors, may be received within the sealable local environment 410. Although the aseptic connection point may have been pre-sterilized, for purposes of this description, it is assumed that an ambient environment 430 may not be sufficiently sterile. Accordingly, to effect an aseptic connection, the aseptic connection point is received within the sealable local environment 410 which is then sealed against the ambient environment 430.

After the sealable local environment 410 is sealed, the ozone source 420 is used to introduce a supply of ozone (not shown in FIG. 32) into the sealable local environment 410. Exposure to the supply of ozone, for example at a predetermined concentration and for a predetermined duration, enables the sealable local environment 410 and the aseptic connection point therein to reach a predetermined sterilization level. As a result, an aseptic connection may be made within an ambient environment 430 that may not be sterile. The ozone source 420 may include a pneumatic injection device, such as a syringe, adapted to penetrate a membrane described with reference to FIG. 35 to introduce the supply of ozone into the interior of the sealable local environment 410. Alternatively, the ozone source 420 may include another type of pump or may include an ozone generator, such as a water electrolysis ozone generator. Alternatively, the ozone source 420 may take the form of the portable gas transfer device 100 described above or a similar device.

Figure 33:
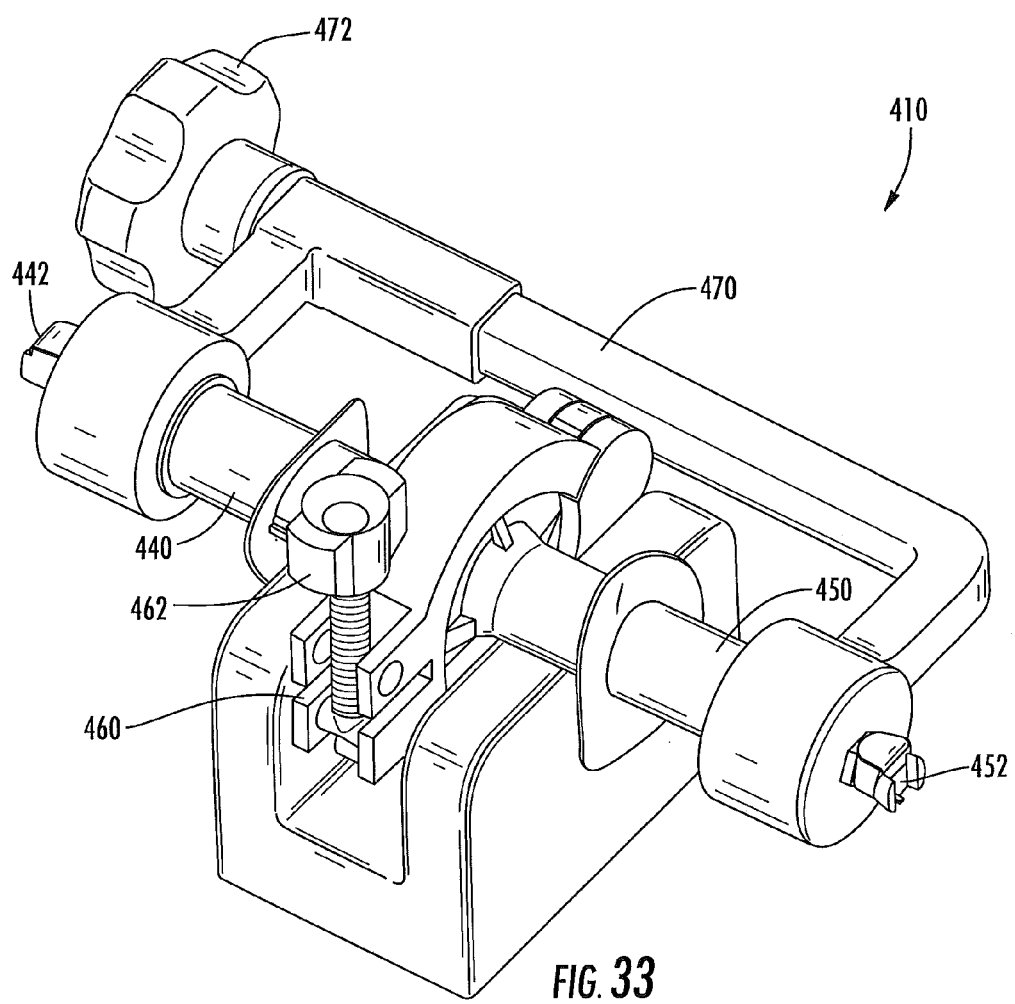
FIG. 33 is a perspective view of a sealable local environment of the apparatus of FIG. 32.

FIG. 33 is a perspective view of a sealable local environment 410 of the sterilization apparatus 400 of FIG. 32 in which the sealable local environment 410 includes a rigid structure. As further described with reference to FIG. 38, the sealable local environment may alternatively comprise a flexible body. The sealable local environment 410, shown in a closed position, may be configured to receive the aseptic connection point (not shown in FIG. 33) which, for sake of example, may include a pair of more fluid path connectors or fluid flow components (referred to below as "connectors"). As previously described, the connectors may be pre-sterilized but may need to be coupled in a non-sterile ambient environment 430 (FIG. 32). To allow the connectors to be aseptically coupled within the non-sterile ambient environment 430, each of the connectors may be received in chambers 440 and 450 of the sealable local environment 410. The chambers 440 and 450 may include openings 442 and 452, respectively, to enable connection lines (not shown in FIG. 33) to extend from the sealable local environment 410 to fluid lines or fluid sources (also not shown in FIG. 33) to which the connectors are coupled.

Once the connectors are in place in the sealable local environment 410, the sealable local environment may be sealed by securing a closure device 460. The closure device 460 may be in the form of a screw-driven closure that may be closed and secured by turning a knob 462. Once the connectors have been sterilized within the sealable local environment 410, as further described below, the sealable local environment 410 may be manipulated to enable the connectors enclosed therein to be coupled together while the sterile, sealable local environment 410 remains sealed. The sealable local environment 410 may include a manipulator 470, such as a screw-driven manipulator, that enables the chambers 440 and 450 of the sealable local environment to be drawn together without unsealing the sealable local environment 410. In some embodiments, an actuator 472, such as a knob, may be turned to drive the chambers 440 and 450 together so as to forcibly interconnect the connectors within the sterile, sealable local environment 410. Once the connectors have been interconnected, the closure device 460 may be released and the joined connectors (or other secured connection point) may be removed from the sealable local environment 410. The connection point may then be exposed to a potentially non-sterile environment without exposing the fluid path to contamination.

Figure 34:
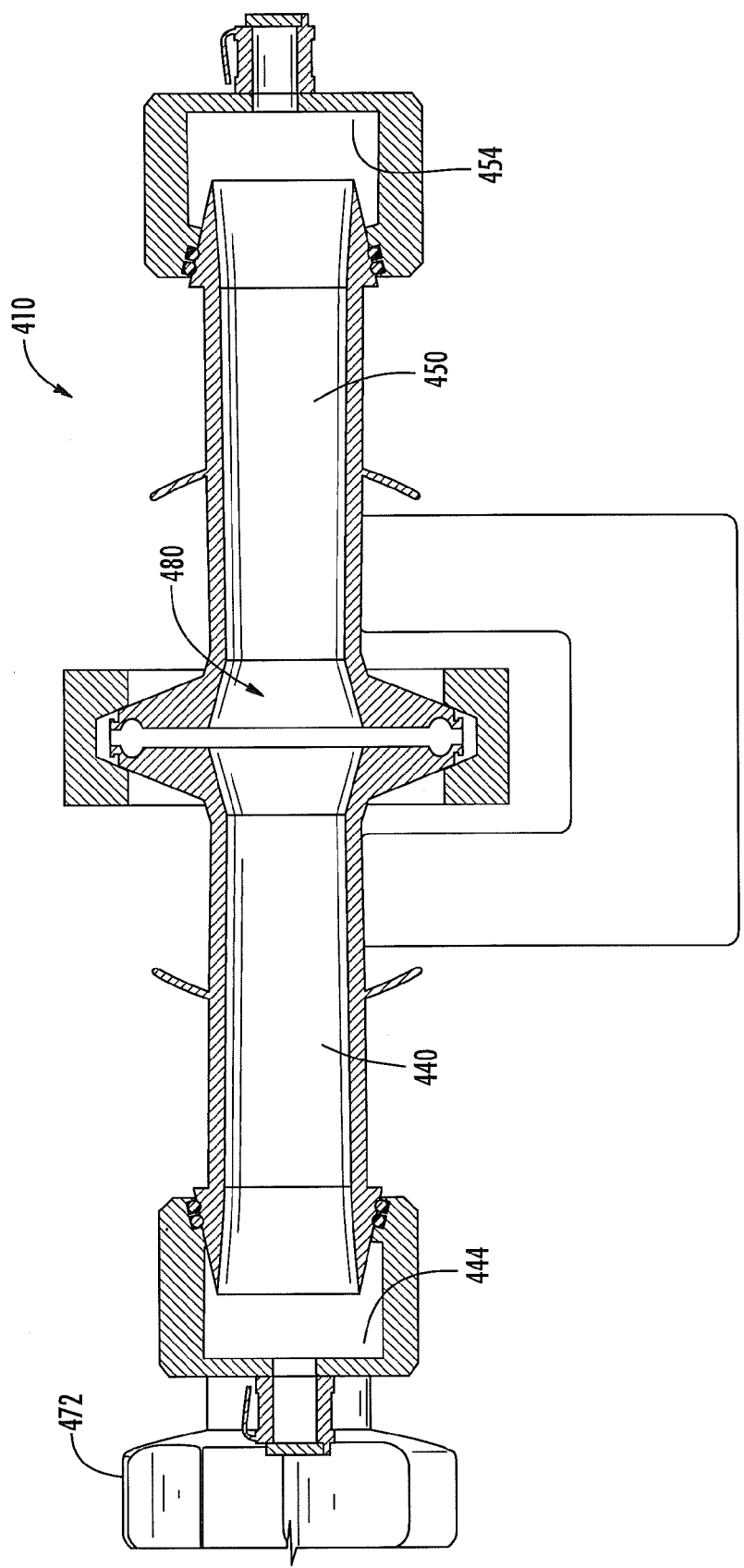
FIG. 34 is a cross-sectional front view of the sealable local environment of FIG. 33.

FIG. 34 is an internal cross-sectional view of the sealable local environment 410 of FIG. 33. As previously described with reference to FIG. 33, the sealable local environment 410 includes chambers 440 and 450 to receive parts of the connection point, such as a pair of fluid path connectors or fluid flow components (not shown in FIG. 34). The chambers 440 and 450 may include end portions 444 and 454, respectively, to forcibly engage portions of the fluid path connectors. By forcibly engaging ends of the fluid path connectors, when the actuator 472 is manipulated to drive the chambers 440 and 450 together, the fluid path connectors will be forcibly interconnected at a central point 480 of the sealable local environment 410. It is noted that, before the actuator 472 is manipulated to interconnect the fluid path connectors, the fluid path connectors or other connection point may not be joined together at the central point 480. As described with reference to FIG. 35, the supply of ozone or other gas is introduced near the central point 480 to facilitate sterilization of interior portions of the fluid path connectors or other connection point before the connection point is closed.

As previously described with reference to FIG. 33, once the aseptic connection has been made within the sealable local environment 410, the sealable local environment 410 may be unsealed and the aseptically sealed fluid path connectors or other connection point may be removed and exposed to the ambient environment without risk of contamination of the fluid path.

Figure 35:
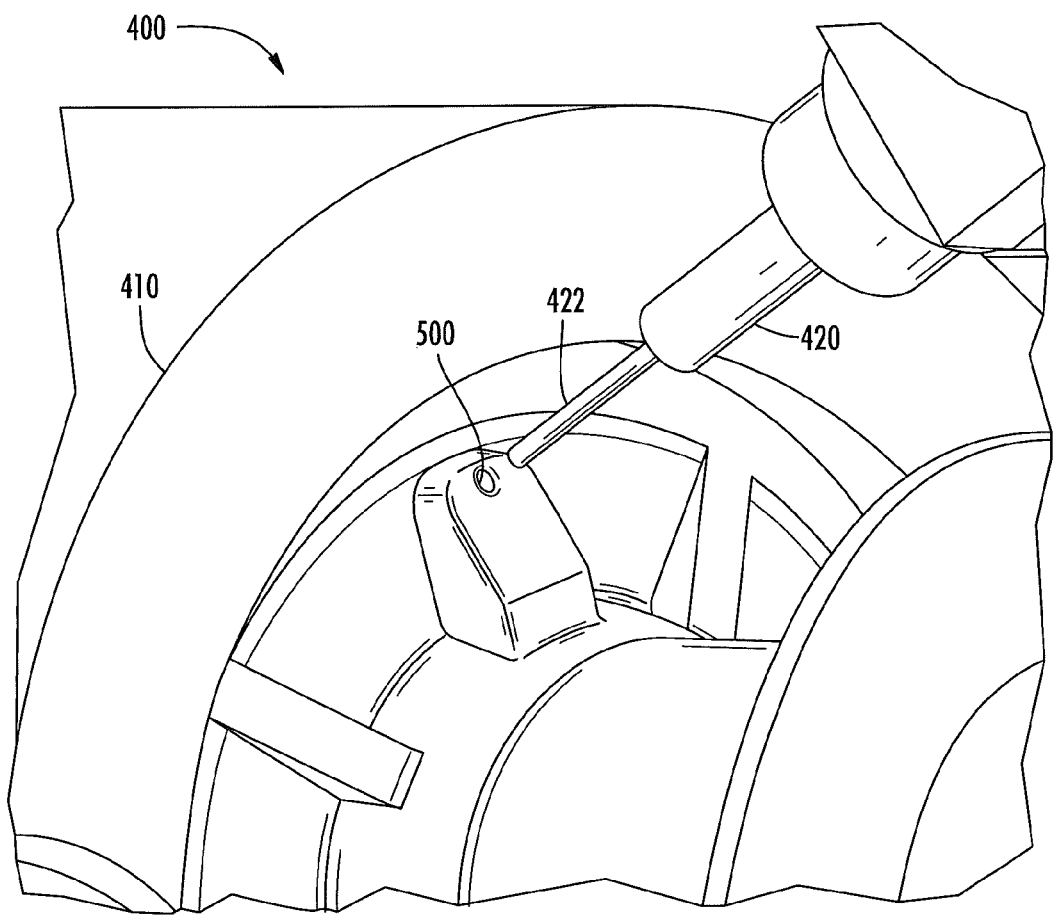
FIG. 35 is an enlarged perspective view of the sealable local environment of FIG. 33 showing a membrane configured to receive a pressurized gas source.

FIG. 35 is a perspective view of the sterilization apparatus 400 of FIG. 32 showing a membrane 500 in the sealable local environment 410 configured to receive a supply of ozone (not shown) from the ozone source 420. As previously described with reference to FIG. 34, according to some embodiments, the membrane 500 is near the central point 480 (FIG. 34) of the sealable local environment 410 so that the supply of ozone may reach interior portions of the fluid path connectors or other connection point to sterilize interior portions of the connection point that may engage the fluid within.

In some embodiments, the membrane 500 may define a small opening sized to closely engage sides of a needle or other injection member 422 of the ozone source 420. Having the membrane 500 and the injection member 422 closely match in size may prevent leakage at the membrane 500. The membrane 500 may be comprised of a penetrable material to enable the injection member 422 to penetrate the membrane 500 while the membrane sealingly engages sides of the injection member 422. As previously described with reference to FIG. 32, the ozone source may include a pneumatic device, such as a syringe or other pump. Alternatively, the ozone source may include an ozone generator that is securable to the membrane 500 or a similar port formed in the sealable local environment 410 to receive the supply of ozone. An exemplary "ozone generator" is the portable gas transfer device 100 described above.

Figure 36:
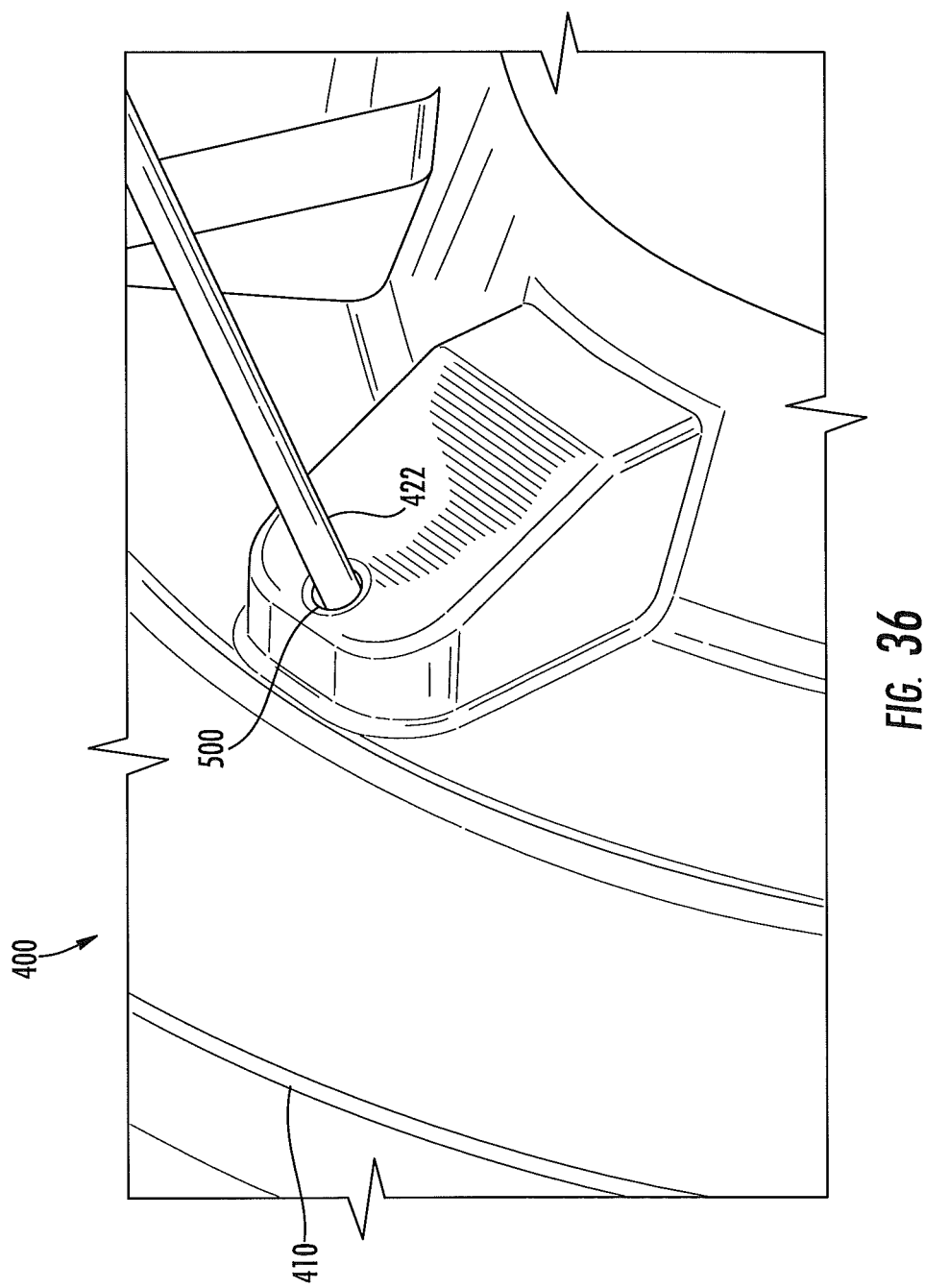
FIG. 36 is an enlarged perspective view of the sealable local environment of FIG. 35 showing the pressurized gas source inserted into or past the membrane.

FIG. 36 is another perspective view of the sterilization apparatus 400 of FIG. 32 showing the ozone source 420 upon insertion into the membrane 500. As previously described, the injection member 422 may penetrate and puncture the membrane 500, facilitating a tight seal between the membrane 500 and the injection member 422. In some embodiments, the tight seal between the membrane 500 and the injection member 422 prevents microbial contamination of the interior of the sealable local environment 410 while containing the supply of ozone within the interior of the sealable local environment 410.

Figure 37:
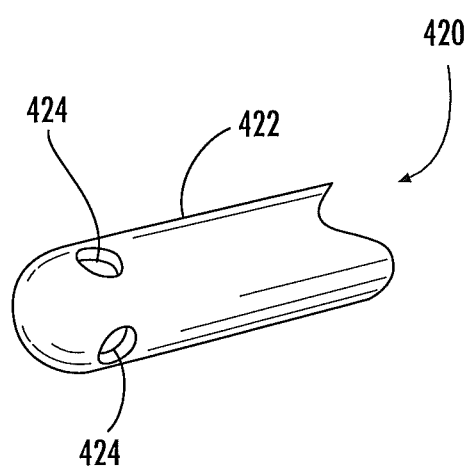
FIG. 37 is an enlarged perspective view of an injection member of the pressurized gas source of FIG. 35.

FIG. 37 is a cutaway view of the ozone source 420 showing details of the injection member 422 according to some embodiments. In some embodiments, the sealable local environment 410 permits the injection member 420 to be inserted into the sealable local environment 410 to a depth sufficient to enable one or more orifices 424 of the injection member 422 to enter into the sealable local environment 410. The supply of ozone (not shown) is presented into the sealable local environment 410 through the orifices 424.

In some embodiments, after sterilization, the supply of ozone may be captured from the sealable local environment 410 prior to unsealing the sealable local environment. The captured ozone may thus be stored or disposed of as desired. For example, the captured supply of ozone may be passed through a catalytic converter to convert the ozone to oxygen, and then released.

Figure 38:
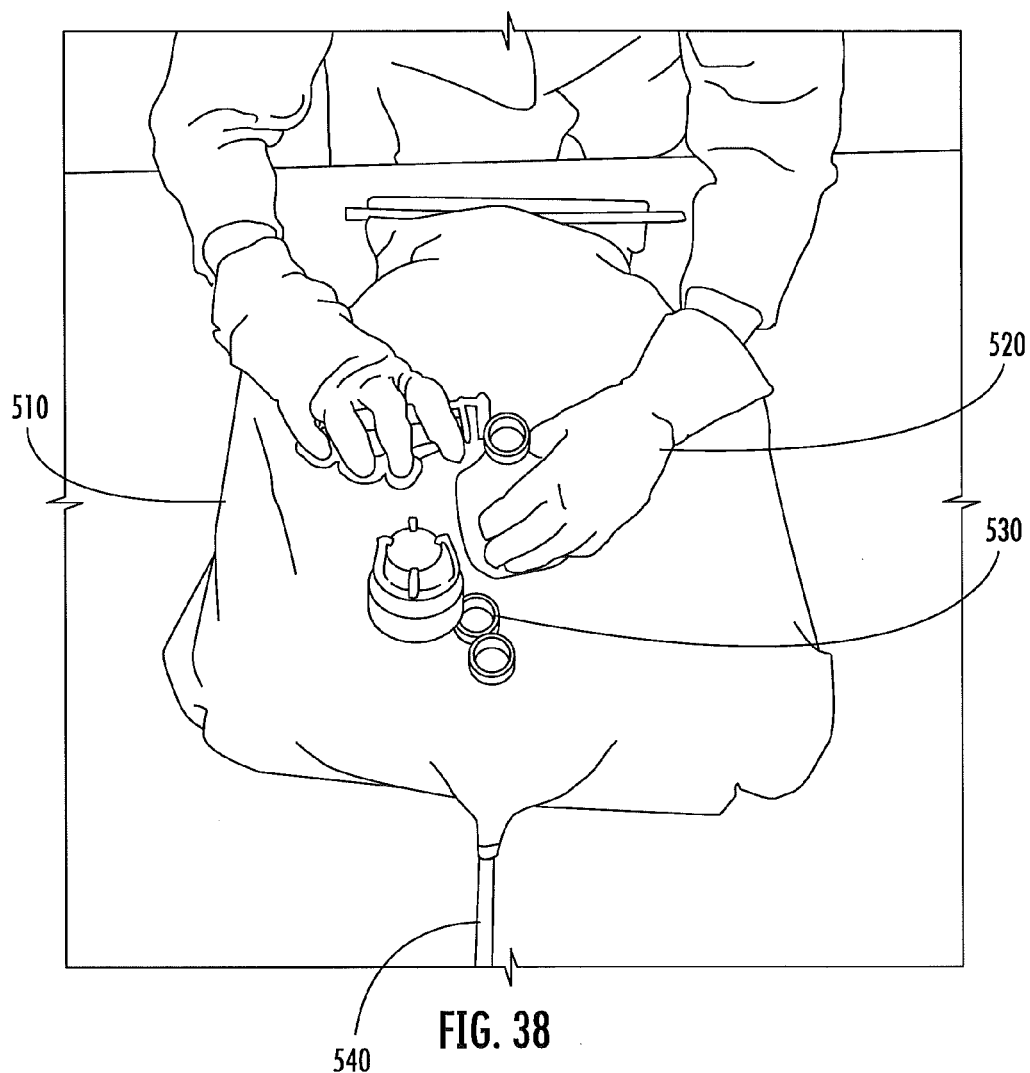
FIG. 38 is a top perspective view of a sterilization apparatus according to other embodiments.

FIG. 38 is a top perspective view of a sterilization apparatus according to other embodiments in which a sealable local environment 510 comprises a flexible body. The sealable local environment 510 may be in the nature of a glove box that includes flexible openings in a more rigid shell to receive a user's hands 520. Alternatively, the sealable local environment 510 overall may include a flexible body allowing the user's hands 520 to manipulate the sealable local environment 510 to enable connection of fluid path connectors or fluid flow components or some other connection point within a sterile sealable local environment 510. The sealable local environment 510 may include one or more membranes or other orifices 530 to receive an ozone source (not shown in FIG. 38). The sealable local environment 510 also may include one or more outlets 540 to enable fluid lines coupled to the fluid path connectors or other connection point to extend outwardly through sides of the sealable local environment 510.

Figure 39:
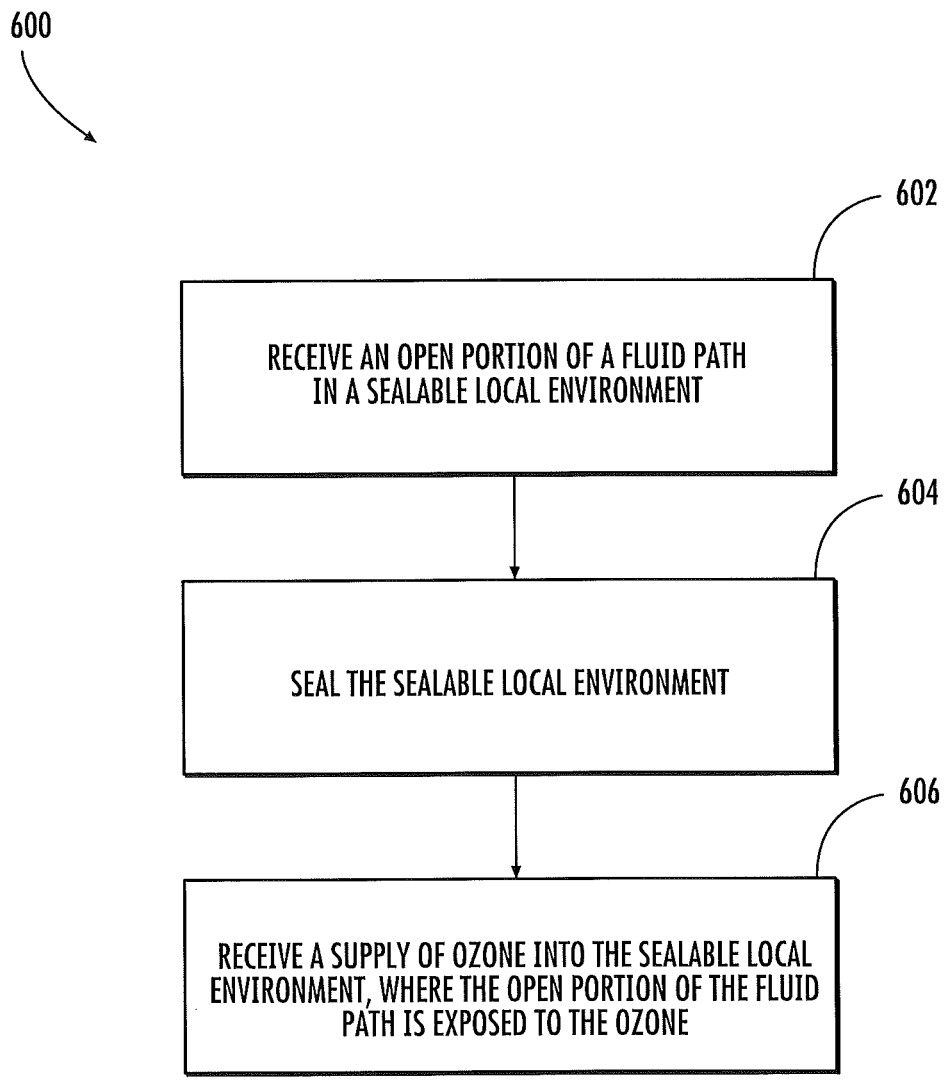
FIG. 39 is a flow diagram of a method of sterilizing an open portion of a fluid path according to some embodiments.

FIG. 39 is a flow diagram of a method 600 of sterilizing an open portion of a fluid path according to some embodiments. At block 602, an open portion of a fluid path is received in a sealable local environment. As previously described with reference to FIG. 34, for example, the open portion of the fluid path may include fluid path connectors to be interconnected in a potentially non-sterile environment. The sealable local environment 410 may be opened and the fluid path connectors may be inserted within the sealable local environment 410. At block 604, the sealable local environment is sealed. As described with reference to FIG. 33, the sealable local environment 410 may be sealed through the use of a closure device 460. At block 606, a supply of ozone is received into the sealable local environment, where the portion of the fluid path is exposed to the ozone. As described with reference to FIGS. 34-37, for example, an ozone source, such as a syringe or other pneumatic device or an ozone generator may be coupled to the sealable local environment 410 and a supply of ozone thus may be introduced into the sealable local environment 410. As also previously described, by introducing the supply of ozone into the sealable local environment before the fluid path connectors are interconnected, the fluid path is exposed to and sterilized by the ozone.

Figure 40:
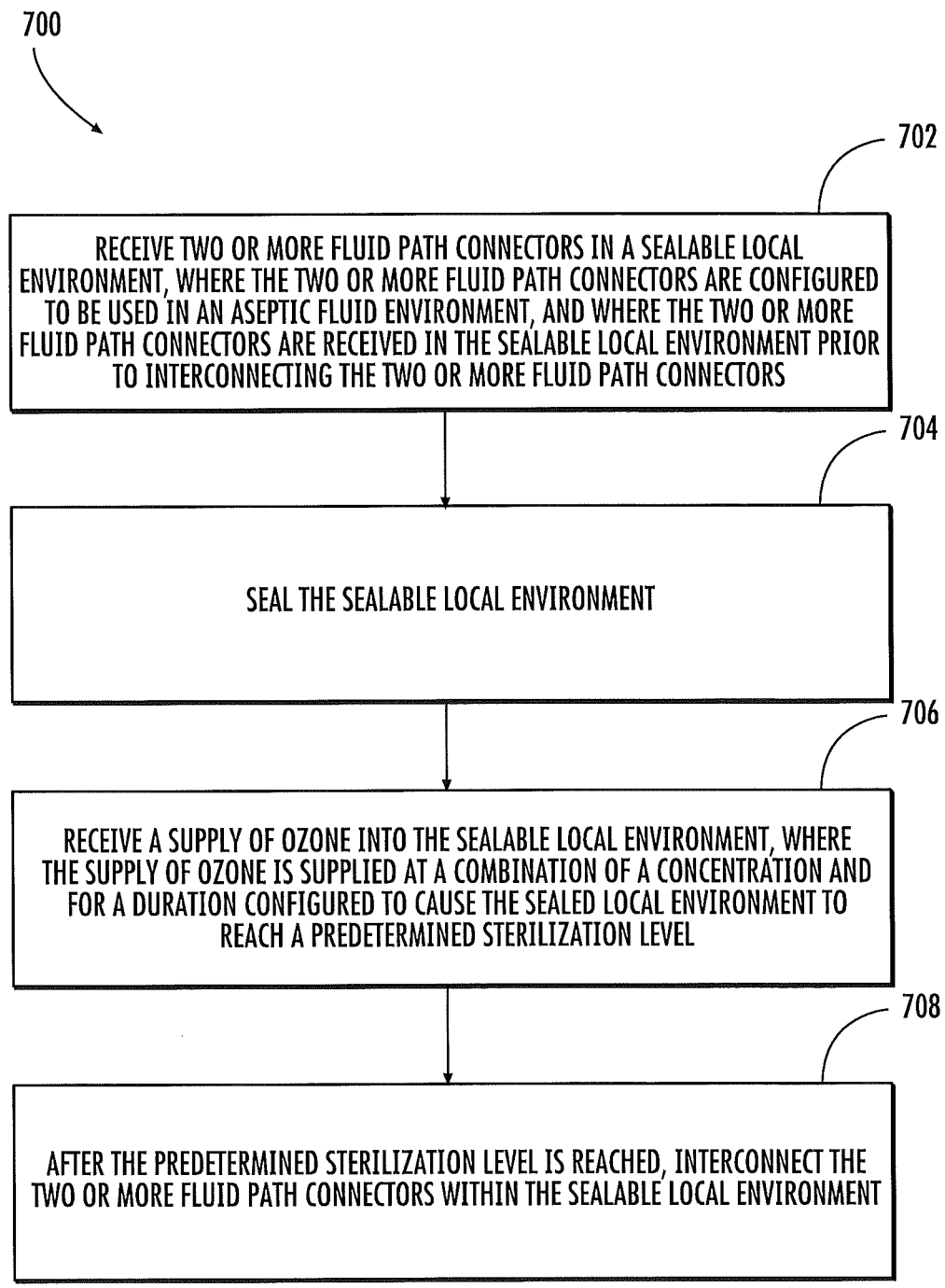
FIG. 40 is a flow diagram of a method of sterilizing two or more fluid path connectors according to some embodiments.

FIG. 40 is a flow diagram of a method 700 of sterilizing an open portion of a fluid path according to some embodiments. At block 702, two or more fluid path connectors are received in a sealable local environment, where the two or more fluid path connectors are configured to be used in an aseptic fluid environment, and where the two or more fluid path connectors are received in the sealable local environment prior to interconnecting the two or more fluid path connectors. As previously described with reference to FIG. 34, the two or more fluid path connectors may need to be interconnected in a potentially non-sterile environment. The sealable local environment 410 may be opened and the fluid path connectors may be inserted within the sealable local environment 410. At block 704, the sealable local environment is sealed. As described with reference to FIG. 33, the sealable local environment 410 may be sealed through the use of a closure device 460.

At block 706, a supply of ozone is received into the sealable local environment, where the supply of ozone is supplied at a combination of a concentration and for a duration configured to cause the sealable local environment to reach a predetermined sterilization level. As described with reference to FIGS. 34-37, for example, an ozone source, such as a syringe or other pneumatic device or an ozone generator may be coupled to the sealable local environment 410 and a supply of ozone thus may be introduced into the sealable local environment 410. As also previously described, by introducing the supply of ozone into the sealable local environment before the fluid path connectors are interconnected, the fluid path is exposed to and sterilized by the ozone. The concentration of ozone may be calculated based on the duration for which the fluid path connectors are to be exposed or based on the ozone source selected. At block 708, after the predetermined sterilization level is reached, the two or more fluid path connectors are interconnected within the sealable local environment. As described with reference to FIGS. 33 and 34, in a rigid sealable local environment 410, a manipulator or actuator 472 may be used to forcibly interconnect the fluid path connectors within the sealable local environment. As described with reference to FIG. 38, when the sealable local environment includes a flexible body, a user may manipulate the flexible body to interconnect the fluid path connectors.

Although the component 420 is described herein as an ozone source, it is contemplated that the component 420 could be a source of other pressurized gas/vapor, including low-temperature gas/vapor sterilants such as, but not limited to: ethylene oxide (EO or EtO), vaporized hydrogen peroxide (VHP or HPV), hydrogen peroxide gas plasma, vaporized formaldehyde, gaseous chlorine dioxide and vaporized peracetic acid.

It is noted that the ozone source 420 (or other pressurized gas/vapor source) could be used in connection with the gas dispersion device 10 described above or a similar device. For example, referring to FIG. 1, the ozone source 420 could be inserted into the gas supply port 30. A membrane similar to the membrane 500 could be positioned at or near the gas supply port 30, and the membrane could receive the ozone source injection member 422 therethrough. Thus, the gas dispersion device 10 may be used with other pressurized gas/vapor sources, such as a syringe. The gas dispersion device 10 may provide advantages as the internal portions of the interconnected process connection or joint, or fluid flow components attached to the gas dispersion device 10, need not be disconnected and exposed to an ambient and potentially non-sterile atmosphere after sterilization and before a fluid, such as bioprocessing fluid, flows therethrough.

Figure 41:
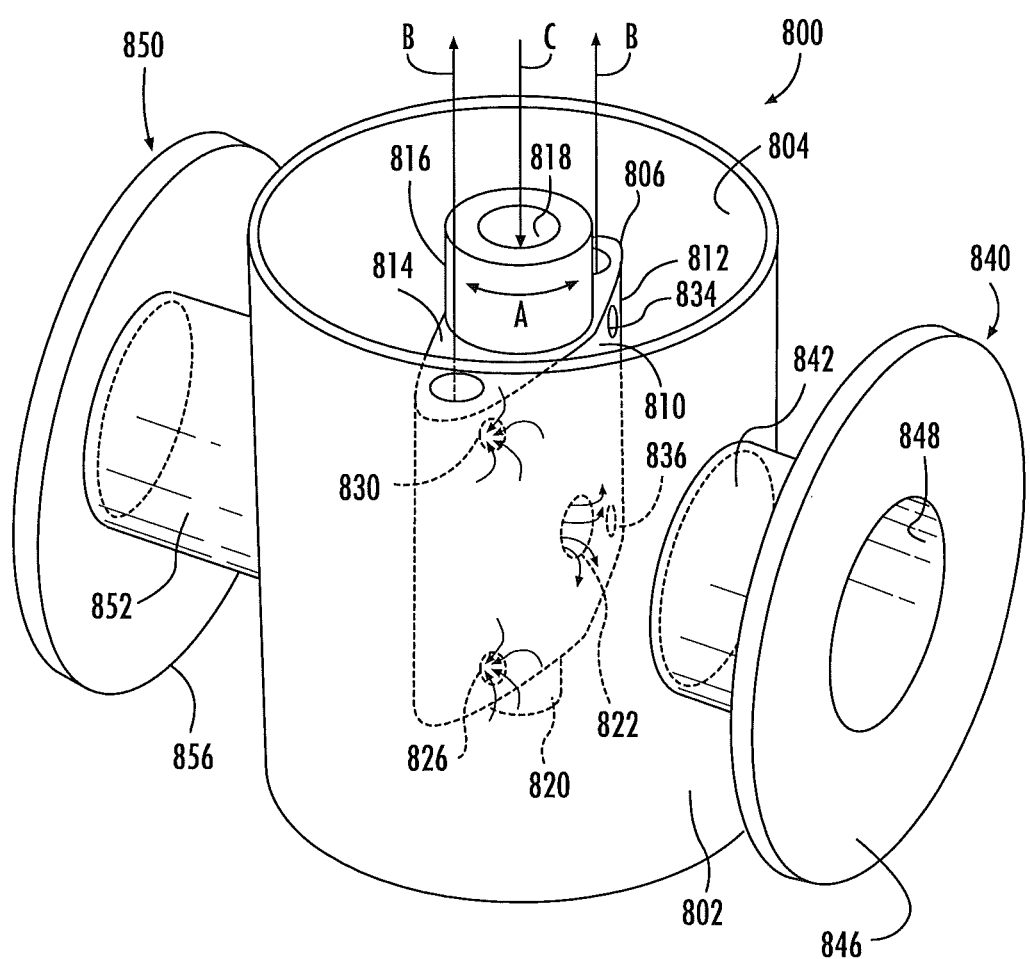
FIG. 41 is a schematic perspective view of a gas dispersion device according to other embodiments.
Figure 42:
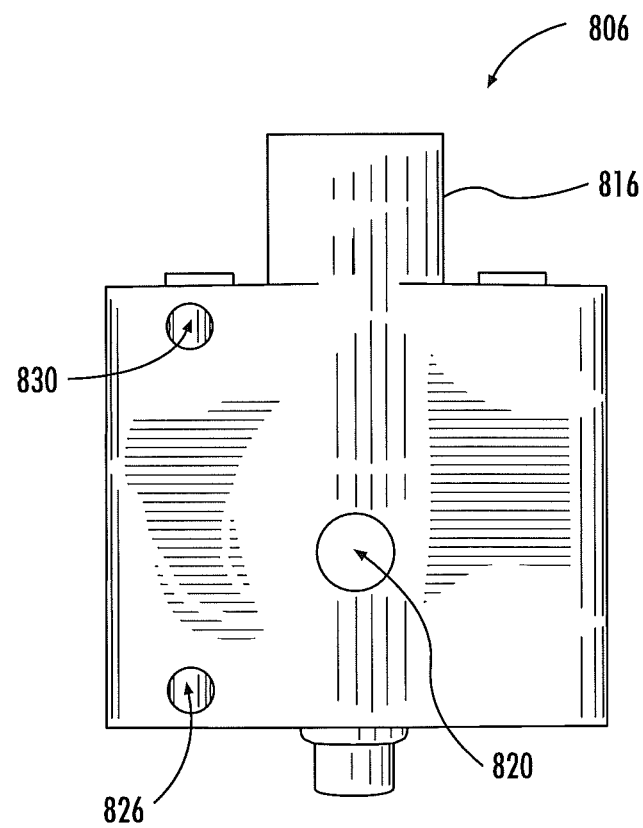
FIG. 42 is a front elevation view of a valve element of the gas dispersion device of FIG. 41.
Figure 43:
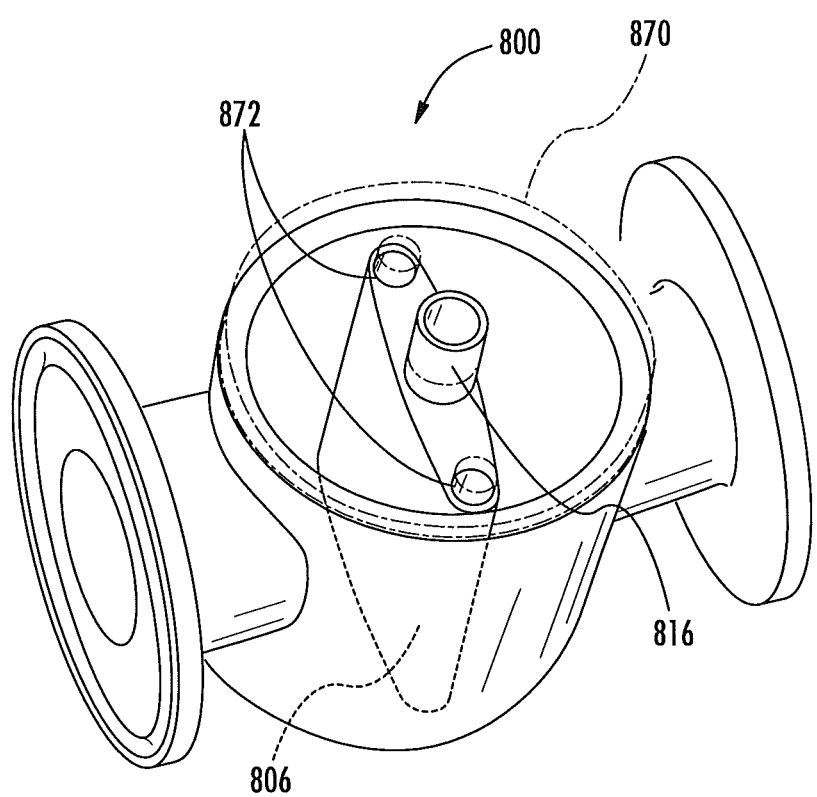
FIG. 43 is a top perspective view the gas dispersion device of FIG. 41.

A gas interconnect dispersion device 800 according to some other embodiments is illustrated in FIGS. 41-43. The gas dispersion device 800 is similar to the gas dispersion device 10; however, the gas dispersion device 800 includes a rotatable gas flow member rather than a retractable gas flow member. Other differences between the gas dispersion devices 10 and 800 will be apparent from the description below.

The gas dispersion interconnect device 800 shown in FIG. 41 includes a cylindrical valve body 802 defining a valve cavity 804 therein, in which is disposed a butterfly valve element 806 (e.g., a rotatable gas flow member). The interconnect device 800 includes a first inlet/discharge port assembly 840 including inlet/discharge conduit 842, and connection flange 846 having central opening 848 therein communicating with the interior bore of conduit 842. The bore in conduit 842 communicates with the interior volume of the valve cavity 804.

In like manner, the interconnect device 800 includes a second inlet/discharge port assembly 850, comprising inlet/discharge conduit 852 coupled to connection flange 856 having an inlet/discharge opening that communicates with the bore of conduit 852. The bore in conduit 852 communicates with the interior volume of valve cavity 804.

The butterfly valve element 806 includes a cylindrical collar 816 having an open bore 818 therein communicating with an interior passage (not shown) in the main body portion 810 of the valve element. The main body portion as shown has a top surface 814 containing gas discharge ports at its lateral portions, by which previously used sterilization gas (e.g., ozone gas) can be discharged from the valve in the direction indicated by arrows B.

Depending downwardly from the main body portion 810 is a lower collar member 820, which may be journaled or otherwise secured in the valve assembly, being coaxial with the upper collar member 816, whereby the valve in operation can be bi-directionally rotated in the directions indicated by the bi-directional arrow A.

The butterfly valve 806 is shaped so that it has a cross-sectional profile that is taperingly convergent from the central axis defined by collar members 816 and 820, to the lateral edges 812 of the valve element. The main body 810 of the valve element thus may have a flattened or flap-like character.

The main body 810 of the butterfly valve 806 has a central opening extending transversely through the main body 810 (transverse to the central axis of the valve element, as defined by the center line of the valve element extending longitudinally through the main body 810 and upper collar 816 and lower collar 820) and outwardly from the respective faces of the valve element. The transverse dispersion opening 822 communicates by an interior passage (not shown in FIG. 41) with the bore 818 of upper collar 816, so that ozone gas introduced into the bore 818, in the direction indicated by arrow C, flows through the upper collar 816 and the internal passage of main body 810 and is discharged at both faces of valve element from the transverse opening 822 into the valve cavity 804, so that the dispersed sterilant fluid is thereafter distributed throughout the valve cavity 804 and passages in conduits 842 and 852.

Such gas introduction can be carried out so that the gas dispersion interconnect device 800 that is coupled with flow circuitry elements at each of the flanges 846 and 856, e.g., to tubing, piping, conduits, or other flow passage structure or fluid flow components achieves a sterile connection.

The main body 810 of the valve element 806 is also provided with lateral gas return ports 826 and 830 on one face of the main body (on the front face of the valve element in the view shown in FIG. 41), with lateral gas return ports 834 and 836 on the opposite face and opposite marginal portion of the valve element 806 (i.e., the right-hand marginal portion on the back face of the valve element in the view shown in FIG. 41).

The front face gas return ports 826 and 830 in the view shown communicate with the return gas discharge port at the top face 814 at the left-hand portion thereof, and the return gas ports 834 and 836 communicate with the return gas discharge port at the right-hand portion of the top surface 814 of the valve element 806.

In this manner, each of the front and rear main faces of the butterfly valve element 806 present gas return discharge port openings communicating with interior passages in the main body 810, so that gas following contact with interior surfaces of the valve chamber and associated flow circuitry structure enters the gas return port openings, flows through the interior passage structure of the valve element and is discharged from the valve at the gas discharge ports on the top surface 814 of the valve element, flowing in the direction indicated by arrows B in FIG. 41.

The valve element 806 may be rotatable as shown by the arrow A between a sterilization position and a product flow position. In the sterilization position, the dispersion opening 822 may be aligned or generally aligned with the bores of the conduits 842, 852. In the product flow position, the valve element 806 may be rotated (e.g., by 90 degrees or about 90 degrees) so as to provide additional fluid flow space in the valve cavity 804.

FIG. 42 is a front elevation view of the valve element 806. As illustrated, the dispersion opening 822 extends through the body of the valve element. The dispersion opening 822 is configured to rapidly disperse "pre-sterilization" pressurized gas received from the upper collar bore 818 in the direction C (FIG. 41). Also shown are gas return openings or ports 826, 830. The gas return openings 826, 830 are configured to receive "post-sterilization" gas, which is then directed upward in the direction B (FIG. 41). Gas return openings 834, 836 (FIG. 41) are disposed on the opposite side of the valve element 806 and are not visible in FIG. 42.

As shown in FIGS. 41 and 43, at least a portion of the valve element 806 may be contained in the valve cavity 804 by a lid 870. The lid 870 may include openings or ports 872 that may be aligned with the gas discharge openings at the valve element top surface 814. The upper collar 816 may extend upwardly past the lid 870.

The gas dispersion device 800 may be configured to receive a device similar to the portable gas transfer device 100 described above which may supply pressurized gas to the gas dispersion device 800 and/or may receive discharged post-sterilization gas from the gas dispersion device 800. Further, the ozone source 420 of FIG. 32 (or other pressurized gas/vapor source) could be used in connection with the gas dispersion device 800 or a similar gas dispersion device. For example, referring to FIG. 41, the ozone source 420 could be inserted into the upper collar bore 818. A membrane similar to the membrane 500 (FIG. 35) could be positioned at or near the upper collar bore 818, and the membrane could receive the ozone source injection member 422 therethrough. Thus, the gas dispersion device 800 may be used with other pressurized gas/vapor sources, such as a syringe.

Figure 45:
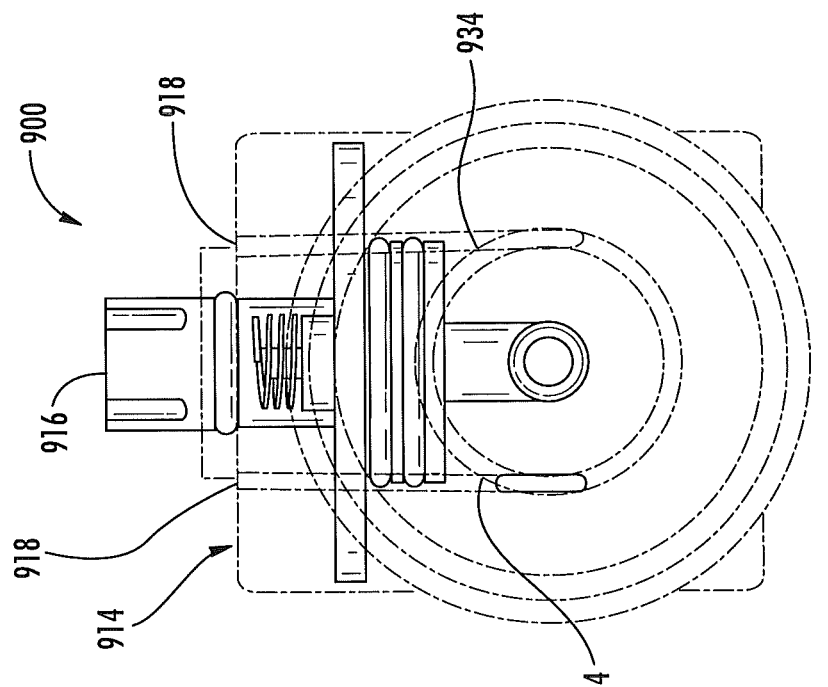
FIG. 45 is a transparent end view of the gas dispersion device of FIG. 44.
Figure 44:
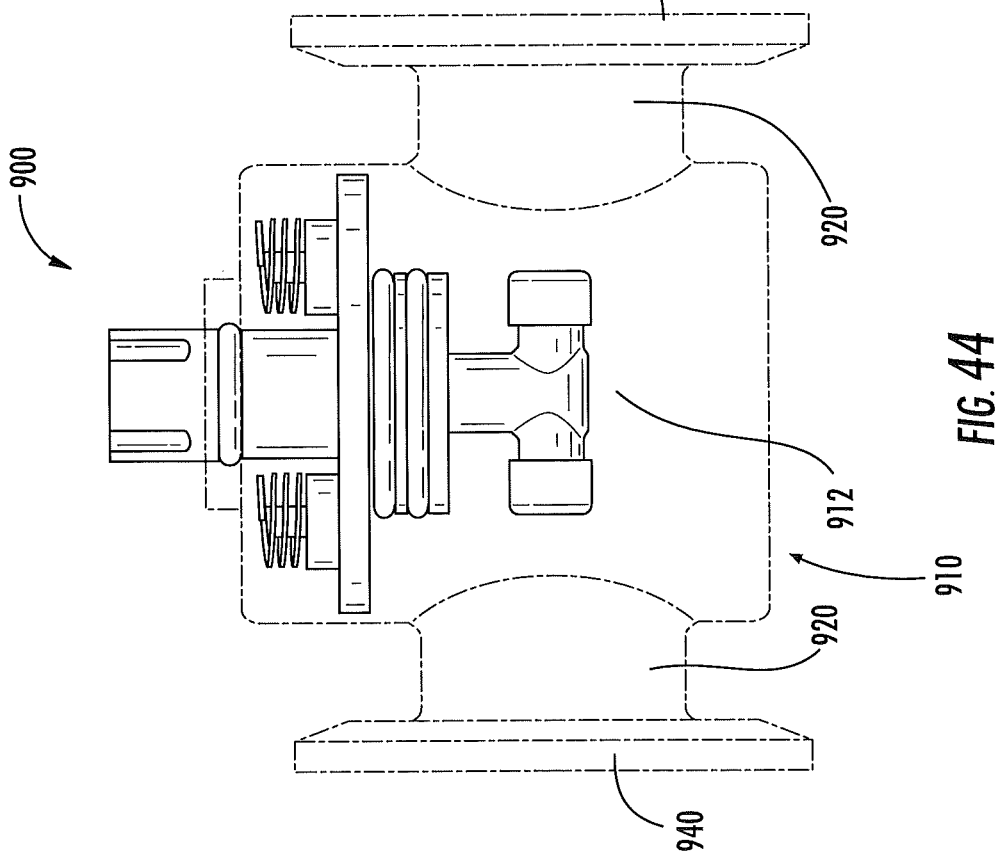
FIG. 44 is a transparent side view of a gas dispersion device according to other embodiments.
Figure 46:
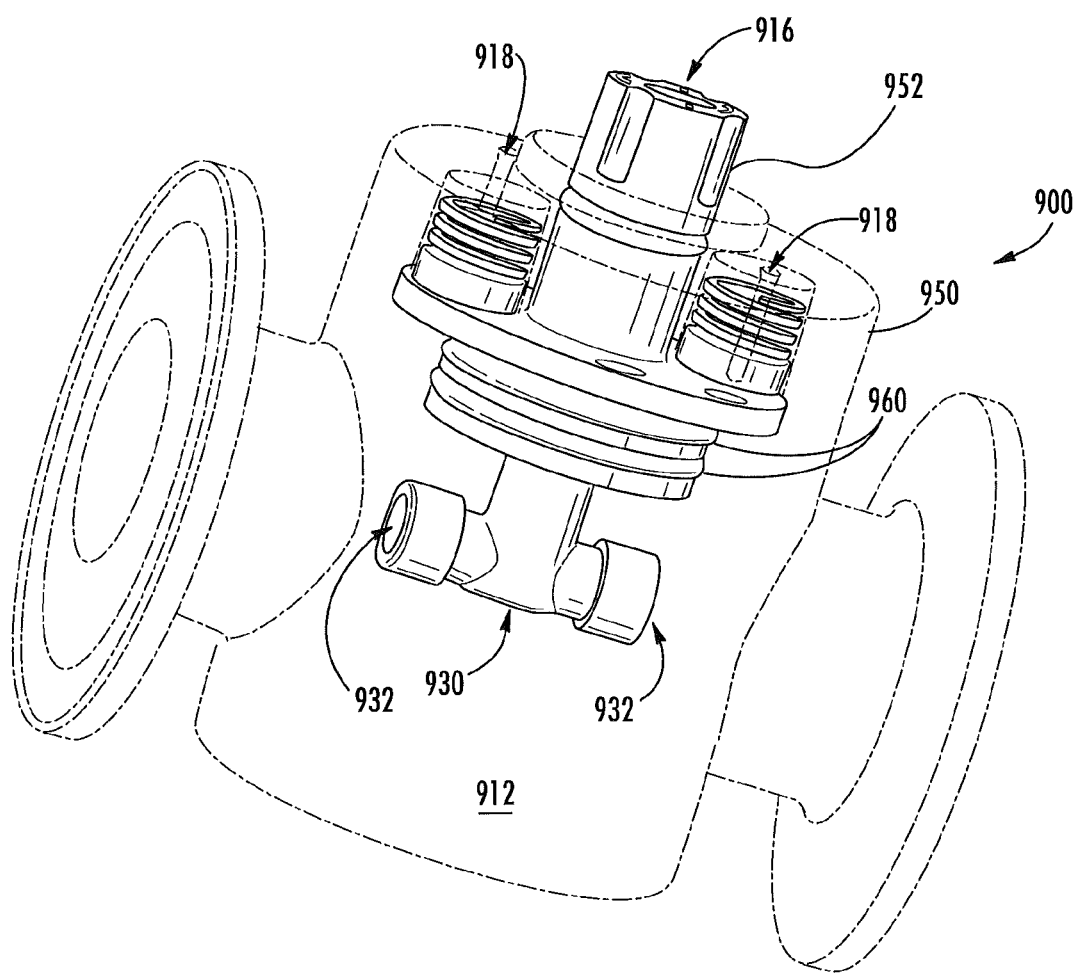
FIG. 46 is an enlarged perspective view of the gas dispersion device of FIG. 44.

A gas interconnect dispersion device 900 according to some other embodiments is illustrated in FIGS. 44-46. The device includes a housing 910, with the housing defining an internal cavity or chamber 912. A top portion 914 includes a gas inlet port 916 and a pair of gas outlet ports 918. Two flow conduits 920 are in fluid communication with the chamber 912, with each of the conduits 920 extending away from the chamber 912 at different sides of the housing 910. The housing may be generally cylindrical in shape, and the conduits 920 may be diametrically opposed.

A rotatable gas flow tube assembly 930 (FIG. 46) is at least partially disposed within the chamber 912. The rotatable tube assembly 930 includes a pair of dispersion openings 932 in fluid communication with the gas inlet port 916. The dispersion openings 932 are configured to effectively and rapidly disperse pressurized "pre-sterilization" gas received from the gas inlet port 916 throughout the chamber 912 and through the conduits 920. The rotatable tube assembly 930 is rotatable between a sterilization position and a product flow position, as described in more detail below.

The device 900 also includes a pair of return tubes 934 (FIG. 45) at least partially disposed within the chamber 912. Each return tube 934 is in fluid communication with a respective gas outlet port 918. The tubes 934 are configured to receive "post-sterilization" gas; as described above, "post-sterilization" gas means gas that has already been dispersed and sterilized various components and/or has sterilized various components to a Sterile Assurance Level (SAL) of $10^{-6}$. The ends or tips of the tubes 934 disposed in the chamber 912 may be beveled, as best seen in FIG. 45.

Like the devices 10 and 800 described above, the device 900 is connectable or operatively connectable to various components, such as connectors, fittings, flow passageways and sensors/transmitters (e.g., fluid flow components), via the conduits 920. Specifically, a distal end portion of each conduit 920 is configured to connect or operatively connect with at least one fluid flow component. As illustrated, the distal end portion of each conduit 920 includes a flange 940 to accommodate connection with such components, such as by a sanitary clamp. When the device 900 is connected to fluid flow components, the rotatable tube dispersion openings 932 are configured to disperse gas received from the gas inlet port 916 through or past the conduits 920 and adjacent or past the fluid flow components to sterilize these components (e.g., to achieve a SAL of $10^{-6}$ for these components).

In some embodiments, at least a portion of the housing 910, the conduits 920 and the flanges 940 form a monolithic structure. The rotatable tube assembly 930 may include a T-shaped member that defines the dispersion openings 932. The rotatable tube assembly 930 may be at least partially enclosed within the chamber 912 by a lid 950. Extending from or through the lid 950 is a collar 952 that defines the gas inlet port 916. The lid 950 may also include through-holes that align with the gas outlet ports 918. As illustrated, the rotatable tube assembly 930 and/or the lid 950 include one or more o-rings or other seals to effectuate a seal between the various components and to hinder the passage of pre- or post-sterilization gas or other fluid (e.g., bioprocessing fluid).

In some embodiments, the lid 950 is ultrasonically sealed or welded to the housing 910. Again, the rotatable tube assembly 930 is free to rotate from a sterilization position to a product flow position (a rotation of approximately 90 degrees).

FIG. 45 illustrates the gas dispersion interconnect device 900 wherein the rotatable tube assembly 930 is in the sterilization position. It can be seen that the dispersion opening 932 is aligned with and substantially centered with the bore of the conduit 920 to provide effective dispersion and sterilization.

After components connected or operatively connected to the gas dispersion device 900 have been adequately sterilized (i.e., to an SAL of $10^{-6}$), the rotatable tube assembly 930 may be rotated 90 degrees or about 90 degrees to a product flow position and bioprocessing fluid may pass through the conduits 920 and/or the chamber 912 of the gas dispersion device. Bioprocessing fluid passes through the sterilized path and past the sterilized flow components so that it can be measured and/or transferred with little to no contamination. In the product flow position, the dispersion openings 932 may be sealed by sidewalls of the housing 910 or chamber 912.

The gas dispersion device 900 may be configured to receive a device similar to the portable gas transfer device 100 described above which may supply pressurized gas to the gas dispersion device 900 and/or may receive post-sterilization gas from the gas dispersion device 900. Further, the ozone source 420 of FIG. 32 (or other pressurized gas/vapor source) could be used in connection with the gas dispersion device 900 or a similar gas dispersion device. For example, referring to FIG. 45, the ozone source 420 could be inserted into the gas inlet port 916. A membrane similar to the membrane 500 (FIG. 35) could be positioned at or near the gas inlet port 916, and the membrane could receive the ozone source injection member 422 therethrough. Thus, the gas dispersion device 900 may be used with other pressurized gas/vapor sources, such as a syringe.

It will be understood that various components or features of the gas dispersion interconnect devices 10, 800 and 900 may be combined. By way of example, the rotatable tube assembly 930 of the device 900 may also be retractable. By way of further example, the extendable/retractable gas flow member 24 of the gas dispersion device 10 may also be rotatable.

Many alterations and modifications may be made by those having ordinary skill in the art, given the benefit of present disclosure, without departing from the spirit and scope of the invention. Therefore, it must be understood that the illustrated embodiments have been set forth only for the purposes of example, and that it should not be taken as limiting the invention as defined by the following claims. The following claims, therefore, are to be read to include not only the combination of elements which are literally set forth but all equivalent elements for performing substantially the same function in That which is claimed is:

1. A portable gas transfer device for point-of-use sterilization at a sterilization site, the device comprising:
   a housing;
   a pressurized gas canister held by the housing;
   a first passageway in fluid communication with the pressurized gas canister and configured to supply pressurized pre-sterilization gas from the pressurized gas canister to the site;
   a gas discharge canister held by the housing; and
   a second passageway in fluid communication with the gas discharge canister and configured to supply post-sterilization gas from the site to the gas discharge canister.

2. The portable gas transfer device of claim 1, further comprising a sensor disposed in the second passageway upstream of the gas discharge canister, the sensor configured to detect a characteristic of the post-sterilization gas.

3. The portable gas transfer device of claim 2, further comprising at least one controller configured to receive a detection signal from the sensor and determine whether the site has been adequately sterilized based on the received detection signal.

4. The portable gas transfer device of claim 3, further comprising at least one indicator on the housing to provide visual feedback that the site has been adequately sterilized based on a determination that the site has been adequately sterilized.

5. The portable gas transfer device of claim 3, further comprising a memory for storing data related to the received detection signal and/or the determination of whether the site has been adequately sterilized.

6. The portable gas transfer device of claim 3, wherein the controller is configured to determine whether the site has been sterilized to a Sterility Assurance Level (SAL) of $10^{-6}$.

7. The portable gas transfer device of claim 3, wherein the pressurized pre-sterilization gas is ozone, and wherein:
   the detected characteristic is an ozone level in the post-sterilization gas; and
   the controller is configured to determine whether the site has been adequately sterilized based on the ozone level over a period of time.

8. The portable gas transfer device of claim 7, wherein the gas discharge canister is a gas discharge catalyst canister comprising a catalyst material held therein, the catalyst material configured to convert waste ozone in the post-sterilization gas to oxygen.

9. The portable gas transfer device of claim 8, wherein the catalyst material comprises manganese dioxide/copper oxide, activated charcoal or a molecular sieve.

10. The portable gas transfer device of claim 8, further comprising a vent on the housing for the expulsion of oxygen from the gas discharge catalyst canister.

11. The portable gas transfer device of claim 1, further comprising a gas fill port valve on the housing, the gas fill port valve configured to receive pressurized gas from a recharging station to refill the pressurized gas canister.

12. The portable gas transfer device of claim 1, further comprising an electrical interface on the housing, the electrical interface configured to connect with an electrical connection to:
   recharge a battery pack of the portable gas transfer device; and
   transfer data to a database, wherein the data includes sterilization validation data.

13. A gas dispersion device, comprising:
   a housing defining a fluid flow path along an axis, the fluid flow path having first and second opposite ends, each of the first and second ends configured to operatively connect with at least one flow component;
   a gas flow member held in the housing, the gas flow member having an upper portion and a lower portion, the gas flow member comprising a supply gas passageway extending from a gas supply port at the upper portion to first and second gas dispersion openings at the bottom portion, the gas flow member further comprising first and second return gas passageways, each return gas passageway extending from a return gas opening at the bottom portion to a return discharge port at the upper portion;
   wherein the gas flow member is positionable in a sterilization position with the gas flow member lower portion disposed in the fluid flow path, wherein the gas dispersion openings are configured to disperse pressurized pre-sterilization gas received from the gas supply port to sterilize flow components operatively connected with the first and second ends of the fluid flow path, and wherein the return gas discharge ports are configured to discharge post-sterilization gas received from the return gas openings.

14. The gas dispersion device of claim 13, wherein the fluid flow path comprises a chamber and a pair of conduits extending away from the chamber, each conduit including a flange at a distal end thereof, the flanges defining the first and second ends of the fluid flow path.

15. The gas dispersion device of claim 13, further comprising at least one flow component operatively connected with each of the first and second ends of the fluid flow path, wherein the at least one flow component is at least one of a connector, a fitting, a flow passageway, a sensor and a transmitter.

16. The gas dispersion device of claim 15, wherein, in the sterilization position, the dispersion openings are configured to disperse gas received from the gas supply port around and/or past the flow components to achieve a Sterile Assurance Level (SAL) of $10^{-6}$ for the flow components.

17. The gas dispersion device of claim 13, wherein, in the sterilization position, the first and second gas dispersion openings are generally aligned with the axis.

18. The gas dispersion device of claim 13, wherein the gas flow member is movable between the sterilization position and a product flow position, wherein, in the product flow position, the lower portion of the gas flow member is withdrawn out of the fluid flow path.

19. The gas dispersion device of claim 18, wherein, in the product flow position, the fluid flow path is configured to receive bioprocessing fluid flow therethrough, and wherein the lower portion of the gas flow member includes a seal configured to seal the fluid flow path.

20. The gas dispersion device of claim 18, further comprising a locking mechanism to lock the device in product flow position.

21. The gas dispersion device of claim 18, further comprising a shear key held in the housing and at least one shear cutter access port on the housing, wherein the at least one shear cutter access port is configured to receive a shear cutter therethrough to cut the shear key, and wherein, when the shear key is cut, the gas flow member moves from the sterilization position to the product flow position.

22. The gas dispersion device of claim 13, wherein the device is single use disposable.

23. A system for sterilizing a process connection or joint, comprising:
(a) a gas dispersion device positioned in the process connection or joint, the gas dispersion device comprising:
a housing defining a fluid flow path; and
a gas flow member held in the housing, the gas flow member having an upper portion and a lower portion disposed in the fluid flow path, the gas flow member comprising a supply gas passageway extending from a gas supply port at the upper portion to at least one gas dispersion opening at the lower portion, the gas flow member further comprising at least one return gas passageway extending from a gas return opening at the lower portion to a gas discharge port at the upper portion; and
(b) a portable gas transfer device comprising:
a supply gas canister containing pressurized gas;
a gas discharge canister; and
a gas transport member in fluid communication with the supply gas canister and the gas discharge canister, the gas transport member held in a guided opening configured to receive the upper portion of the gas dispersion device;
wherein, when the upper portion of the gas flow member is received in the guided opening, the portable gas transfer device is configured to:
supply pre-sterilization pressurized gas from the supply gas canister to the at least one gas dispersion opening such that gas is dispersed in the fluid flow path to sterilize the process connection or joint; and
receive post-sterilization gas in the gas discharge canister from the at least one gas return opening.

24. The system of claim 23, wherein, when the upper portion of the gas flow member is received in the guided opening, the gas flow member and the gas transport member mate such that the supply gas passageway of the gas flow member is aligned with a supply passageway of the gas transport member and the at least one return gas passageway of the gas flow member is aligned with at least one discharge gas passageway of the gas transport member.

25. The system of claim 23, wherein the portable gas transfer device further comprises:
a gas sensor disposed in a passageway between the gas transport member and the gas discharge canister, the sensor configured to detect a characteristic of the post-sterilization gas; and
a controller configured to monitor the detected characteristic and validate that the process connection or joint has been sterilized based on detected characteristic.

26. The system of claim 25, wherein the portable gas transfer device is configured to halt the supply of pre-sterilization gas to the gas dispersion device after validation that the process connection or joint has been sterilized.

27. The system of claim 25, wherein the portable gas transfer device includes an indicator to provide visual feedback after validation that the process connection or joint has been sterilized.

28. A sterilization gas supply and refilling system for portable gas transfer devices, the system comprising:
a portable gas transfer device, comprising:
a housing;
a pressurized gas canister held by the housing, the pressurized gas canister configured to supply pressurized pre-sterilization gas to a sterilization site;
a gas discharge canister held by the housing, the gas discharge canister configured to receive post-sterilization gas from the sterilization site; and
a gas fill valve on the housing;
a portable gas transfer device docking station having a docking area configured to receive the portable gas transfer device, the docking area including a gas supply connection for attachment with the portable gas transfer device fill valve; and
a gas supply manifold, the gas supply manifold configured to supply pressurized gas through the gas supply connection to the portable gas transfer device pressurized gas canister, thereby refilling the pressurized gas canister.

29. The system of claim 28, wherein the portable gas transfer device further comprises an electrical interface on the housing, and wherein the docking area includes an electrical connection configured to:
charge a battery pack of the portable gas transfer device; and
receive data from memory of the portable gas transfer device, wherein the data includes sterilization validation data from at least one past sterilization event.

30. The system of claim 28, further comprising a gas supply unit configured to supply pressurized gas to the gas supply manifold.

31. The system of claim 30, wherein the pressurized gas is ozone, and wherein the gas supply unit comprises an ozone generation unit configured to generate ozone from an oxygen supply and/or a secondary gas supply.

32. The system of claim 28, wherein the pressurized gas is ozone, the system further comprising a gas catalytic converter in fluid communication with the gas supply manifold and the docking area, the gas catalytic converter configured to:
receive ozone gas that has been held in the portable gas transfer device and/or the gas supply manifold past a time limit;
convert the received ozone gas to oxygen; and
discharge the oxygen to atmosphere.

33. The system of claim 28, comprising a plurality of portable gas transfer devices and a plurality of docking areas, each docking area configured to receive one of the gas transfer devices.

* * * * *